United States Patent
Walensky

(10) Patent No.: US 9,926,306 B2
(45) Date of Patent: Mar. 27, 2018

(54) INHIBITION OF MCL-1 AND/OR BFL-1/A1

(71) Applicant: Dana-Farber Cancer Institute, Inc., Boston, MA (US)

(72) Inventor: Loren D. Walensky, Newton Centre, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 196 days.

(21) Appl. No.: 14/386,747

(22) PCT Filed: Mar. 14, 2013

(86) PCT No.: PCT/US2013/031705
§ 371 (c)(1),
(2) Date: Sep. 19, 2014

(87) PCT Pub. No.: WO2013/142281
PCT Pub. Date: Sep. 26, 2013

(65) Prior Publication Data
US 2015/0051249 A1    Feb. 19, 2015

Related U.S. Application Data

(60) Provisional application No. 61/613,225, filed on Mar. 20, 2012.

(51) Int. Cl.
| | | |
|---|---|---|
| *C07D 417/12* | (2006.01) | |
| *C07D 277/60* | (2006.01) | |
| *C07D 277/42* | (2006.01) | |
| *A61K 31/426* | (2006.01) | |
| *C07D 417/04* | (2006.01) | |
| *A61K 45/06* | (2006.01) | |
| *A61K 31/427* | (2006.01) | |
| *A61K 31/428* | (2006.01) | |
| *A61K 31/454* | (2006.01) | |
| *C07D 277/54* | (2006.01) | |
| *C07D 277/56* | (2006.01) | |

(52) U.S. Cl.
CPC .......... *C07D 417/12* (2013.01); *A61K 31/426* (2013.01); *A61K 31/427* (2013.01); *A61K 31/428* (2013.01); *A61K 31/454* (2013.01); *A61K 45/06* (2013.01); *C07D 277/42* (2013.01); *C07D 277/54* (2013.01); *C07D 277/56* (2013.01); *C07D 277/60* (2013.01); *C07D 417/04* (2013.01)

(58) Field of Classification Search
CPC ... C07D 417/12; C07D 277/60; C07D 277/42
See application file for complete search history.

(56) References Cited

U.S. PATENT DOCUMENTS

| | | |
|---|---|---|
| 2004/0002117 A1 | 1/2004 | Hogan et al. |
| 2004/0157883 A1 | 8/2004 | Chen et al. |
| 2004/0191328 A1 | 9/2004 | Warrell, Jr. et al. |
| 2007/0203236 A1 | 8/2007 | Smith et al. |
| 2009/0054402 A1 | 2/2009 | Wang |
| 2009/0069324 A1 | 3/2009 | Reed |
| 2009/0124616 A1 | 5/2009 | Song |
| 2009/0163545 A1 | 6/2009 | Goldfarb |
| 2010/0004324 A1 | 1/2010 | Skaar et al. |

(Continued)

FOREIGN PATENT DOCUMENTS

| | | |
|---|---|---|
| EP | 1475372 | 11/2004 |
| JP | 2004099518 | 4/2004 |

(Continued)

OTHER PUBLICATIONS

CAS Registry No. 473233-06-6, which entered STN on Nov. 12, 2002.*
Yoon et al. Journal of Biomolecular Screening 2008, 13(7), pp. 591-608.*
CAS Registry No. 481682-91-1, which entered STN on Jan. 27, 2003.*
CAS Registry No. 485371-82-2, which entered STN on Feb. 4, 2003.*
CAS Registry No. 455301-78-7, which entered STN on Sep. 26, 2002.*
Notification of transmittal of the international search report and the written opinion of the international searching authority, or the declaration, for PCT/US2013/031705 dated Jun. 25, 2013, 15 pages.
Berge et al., "Pharmaceutical Salts", J. Pharm. Sci. 66:1-19 (1977).

(Continued)

*Primary Examiner* — Matthew P Coughlin
(74) *Attorney, Agent, or Firm* — Fish & Richardson P.C.

(57) ABSTRACT

This disclosure features compounds and pharmaceutically acceptable salts thereof that inhibit MCL-1 and/or BFL-1/A1 and compositions containing the same. This disclosure also features combinations that include one or more of the MCL-1/BFL-1/A1 inhibitor compounds described herein, or a pharmaceutically acceptable salt thereof; and one or more additional therapeutic agents (e.g., one or more chemotherapeutic agents (including small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-XL, BCL-w, MCL-1, and/or BFL-1/A1; e.g., one or more therapeutic agents that directly bind to and inhibit anti-apoptotic BCL-2/BCL-XL; e.g., agents such as ABT-199, ABT-263 and ABT-737; e.g., ABT-737), or (where applicable) a pharmaceutically acceptable salt of the one or more therapeutic agents (as well as compositions containing the same). Also featured are methods of using such compounds, salts, combinations, and compositions, e.g., for the treatment or prevention of diseases, disorders, and conditions associated with deregulated apoptosis of cells (e.g., diseased or damaged cells; e.g., insufficient apoptosis of diseased or damaged cells or reduced apoptosis of diseased or damaged cells).

23 Claims, 21 Drawing Sheets

(56) References Cited

U.S. PATENT DOCUMENTS

| | | |
|---|---|---|
| 2010/0234456 A1 | 9/2010 | Wendt |
| 2011/0077250 A1 | 3/2011 | Ryder |
| 2012/0142917 A1 | 6/2012 | Lawrence et al. |

FOREIGN PATENT DOCUMENTS

| | | | |
|---|---|---|---|
| JP | 2006516383 | 7/2006 | |
| JP | 2007084494 | 4/2007 | |
| WO | WO 2004/069200 A2 | 8/2004 | |
| WO | WO 2008/131000 | 10/2008 | |
| WO | WO 2008/156676 | 12/2008 | |
| WO | WO 2009/023773 | 2/2009 | |
| WO | WO 2010/005534 A2 | 1/2010 | |
| WO | WO 2010/102286 A2 | 9/2010 | |
| WO | WO 2010/151799 A2 | 12/2010 | |
| WO | WO2011-094708 A2 | 8/2011 | |
| WO | WO 2011094708 A2 * | 8/2011 | ........... C07C 251/20 |
| WO | WO2011094708 A3 | 1/2012 | |

OTHER PUBLICATIONS

Bernal, F. et al., "A stapled p53 helix overcomes HDMX-mediated suppression of p53", Cancer Cell 18:411-22 (2010).
Beroukhim, R. et al., "The landscape of somatic copy-number alteration across human cancers", Nature 463:899-905 (2010).
Bird, G.H., et al., "Chapter 22 Synthesis and Biophysical Characterization of Stabilized alpha-Helices of BCL-2 Domains", Methods Enzymol., 446:369-86 (2008).
Chen, L. et al., "Differential targeting of prosurvival Bcl-2 proteins by their BH3-only ligands allows complementary apoptotic function", Mol Cell 17"393-403 (2005).
Chou, T.C., "Theoretical basis, experimental design, and computerized simulation of synergism and antagonism in drug combination studies", Pharmacol. Rev. 58:621-681 (2006).
Degterev, A. et al., "Identification of small-molecule inhibitors of interaction between the BH3 domain and Bcl-xL", Nat Cell Biol 3:173-82 (2001).
Delaglio, F. et al., "NMRPipe: a multidimensional spectral processing system based on UNIX pipes", J Biomol NMR 6:277-93 (1995).
Enyedy, I.J. et al., "Discovery of small-molecule inhibitors of Bcl-2 through structure-based computer screening", J Med Chem 44:4313-24 (2001).
Freireich et al., Cancer Chemother. Rep., 50:219 (1966).
Frenzel, A., et al., "Bcl2 family proteins in carcinogenesis and the treatment of cancer", Apoptosis 14:584-96 (2009).
Gandhi, L. et al., "Phase I study of Navitoclax (ABT-263), a novel Bcl-2 family inhibitor, in patients with small-cell lung cancer and other solid tumors", J Clin Oncol 29:909-16 (2011).
Gavathiotis et al., Nat Chem Biol,, 8:639-645 (2012).
Gavathiotis, et al., "BAX activation is initiated at a novel interaction site", Nature 455:1076-81 (2008).
Grzesiek, S. et al., "A. The importance of not saturating water in protein NMR: application to sensitivity enhancement and NOE measurements", J Am Chem Soc 115:12593-12594 (1993).
Johnson, B.A., "Using NMRView to visualize and analyze the NMR spectra of macromolecules", Methods Mol Biol 278:313-52 (2004).
Kang, M.H. et al., "Bcl-2 inhibitors: targeting mitochondrial apoptotic pathways in cancer therapy", Clin Cancer Res 15:1126-32 (2009).
Kitada, S. et al., "Discovery, characterization, and structure-activity relationships studies of proapoptotic polyphenols targeting B-cell lymphocyte/leukemia-2 proteins", J Med Chem 46:4259-64 (2003).
Konopleva, M. et al., "Mechanisms of apoptosis sensitivity and resistance to the BH3 mimetic ABT-737 in acute myeloid leukemia", Cancer Cell 10:375-388 (2006).
Lin, X. et al., "Seed" analysis of off-target siRNAs reveals an essential role of MCL-1 in resistance to the small-molecule Bcl-2/Bcl-xL inhibitor ABT-737, Oncogene 26:3972-3979 (2007).

Llambi, F. et al., "Apoptosis and oncogenesis: give and take in the BCL-2 family", Curr Opin Genet Dev, 21: 12-20 (2011).
Lovell, J.F. et al., "Membrane binding by tBid initiates an ordered series of events culminating in membrane permeabilization by Bax", Cell 135:1074-84 (2008).
Marintchev, A., et al., "NMR methods for studying protein-protein interactions involved in translation initiation", Methods Enzymol 430:283-331 (2007).
Negrin et al., Biomaterials, 22(6):563 (2001).
Nguyen, M. et al., "Small molecule obatoclax (GX15-070) antagonizes MCL-1 and overcomes MCL-1-mediated resistance to apoptosis", Proc Natl Acad Sci USA 104:19512-7 (2007).
Oltersdorf, T. et al., "An inhibitor of Bcl-2 family proteins induces regression of solid tumours", Nature 435:677-681 (2005).
Petros, A.M. et al., "Discovery of a potent and selective Bcl-2 inhibitor using SAR by NMR", Bioorg Med Chem Lett 20:6587-91 (2010).
Pitter, K., et al., "Dissection of the BCL-2 family signaling network with stabilized alpha-helices of BCL-2 domains", Methods Enzymol 446:387-408 (2008).
Remington's Pharmaceutical Sciences, 17th ed., Mack Publishing Company, Easton, Pa., 1985, p. 1418.
Roberts, A.W. et al., "Substantial susceptibility of chronic lymphocytic leukemia to BCL2 inhibitio: Results of Phase 1 study of navitoclax (ABT-263) in patients with relapsed or refractory disease", J Clin Onc (2011).
Sattler, M. et al., "Structure of Bcl-xL-Bak peptide complex: recognition between regulators of apoptosis", Science 275:983-6 (1997).
Shamas-Din, A., et al., "BH3-only proteins: Orchestrators of apoptosis", Biochim Biophys Acta 1813:508-20 (2011).
Souers et al., Nat Med 19:202-208 (2013).
Stewart, M.L., et al., "The MCL-1 BH3 helix is an exclusive MCL-1 inhibitor and apoptosis sensitizer", Nature Chem Biol 6:595-601 (2010).
Suzuki, M., et al., "Structure of Bax: coregulation of dimer formation and intracellular localization", Cell 103:645-54 (2000).
Tse, C. et al. "ABT-263: a potent and orally bioavailable Bcl-2 family inhibitor", Cancer Res 68:3421-8 (2008).
Tsujimoto, Y., et al., "Involvement of the bcl-2 Gene in Human Follicular Lymphoma", Science 228:1440-1443 (1985).
Tsujimoto, Y., et al., "Cloning of the chromosome breakpoint of neoplastic B cells with the t(14;18) chromosome translocation", Science 226"1097-1099 (1984).
Tzung, S.P. et al., "Antimycin A mimics a cell-death-inducing Bcl-2 homology domain 3", Nat Cell Biol 3:183-91 (2001).
van Delft, M.F. et al., "The BH3 mimetic ABT-737 targets selective Bcl-2 proteins and efficiently induces apoptosis via Bak/Bax if Mcl-1 is neutralized", Cancer Cell 10:389-399 (2006).
Vaux, D.L., et al., "Bcl-2 gene promotes haemopoietic cell survival and cooperates with c-myc to immortalize pre-B cells", Nature 335:440-442 (1988).
Walensky, L.D. et al., "BAX unleashed: the biochemical transformation of an inactive cytosolic monomer into a toxic mitochondrial pore", Trends Biochem Sci 36:642-52 (2011).
Walensky, L.D. et al., "A stapled BID BH3 helix directly binds and activates BAX", Mol Cell 24:199-210 (2006).
Walensky, L.D. et al., "Activation of apoptosis in vivo by a hydrocarbon-stapled BH3 helix", Science 305:1466-70 (2004).
Wang, G. et al., "Structure-based design of potent small-molecule inhibitors of anti-apoptotic Bcl-2 proteins", J Med Chem 49:6139-42 (2006).
Wang, J.L. et al., "Structure-based discovery of an organic compound that binds Bcl-2 protein and induces apoptosis of tumor cells", Proc Natl Acad Sci USA 97:7124-9 (2000).
Wilen, S.H., "Tables of Resolving Agents and Optical Resolutions", p. 268 (E.L. Eliel, Ed., Univ. of Notre Dame Press, Notre Dame, IN 1972).
Wilen, S.H., et al., Tetrahedron 33:2725 (1977).
Wilson, W.H. et al., "Navitoclax, a targeted high-affinity inhibitor of BCL-2, in lymphoid malignancies: a phase 1 dose-escalation study of safety, pharmacokinetics, pharmacodynamics, and antitumour activity", Lancet Oncol 11:1149-59 (2010).

(56) References Cited

OTHER PUBLICATIONS

Yecies, D., et al., "Acquired resistance to ABT-737 in lymphoma cells that up-regulate MCL-1 and BFL-1", Blood 115:3304-13 (2010).
Yethon, J.A., et al., "Interaction with a membrane surface triggers a reversible conformational change in Bax normally associated with induction of apoptosis", J Biol Chem 278:48935-41 (2003).
Youle, R.J. et al., "The BCL-2 protein family: opposing activities that mediate cell death", Nat Rev Mol Cell Biol 9:47-59 (2008).
Zhai, D., et al., "Comparison of chemical inhibitors of antiapoptotic BCL-2 family proteins", Cell Death Diff. 13:1419-1421 (2006).
International Search Report for Int. App. No. PCT/US2013/031705, dated Jun. 25, 2013.
Cohen et al., *A Competitive Stapled Peptide Screen Identifies a Selective Small Molecule that Overcomes MCL-1-Dependent Leukemia Cell Survival*, Chem & Biol., 19(9):1175-1186 (Sep. 2012).
Extended European Search Report for EP App. No. 13763682.5, dated Mar. 10, 2016 (9 pages).
Aiello et al., *Vascular Endothelial Growth Factor in Ocular Fluid of Patients With Diabetic Retinopathy and Other Retinal Disorders*, New Engl. J. Med., 331(22):1480- (1994).
Armstrong, S. A., et al., *Inhibition of FLT3 in MLL. Validation of a therapeutic target identified by gene expression based classification*, Cancer Cell 3(2):173-183 (2003).
Bakhshi, A., et al., *Cloning the chromosomal breakpoint of t(14;18) human lymphomas: clustering around JH on chromosome 14 and near a transcriptional unit on 18*, Cell 41(3):899-906 (1985).
Barret et al., "Preparation of Quinone-Imide Ketals From Amides with Hyper valent Organo-Iodine Compounds", Tetrahedron Letts., 32(19):2133-2134 (1991).
Boisvert-Adamo, K., et al., *Mcl-1 is required for melanoma cell resistance to anoikis*, Mol Cancer Res 7(4):549-556 (2009).
Bukhtoyarova et al., "Synthesis and Spectral Properties of N-Aryl-5-hydroxy-1,4-naphthoquinone 4-Imines", Russian J. Organ. Chem., 39(9):1309-1315 (2003).
Bukhtoyarova et al., "Dependence of Carbon Chemical Shifts in the $^{13}$C NMR Spectra of 5-Hydroxy-1,4-naphthoquinon-4-imines on Position of Tautomeric Equilibrium", Russian J. Organic Chem., 38(6):851-854 (2002).
CAS Registry No. 473233-06-6; STN Entry Date Nov. 12, 2002; 4-[[[2-(cyclohexylimino)-4-(2-thienyl)-3(2H)-thiazolyl]imino]methyl]- 1,2,3-benzenetriol.
CAS Registry No. 503290-13-9; STN Entry Date Apr. 17, 2003; 2-(cyclohexylimino)-4-methyl-N-[(2,4,5-trimethoxyphenyl)methylene]-3(2H)-thiazolamine.
CAS Registry No. 503006-71-1; STN Entry Date Apr. 15, 2003; 2-bromo-4-[[[2-(cyclohexylimino)-4-methyl-3(2H)-thiazolyl]imino]methyl]-6-methoxy-phenol.
CAS Registry No. 502565-41-5; STN Entry Date Apr. 10, 2003; 4-[[[2-(cyclohexylimino)-4-methyl-3(2H)-thiazolyl]imino]methyl]-2-methoxy-phenol.
CAS Registry No. 479387-53-6; STN Entry Date Jan. 17, 2003; 2-(cyclohexylimino)-N-[(2,4-dimethoxyphenyl)methylene]-4-methyl-3(2H)-thiazolamine.
CAS Registry No. 474914-01-7; STN Entry Date Dec. 3, 2002; 2-(cyclohexylimino)-4-methyl-N-[(2,3,4-trimethoxyphenyl)methylene]-3(2H)-thiazolamine.
CAS Registry No. 474791-96-3; STN Entry Date Dec. 2, 2002; 3-[[[2-(cyclohexylimino)-4-methyl-3(2H)-thiazolyl]imino]methyl]-1,2-benzenediol.
CAS Registry No. 1013591-26-8; STN Entry Date Apr. 10, 2008; 5-[2-(cyclopropylimino)-2,3-dihydro-3-[[(2,3,4-trimethoxyphenyl)methylene]amino]-4-thiazolyl]-2-hydroxy-benzamide.
CAS Registry No. 746606-31-5; STN Entry Date Sep. 17, 2004; 4-(5-bromo-2-thienyl)-2-(cyclopropylimino)-N-[(2,3,4-trimethoxyphenyl)methylene]-3(2H)-thiazolamine.
CAS Registry No. 733042-52-9; STN Entry Date Aug. 26, 2004; 2-(cyclopropylimino)-4-[(4-methoxyphenyl)methylene]-3(2H)-thiazolamine.
CAS Registry No. 491635-11-1; STN Entry Date Feb. 18, 2003; 2-(cyclohexylimino)-4-(2-thienyl)-N-[(3,4,5-trimethoxyphenyl)methylene]-3(2H)-thiazolamine.
CAS Registry No. 491643-99-3; STN Entry Date Feb. 18, 2003; 3-[[[2-(cyclohexylimino)-4-phenyl-3(2H)-thiazolyl]imino]methyl]-1,2-benzenediol.
CAS Registry No. 479700-04-4; STN Entry Date Jan. 22, 2003; 4-[[[2-(cyclohexylimino)-4-phenyl-3(2H)-thiazolyl]imino]methyl]-2,6-dimethoxy-phenol.
CAS Registry No. 479369-50-1; STN Entry Date Jan. 17, 2003; 2-(cyclohexylimino)-4-phenyl-N-[(2,4,5-trimethoxyphenyl)methylene]-3(2H)-thiazolamine.
CAS registration No. 794552-61-7 Registry (STN) [online], Dec. 8, 2004,[searching date Oct. 27, 2014].
CAS Registration No. 794552-60-6 Registry (STN) [online], Dec. 8, 2004, [searching date Oct. 27, 2014].
CAS Registration No. 315698-78-3 Registry (STN) [online], Jan. 22, 2001, [searching date Oct. 27, 2014].
STN CAPLUS 2010:1626364/AN WO 2010151799/US 20110077250, Priority date: US 2009-61220988 filed on Jun. 26, 2009.
Cleary, and Sklar, *Nucleotide sequence of a t(14; 18) chromosomal breakpoint in follicular lymphoma and demonstration of a breakpoint-cluster region near a transcriptionally active locus on chromosome 18*, Proc Natl Acad Sci USA 82(21):7439-7443 (1985).
Danial, N. N., et al., *Dual role of proapoptotic BAD in insulin secretion and beta cell survival*, Nat Med 14(2):144-153 (2008).
Deng, J., et al., *BH3 profiling identifies three distinct classes of apoptotic blocks to predict response to ABT-737 and conventional chemotherapeutic agents*, Cancer Cell 12(2):171-185 (2007).
Derenne, S., et al., *Antisense strategy shows that Mcl-1 rather than Bcl-2 or Bcl-x$_L$, is an essential survival protein of human myeloma cells*, Blood 100(1):194-199 (2002).
Ding, Q., et al., *Myeloid Cell Leukemia-1Inversely Correlates with Glycogen Synthase Kinase-3 {beta} Activity and Associates with Poor Prognosis in Human Breast Cancer*, Cancer Res 67(10):4564-4571 (2007).
Ektova et al., "Synthesis and Isomerization of N, N'-Diaryl-2,2'-BI(1,4-Naphtho-Quinone) 4,4'-Diimines", J. Organ. Chem. of the USSR, 22:748-752 (1986).
Ficarro SB, et al., *Improved electrospray ionization efficiency compensates for diminished chromatographic resolution and enables proteomics analysis of tyrosine signaling in embryonic stem cells*, Anal Chem. 81(9):3440-7 (2009).
Granero et al., "Synthesis of New Isoxazolylnaphthoquinones as Potential Trypanocidal and Antibacterial Agents", J. Chem. Research (S), 2:110-111 (1999).
Jensen et al., (2010) *Anodic Oxidation and Organocatalysis: Direct Regio- and Stereoselective Access to meta-Substituted Anilines by alpha-Arylation of Aldehydes*, Angew. Chem. Int. Ed. 49:129-133.
Johnson et al., "Synthesis and Antibacterial Activity of 1-(Arylamino)-1H-pyrroles and 4-(1H-Pyrrol-1-ylimino)-2,5-cyclohexadienes", J. Med. Chem., 24(11):1314-1319 (Nov. 1981).
Khalil et al., "Synthesis and study of some new 1,3-isoindoledione derivatives as potential antibacterial agents", European J. Med. Chem., 45(4):1552-1559 (2010).
Kline, M. P., et al., *ABT-737, an inhibitor of Bcl-2 family proteins, is a potent inducer of apoptosis in multiple myeloma cells*, Leukemia 21(7):1549-1560 (2007).
Kung et al., "Photegenerated N-Methyl-N-1-naphthylnitrenium Ion: Laser Flash Photolysis, Trapping Rates, and Product Study"., J. Org. Chem., 70:3127-3132 (2005).
Lopez et al., *Transdifferentiated Retinal Pigment Epithelial Cells Are Immunoreactive for Vascular Endothelial Growth Factor in Surgically Excised Age Related Macular Degeneration Related Choroidal Neovascular Membranes*, Invest. Opththalmol Vis. Sci., 37(5):855-868 (1996).
MacVicar, G. R., et al., *An open-label, multicenter, phase I/II study of AT-101 in combination with docetaxel (D) and prednisone (P) in men with hormone refractory prostate cancer (HRPC)*, J Clin Oncol 26:16043 (Abstract) (2008).

(56) References Cited

OTHER PUBLICATIONS

Muchmore, et al., *X-ray and NMR structure of human Bcl-xL, an inhibitor of programmed cell death*, Nature, 381(6580):335-341 (1996).
Myung et al., "2D-QSAR and HQSAR of the Inhibition of Calcineurin-NFAT Signaling by Blocking Protein-Protein Interaction with N-(4-oxo-1(4H)-naphthalenylidenebenzenesulfonamide Analogues", Arch Phatm Res, 30(8):976-983 (2007).
Pe'er et al., *Hypoxia-Induced Expression of Vascular Endothelial Growth Factgor by Retinal Cells is a Common Factor in Neovascularizing Ocular Diseases*, Laboratory Investigation, 72(6):638-645 (1995).
PubChem ZINC15913384, PubChem SID 59797118, PubChem CID: 6848561 (509102-00-5), Available Date: May 28, 2009. http://pubchem.ncbi.nlm.nih.gov/substance/59797118/version/1.
PubChem Compound Summary—CID 3318217, AC1MOCNT, NIH, U.S. Natl Library of Medicine, National Center for Biotechnology Information, Aug. 11, 2016, (11 pages).
PubChem Compound Summary—CID 5433262, STK215536, NIH, U.S. Natl Library of Medicine, National Center for Biotechnology Information, Aug. 11, 2016, (14 pages).
PubChem Compound Summary—CID 22525618, NIH, U.S. Natl Library of Medicine, National Center for Biotechnology Information, Aug. 11, 2016, (11 pages).
PubChem Compound Summary—CID 7728365, GNF-Pf-1078, NIH, U.S. Natl Library of Medicine, National Center for Biotechnology Information, Aug. 11, 2016, (14 pages).
PubChem Compound Summary—CID 2235899, ZINC02883560, NIH, U.S. Natl Library of Medicine, National Center for Biotechnology Information, Aug. 11, 2016, (11 pages).
PubChem Compound Summary—CID 24319562, STK981930, NIH, U.S. Natl Library of Medicine, National Center for Biotechnology Information, Aug. 11, 2016, (11 pages).
PubChem Compound Summary—CID 9611934, F0808-0868, NIH, U.S. Natl Library of Medicine, National Center for Biotechnology Information, Aug. 11, 2016, (11 pages).
PubChem Compound Summary—CID 9568012, ST50774387, NIH, U.S. Natl Library of Medicine, National Center for Biotechnology Information, Aug. 11, 2016, (11 pages).
PubChem Compound Summary—CID 9567065, AQ-390/12597145, NIH, U.S. Natl Library of Medicine, National Center for Biotechnology Information, Aug. 11, 2016, (11 pages).
PubChem Compound Database—MLS000774515, National Center for Biotechnology Information. CID 5894545, https://pubchem.ncbi.nlm.nih.gov/compound/5894545 (accessed Oct. 21, 2016).
PubChem Compound Database—509102-00-5, National Center for Biotechnology Information. CID 6848561, https://pubchem.ncbi.nlm.nih.gov/compound/6848561 (accessed Oct. 21, 2016).
PubChem Database and ChemCats database search results accompanying EP Office Action dated Sep. 30, 2014.
PubChem Database Compound [Online], NCBI; May 30, 2009, Database accession No. CID 42371696
PubChem Database Compound [Online], NCBI; May 30, 2009, Database accession No. CID 42504827.
Reed et al., "Identification and Characterization of the First Small Molecule Inhibitor of MDMX" J. Biol. Chem, 285(14):10786-10796 (Apr. 2010).
Richter et al., "The Lead Tetraacetate Oxidation of 1- and 2-Benzenesulfonamido- and Benzamido-naphthalenes", J. Organic Chemistry, 27(11):4066-4068 (1962).
Schafineister, C., et al., *An all-hydrocarbon cross-linking system for enhancing the helicity and metabolic stability of peptides*, J Am Chem Soc 122:5891-5892 (2000).
Shuker, S. B., et al., *Discovering high-affinity ligands for proteins: SAR by NMR*, Science 274(5292):1531-1534 (1996).
Sicardi et al., "Mutagenic activity of isoxazolylnaphthoquinoneimines assayed by micronucleus bone marrow test", Mutation Res., 343:61-66 (1995).
Sperandeo et al., "Synthesis, antiprotozoal and cytotoxic activities of new N-(3,4-dimethyl-5-isoxazolyl)-1,2-naphthoquinone-4-amino derivatives"., IL FARMACO., 59:431-435 (2004).
Taniai, M., et al., *Mcl-1 mediates tumor necrosis factor-related apoptosis-inducing ligand resistance in human cholangiocarcinoma cells*, Cancer Res 64(10):3517-3524 (2004).
Tsujimoto, et al., *The t(14;18) chromosome translocations involved in B-cell neoplasms result from mistakes in VDJ joining*, Science 229(4720):1390-1393 (1985).
Walensky, L. D., *BCL-2 in the crosshairs: tipping the balance of life and death*, Cell Death Differ 13(8):1339-1350 (2006).
Wosikowski et al., "Identification Inhibitors by Correlation of Epidermal Growth Factor Receptor and c-erbB2 Pathway With Gene Expression Patterns", J. Natl. Cancer Inst., 89(20):1505-1515 (Jan. 1997).
Zhai, et al., *Differential regulation of Bax and Bak by anti-apoptotic Bcl-2 family proteins Bcl-B and Mcl-1*, J Biol Chem, 283(15): 9580-958 (2008).
Zhang, B., et al., *Myeloid cell factor-1 is a critical survival factor for multiple myeloma*, Blood 99(6):1885-1893 (2002).
AU Patent Examination Report No. 1 for Application No. AU2013235425 dated Sep. 29, 2016 (13 pages).
EPO Examination Report for EP App. No. 11737834.9, dated Aug. 26, 2016 (4 pages).
EPO Office Action issued in EP Patent Application No. 11737834.9-1462, dated Sep. 30, 2014.
EPO European Search Report for Application No. EP 11737834.9-1452/2528893, dated Jun. 25, 2013.
JPO Office Action for Japanese Patent App. No. 2012-551374, dated Jun. 2, 2015 (with English translation) (9 pages).
JPO Office Action issued in JP Patent Application No. 2012-551374, dated Nov. 11, 2014 with English Translation (13 pages).
Bilinski et al., *Condensation of 4-R-thiosemicarbazones of Pyridine Aldehydes with α-halogenketone. I. Condensation of Nicotinaldehyde 4-R-thiosemicarbazones with Chloroacetone and ω-chloracetophenone*, Annales Universitatis Mariae Curie-Sklodowska. Lublin, PL, 23(16)AA:107-115, Jan. 1, 1968 [With English Summary—See p. 9].
Bilinski, et al., *Condensation of 4-R-thiosemicarbazones of Pyridine Aldehydes with α-nalogen-ketones. II. Condensation of Isonicotinaldehyde 4-R-thiosemicarbazone with Chloroacetone and ω-chloroacetophenone*, Annales Universitatis Mariae Curie Skoldowska, Medi, Uniwersytet Marii Curie-Skodowskiej. Akademia Medyzna, Lublin, PL, 25(49)D:541-547, Jan. 1, 1970 [With English Summary—see p. 7].
Hünig et al., *Umlagerungen in der Thiazolreihe*, Journal Fuer Praktische Chemie (LEIPZIG), 8(5-6):264-278, Jun. 1, 1959 [With English translation of Abstract].
Kleinrok et al., *Some Pharmacological characteristics of new derivatives of pyridine aldehyde hydrazones*, Annales Universitatis Mariae Curie Sklodowska. Medi, Uniwersytet Marii Curie, Akademia Medyzna, Lublin, PL, 26(15)D:127-135, Jan. 1, 1971 [With English Summary—See pp. 8-9.
PubChem Compound [Online] AC1M621Y—Database accession No. CID 2340270, NCBI; Jul. 15, 2005, (12 pages).
Traverso, *Sul comportamento di alcune 3-amino-4-metil-tiazolon-2-imidi nei confronti delle aldeidi aromatiche*, Gazzetta Chimica Ital, Societa Chimica Italiana, IT, 85:956-964, Jan. 1, 1955 [With English translation of Abstract].
EPO, Extended European Search Report for Application No. 16192483.2, dated Jan. 23, 2017 (11 pages).
CAS Registration No. 473428-25-0 Registry(STN) [online] Nov. 13, 2002 [date of search Jan. 26, 2017].
CAS Registration No. 478937-00-7 Registry(STN) [online] Jan. 14, 2003 [date of search Jan. 26, 2017].
CAS Registration No. 481698-76-4 Registry(STN) [online] Jan. 27, 2003 [date of search Jan. 26, 2017].
CAS Registration No. 481711-53-9 Registry(STN) [online] Jan. 27, 2003 [date of search Jan. 26, 2017].
CAS Registration No. 482285-08-5 Registry(STN) [online] Jan. 28, 2003 [date of search Jan. 26, 2017.
CAS Registration No. 482352-04-5 Registry(STN) [online] Jan. 28, 2003 [date of search Jan. 26, 2017].

(56) References Cited

OTHER PUBLICATIONS

CAS Registration No. 502886-05-7 Registry(STN) [online] Apr. 14, 2003 [date of search Jan. 26, 2017].
CAS Registration No. 509102-00-5 Registry(STN) [online] May 2, 2003 [date of search Jan. 26, 2017].
CAS Registration No. 722476-42-8 Registry(STN) [online] Aug. 5, 2004 [date of search Jan. 26, 2017].
CAS Registration No. 728908-54-1 Registry(STN) [online] Aug. 19, 2004 [date of search Jan. 26, 2017].
CAS Registration No. 730256-75-4 Registry(STN) [online] Aug. 22, 2004 [date of search Jan. 26, 2017].
CAS Registration No. 730256-77-6 Registry(STN) [online] Aug. 22, 2004 [date of search Jan. 26, 2017].
CAS Registration No. 732264-56-17 Registry(STN) [online] Aug. 25, 2004 [date of search Jan. 26, 2017].
CAS Registry No. 1164463-47-1 Registry STN [online], https://stneasy.cas.org/tmp/20170518/79995-0183252827-200/236318139.clean.html May 18, 2017.
CAS Registry No. 1164469-80-0 Registry STN [online], https://stneasy.cas.org/tmp/20170518/79995-0183252827-200/218673_776.clean.html May 18, 2017.
CAS Registry No. 1164475-30-2 Registry STN [online], https://stneasy.cas.org/tmp/20170518/79995-0183252827-200/128995690.clean.html May 18, 2017.
CAS Registry No. 1164478-76-5 Registry STN [online], https://stneasy-japan.cas.org/tmp/20170521/155962-1981728486-300/518250663.clean.html May 22, 2017.
CAS Registry No. 1164482-47-6 Registry STN [online], https://stneasy.cas.org/tmp/20170518/79995-0183252827-200/69065964.clean.html May 18, 2017.
CAS Registry No. 1164482-52-3 Registry STN [online] https://stneasy.cas.org/tmp/20170518/79995-0183252827-200/329817829_.clean.html May 18, 2017.
CAS Registry No. 1164482-75-0 Registry STN [online] https://stneasy.cas.org/tmp/20170518/79995-0183252827-200/350996572.clean.html May 18, 2017.
CAS Registry No. 1164502-80-0 Registry STN [online] https://stneasy.cas.org/tmp/20170518/79995-0183252827-200/688640520.clean.html May 18, 2017.
CAS Registry No. 1164503-48-3 Registry STN [online] https://stneasy.cas.org/tmp/20170518/79995-0183252827-200/30907460_I_.clean.html May 18, 2017.
CAS Registry No. 1164508-84-2 Registry STN [online] https://stneasy.cas.org/tmp/20170518/79995-0183252827-200/27945708.clean.html May 18, 2017.
CAS Registry No. 1164510-53-5 Registry STN [online] https://stneasy.cas.org/tmp/20170518/79995-0183252827-200/7_18275408.clean.html May 18, 2017.
CAS Registry No. 1164510-72-8 REGISTRYSTN [online] https://stneasy.cas.org/tmp/20170518/79995-0183252827-200/7296445_.clean.html May 18, 2017.
CAS Registry No. 1164513-93-2 Registry STN [online] https://stneasy.cas.org/tmp/20170518/79995-0183252827-200/267113598.clean.html May 18, 2017.
CAS Registry No. 1164516-60-2 Registry STN [online] https://stneasy.cas.org/tmp/20170518/79995-0183252827-200/520099716.clean.html May 18, 2017.
CAS Registry No. 1164531-53-6 Registry STN [online] https://stneasy.cas.org/tmp/20170518/79995-0183252827-200/120229496.clean.html May 18, 2017.
CAS Registry No. 1164541-91-6 Registry STN [online] https://stneasy.cas.org/tmp/20170518/79995-0183252827-200/660593334.clean.html May 18, 2017.
CAS Registry No. 1164543-50-3 Registry STN [online] https://stneasy.cas.org/tmp/20170518/79995-0183252827-200/418035717_.clean.html May 18, 2017.
CAS Registry No. 1164545-71-4 Registry STN [online] https://stneasy.cas.org/tmp/20170518/79995-0183252827-200/562824943_.clean.html May 18, 2017.
CAS Registry No. 1164546-81-9 Registry STN [online] https://stneasy.cas.org/tmp/20170518/79995-0183252827-200/204180515_.clean.html May 18, 2017.
CAS Registry No. 1164551-66-9 Registry STN [online] https://stneasy.cas.org/tmp/20170518/79995-0183252827-200/93312748.clean.html May 18, 2017.
CAS Registry No. 1164554-95-3 Registry STN [online] https://stneasy.cas.org/tmp/20170518/79995-0183252827-200/160120168.clean.html May 18, 2017.
CAS Registry No. 1164556-04-0 Registry STN [online] https://stneasy.cas.org/tmp/20170518/79995-0183252827-200/410250913_.clean.html May 18, 2017.
CAS Registry No. 1164556-15-3 Registry STN [online] https://stneasy.cas.org/tmp/20170518/79995-0183252827-200/380019195_.clean.html May 18, 2017.
CAS Registry No. 1164557-96-3 Registry STN [online] https://stneasy.cas.org/tmp/20170518/79995-0183252827-200/17848421_.clean.html May 18, 2017.
CAS Registry No. 1164558-61-5 Registry STN [online] https://stneasy.cas.org/tmp/20170518/79995-0183252827-200/330861997_.clean.html May 18, 2017.
JPO Official Action for JP Pat. App. No. 2016-097054, dated Apr. 13, 2017 (9 pages) [with English Translation].
Lesyk et al., *New thiazolidones-4 with pyrazolone-5 substituent as the potential NSAIDs*, Bollettino Chimico Farmaceutico, 137(6):210-217 (1998).
Sakamoto et al., *Studies on Effects of Drugs upon Protoscoleces of Echinococcus granulosus in Vitro*, Memoirs of Faculty of Agriculture Kagoshima University, 15:125-30 (1979).
AU Examination Report No. 1 for Australian App. No. 2011210567, dated Jan. 29, 2010 (5 pages).
EPO Examination Report for EP App. No. 11737834.9 dated Sep. 20, 2017 (4 pages).
EPO Examination Report for EP App. No. 11737834.9 dated Jan. 2, 2017 (4 pages).
EPO Examination Report for EP App. No. 13763682.5 dated Mar. 14, 2017 (7 pages).
JPO Official Action for JP App. No. 2016-097054 dated Apr. 13, 2017 (10 pages) [With English Translation].
CAS Registry No. 1010960-60-7; STN Entry Date Mar. 30, 2008; 4[2-(cyclohexylimino)-2,3-dihydro-3-((2-pyridinylmethylene)amino]-4-thiazolyl]-1,3-benzenediol, 1 page.
Cas Registry No. 1062109-16-3; STN Entry Date Oct. 16, 2008; 5-[(2Z)-2-(cyclopropylimino)-3-[(E)-[(4-fluorophenyl )methylene]amino]-2,3-dihydro-4-thiazolyl]-2-hydroxy-benzamide, 1 page.
CAS Registry No. 1177738-13-4; STN Entry Date Aug. 30, 2009; (2Z)-4-methyl-2-(cyclohexylimino)-N((2,4-dichlorophenyl)methylene]-3(2H)-thiazolamine, 1 page.
CAS Registry No. 452280-05-6; STN Entry Date Sep. 18, 2002; 2-(cyclohexylimino)-4-(2-furanyl)-N-(2-furanylmethylene)-3(2H)-thiazolamine, 1 page.
CAS Registry No. 455313-09-4; STN Entry Date Sep. 26, 2002; N-(1,3-benzodioxol-5-ylmethylene)-2-(cyclohexylimino)-4-methyl-3(2H)-thiazolamine, 1 page.
CAS Registry No. 455322-89-1; STN Entry Date Sep. 26, 2002; 4-[[[2-(cyclohexylimino )-4-(2-furanyl)-3(2H)-thiazolyl ]imino]methyl]-1,2,3-benzenetriol, 1 page.
CAS Registry No. 473581-27-0; STN Entry Date Nov. 14, 2002; 4-[[[2-(cyclohexylimino)-4-methyl-3(2H)thiazolyl]imino ]methyl]-2-ethoxy-phenol, 1 page.
CAS Registry No. 478856-87-0; STN Entry Date Jan. 13, 2003; 2-(cyclohexylimino)-4-methyl-N(phenylmethylene)-3(2H)-thiazolamine, 1 page.
CAS Registry No. 479363-09-2; STN Entry Date Jan. 17, 2003; 3-[[[2-(cyclohexylimino)-4-(2,4-dimethoxyphenyl)-3(2H)-thiazolyl]imino]methyl]-phenol, 1 page.
CAS Registry No. 482348-78-7; STN Entry Date Jan. 28, 2003; 4-[[[2-(cyclohexylimino)-4-(2,4-dimethoxyphenyl)-3(2H)-thiazolyl]imino]methyl]-1,2,3-benzenetriol, 1 page.
CAS Registry No. 485371-71-9; STN Entry Date Feb. 4, 2003; N-(1,3-benzodioxol-5-ylmethylene)-2-(cyclohexyl imino)-4-(2,5-dimethoxyphenyl)-3(2H )-thiazolamine, 1 page.

(56) References Cited

OTHER PUBLICATIONS

CAS Registry No. 485373-60-2; STN Entry Date Feb. 4, 2003; 4-[[[2-(cyclohexylimino)-4-(2-furanyl)-3(2H)-thiazolyl ]imino]methyl]-1,2-benzenediol, 1 page.

CAS Registry No. 485771-08-2; STN Entry Date Feb. 5, 2003; 2-(cyclohexylimino)-4-(3,4-dimethylphenyl)-N-(1 H-pyrrol-2-ylmethylene)-3(2H)-thiazol, 1 page.

CAS Registry No. 502873-17-8; STN Entry Date Apr. 14, 2003; 4-[[[2-(cyclohexylimino)-4-(3,4,5-trimethoxyphenyl)-3(2H)-thiazolyl]imino]methyl]-1,2,3-benzenetriol, 1 page.

CAS Registry No. 502982-98-1; STN Entry Date Apr. 15, 2003; 4-[[[2-(cyclohexylimino)-4-(2,5-dichlorophenyl)-3(2H)-thiazolyl]imino]methyl]-1,2,3-benzenetriol, 1 page.

CAS Registry No. 502991-49-3; STN Entry Date Apr. 15, 2003; 4-(([2-(cyclohexylimino)-4-(2,4-dichlorophenyl)-3(2H)-1,2,3-benzenetriol, 1 page.

CAS Registry No. 503022-28-4; STN Entry Date Apr. 15, 2003; 4-(([2-(cyclohexylimino)-4-(3,4-dichlorophenyl)-3(2H)-thiazolyl]imino]methyl]-1,2,3-benzenetriol, 1 page.

CAS Registry No. 503145-61-7; STN Entry Date Apr. 16, 2003; 2-(cyclohexylimino)-4-(3,4-dimethylphenyl)-N-(2-th ienyl methylene )-(2H )-thiazolamine, 1 page.

CAS Registry No. 503297-48-1; STN Entry Date Apr. 17, 2003; 4-(([2-(cyclohexylimino)-4-(2,4-dichlorophenyl)-3(2H)-thiazolyl]imino]methyl]-1,3-benzenediol, 1 page.

CAS Registry No. 507457-35-4; STN Entry Date Apr. 30, 2003; 2-(cyclohexylimino)-N-(4-pyridinylmethylene)-4-(3,4,5-trimethoxyphenyl)-3(2H)-thiazolamine, 1 page.

CAS Registry No. 733043-64-6; STN Entry Date Aug. 26, 2004; 4-[[[2-(cyclohexylimino)-4-(2-furanyl)-3(2H)-thiazolyl]imino]methyl]-benzoic acid methyl ester, 1 page.

Examination Report No. 2 for Australian Application No. 2013235425, dated Jun. 22, 2017, 13 pages.

U.S. Appl. No. 14/705,764, filed May 6, 2015, Walensky.

\* cited by examiner

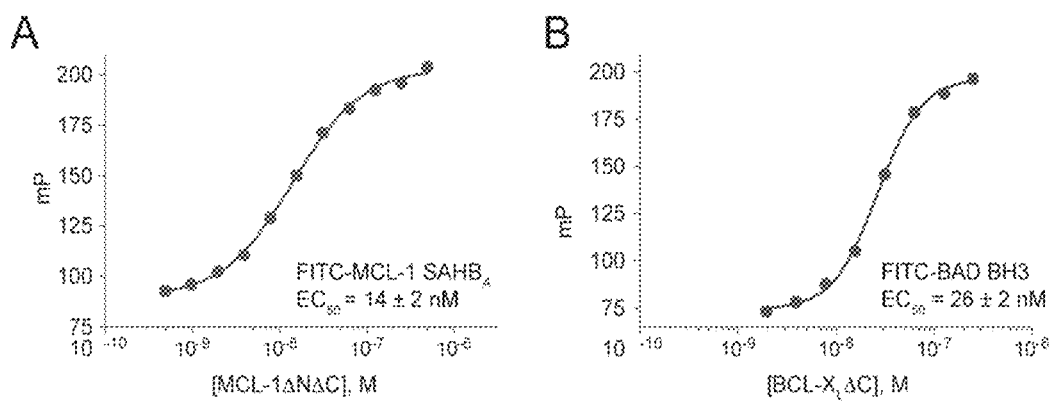
Figure 1. Development of a Stapled Peptide-based High-Throughput Competitive Screening Assay for Identifying MCL-1-selective Small Molecules. High-throughput competitive fluorescence polarization (FP) binding assays were developed based on the direct binding interaction between FITC-MCL-1 SAHB$_A$ and MCL-1ΔNΔC (EC$_{50}$, 14 nM) and FITC-BAD BH3 and BCL-X$_L$ΔC C (EC$_{50}$, 26 nM).

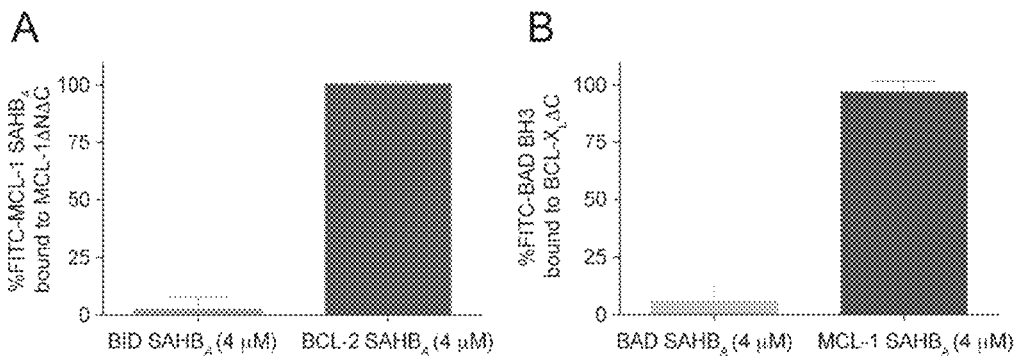

Figure 2. Positive and Negative Controls for Screening Conditions. The initial screening conditions were validated for (A) MCL-1 screening using a positive control for complete displacement (BID SAHB$_A$) and a negative control for no displacement (BCL-2 SAHB$_A$), and for (B) BCL-X$_L$ counterscreening using a positive control for complete displacement (BAD SAHB$_A$) and a negative control for no displacement (MCL-1 SAHB$_A$).

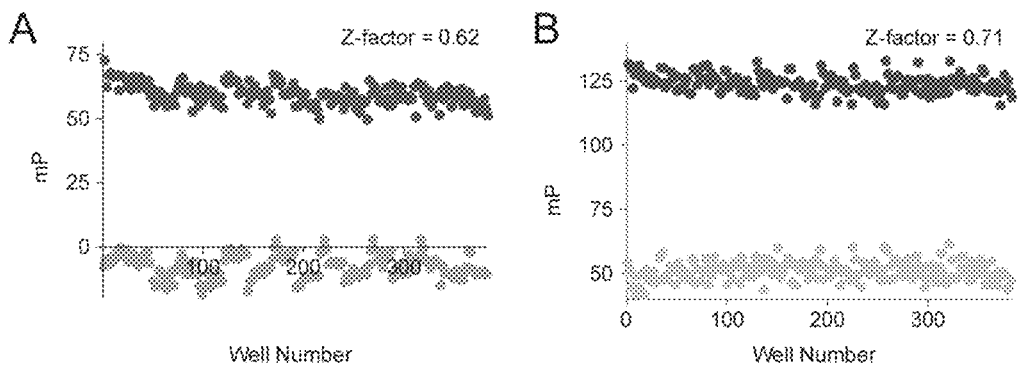

Figure 3. Z-factor Determination for the MCL-1 Screen and BCL-X$_L$ Counterscreen. (A) The MCL-1 screen yielded a Z-factor of 0.62, and (B) the BCL-X$_L$ counterscreen yielded a Z-factor of 0.71.

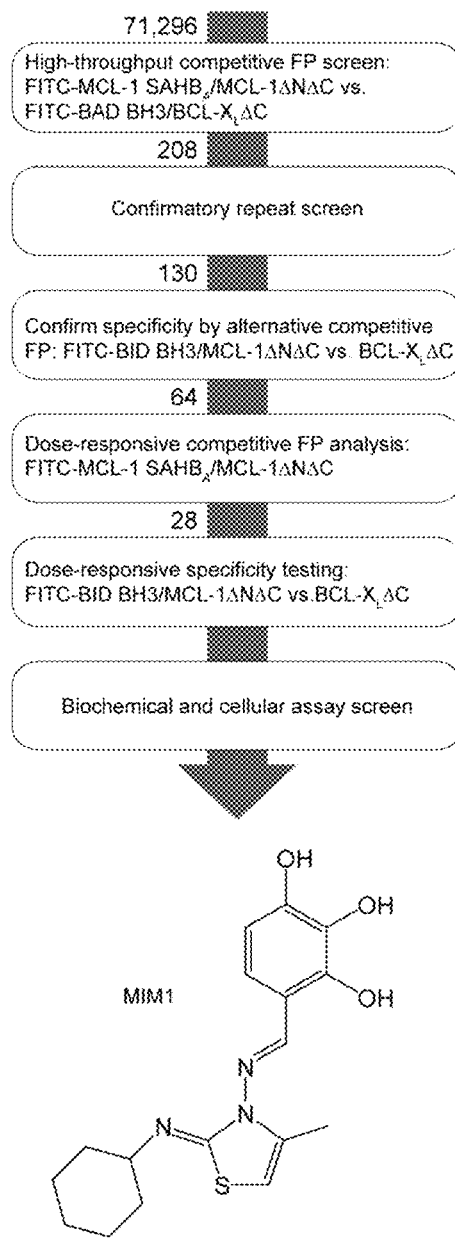
Figure 4. Identification of a Selective Inhibitor of Anti-apoptotic MCL-1.
A high-throughput stapled peptide-based screen for small molecules that selectively target MCL-1ΔNΔC identified MIM1. The molecular structure of MIM1 is characterized by a thiazolyl core substituted with methyl, cyclohexylimino, and benzenetriol R groups.

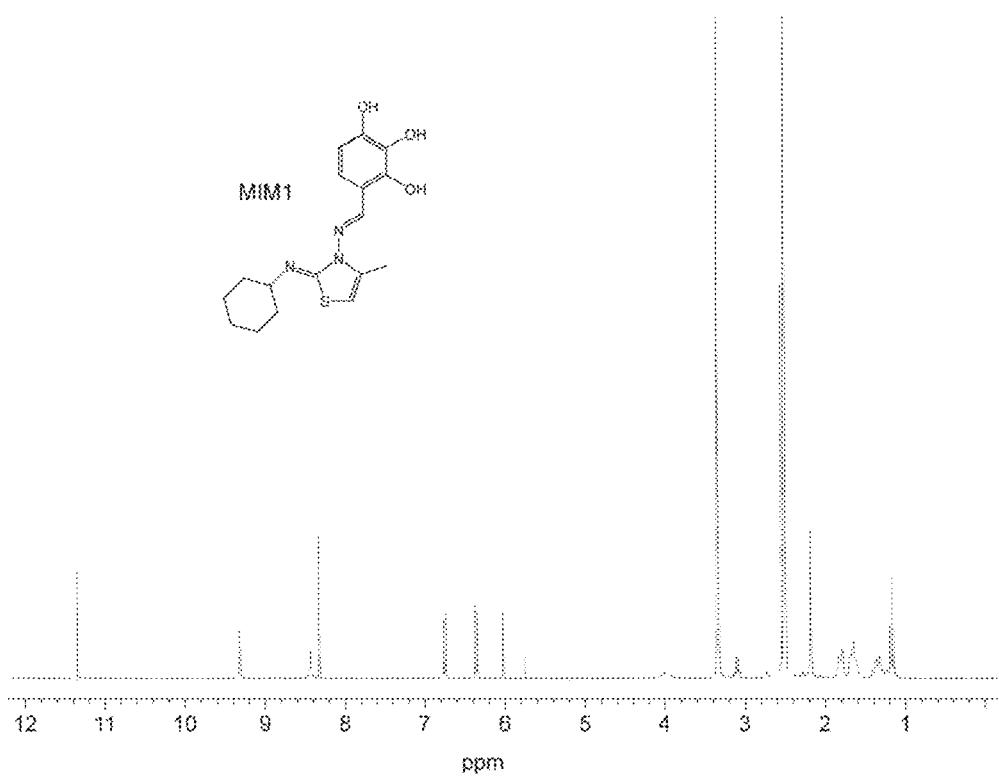
Figure 5. $^1$H NMR of MIM1.

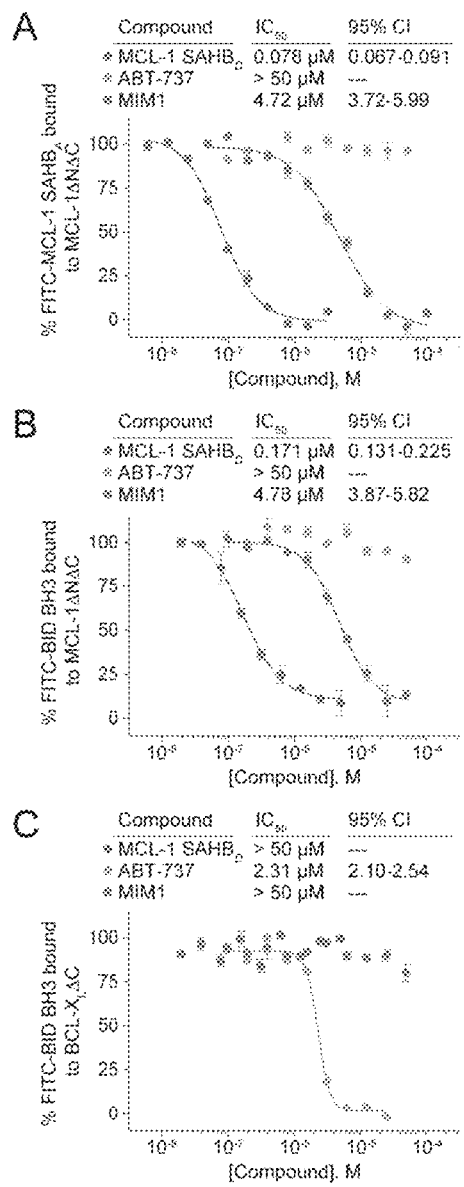

Figure 6. MIM1 binds MCL-1 selectively in an FP competition assay. (A) MCL-1 SAHB$_D$ and MIM1 dose-responsively compete with FITC-MCL-1 SAHB$_A$ for binding to MCL-1ΔNΔC, whereas the BCL-2/BCL-X$_L$-selective antagonist ABT-737 has no effect. (B) Similarly, MCL-1 SAHB$_D$ and MIM1, but not ABT-737, effectively compete with FITC-BID BH3 peptide for binding to MCL-1ΔNΔC.
(C) In contrast, ABT-737 dose-responsively competes with FITC-BID BH3 for binding to BCL-X$_L$ΔC, whereas MCL-1 SAHB$_D$ and MIM1 show no BCL-X$_L$ΔC-binding activity. Data are mean ± SEM for experiments performed in duplicate and repeated twice with independent preparations of recombinant protein with similar results.

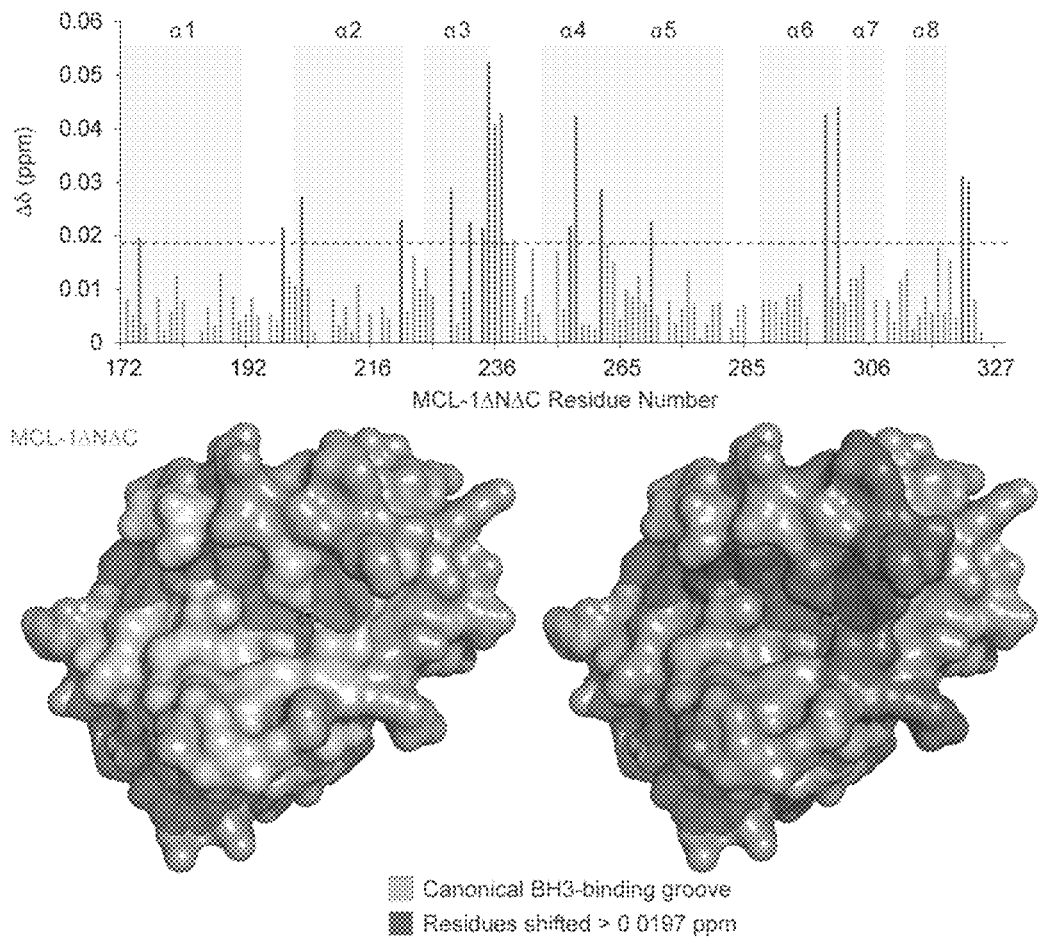

Figure 7. MIM1 Targets the Canonical BH3-Binding Pocket of MCL-1.
Measured chemical shift changes of $^{15}$N-MCL-1ΔNΔC upon MIM1 titration up to a ratio of 2:1 MIM1:MCL-1 are plotted as a function of MCL-1ΔNΔC residue. Affected residues are represented as purple bars in the plot (calculated significance threshold >0.0197 p.p.m.). Residues with significant backbone amide chemical shift changes (purple) are concentrated in a subregion of the canonical BH3-binding pocket (green). Of note, MCL-1ΔNΔC residues M250, V253, F254, S255, D256, G257, G262, and R263 are unassigned.

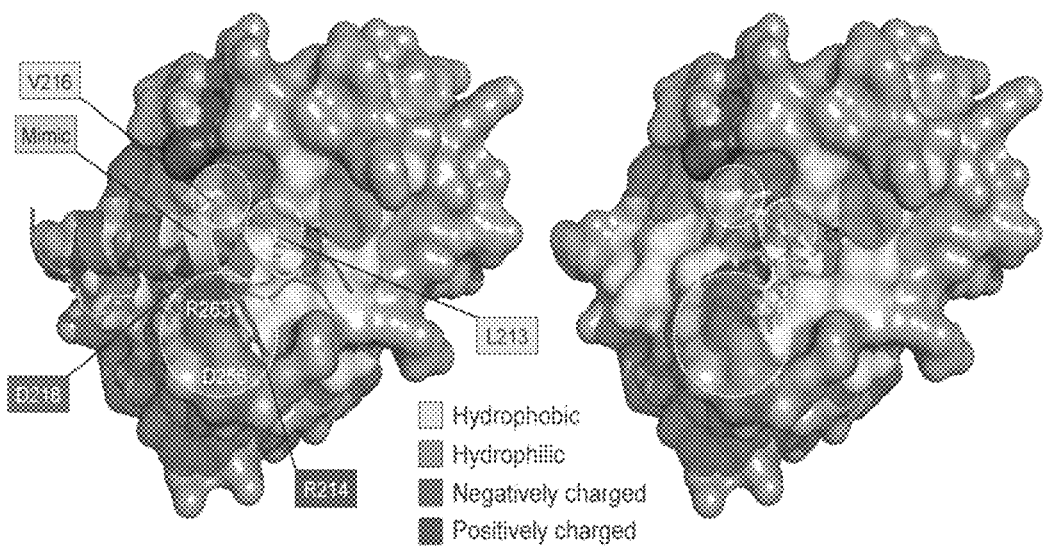

Figure 8. Molecular Docking of MIM1 on MCL-1ΔNΔC. The docked structure of MIM1 at the canonical BH3-binding pocket of MCL-1ΔNΔC predicts that (1) the cyclohexyl group makes complementary hydrophobic contacts with the region of the protein interface flanked by MCL-1 SAHB$_D$ residues L213 and V216, (2) the thiazolyl core and its methyl substituent points directly into a deep crevice occupied by MCL-1 SAHB$_D$ L213 in the stapled peptide/protein complex, and (3) the benzene-1,2,3-triol (or pyrogallol) moiety engages in hydrophilic contacts with D256 and R263, two charged MCL-1 residues implicated in complementary electrostatic interactions with R214 and D218 of MCL-1 SAHB$_D$.

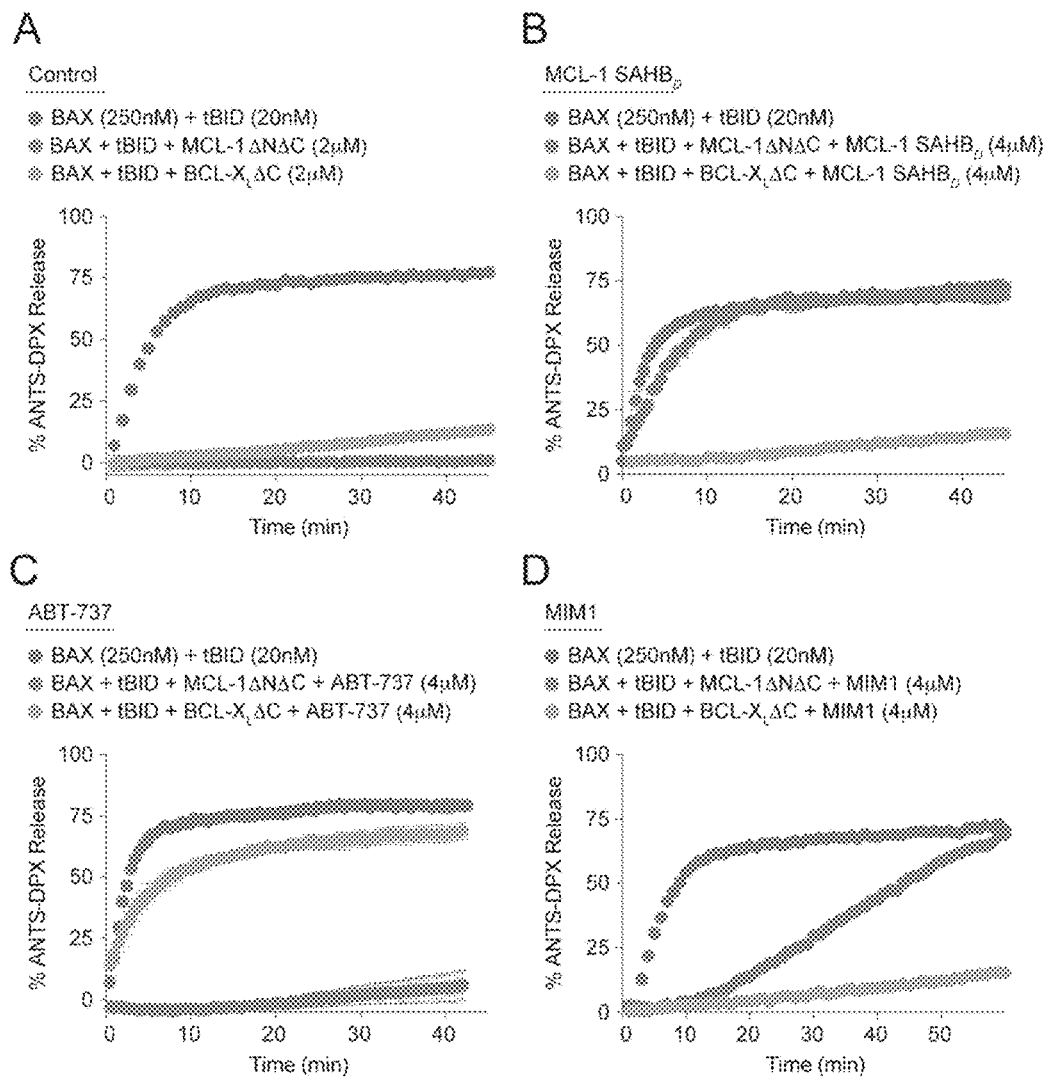

Figure 9. Selective Blockade of MCL-1-mediated Suppression of BAX activation by MIM1. (A) BH3-only protein tBID directly activates BAX-mediated liposomal release, which is effectively suppressed by treatment with anti-apoptotic MCL-1⊠N⊠C and BCL-X$_L$⊠C. (B) MCL-1 SAHB$_D$ selectively inhibits MCL-1⊠N⊠C suppression of tBID-induced BAX activation. (C) ABT-737 selectively inhibits BCL-X$_L$⊠C suppression of tBID-induced BAX activation.
(D) The activity profile of MIM1 in the liposomal release assay mirrors the MCL-1 selectivity of MCL-1 SAHB$_D$. Liposomal assays were conducted in triplicate for each condition using two independent preparations of recombinant BAX with similar results.

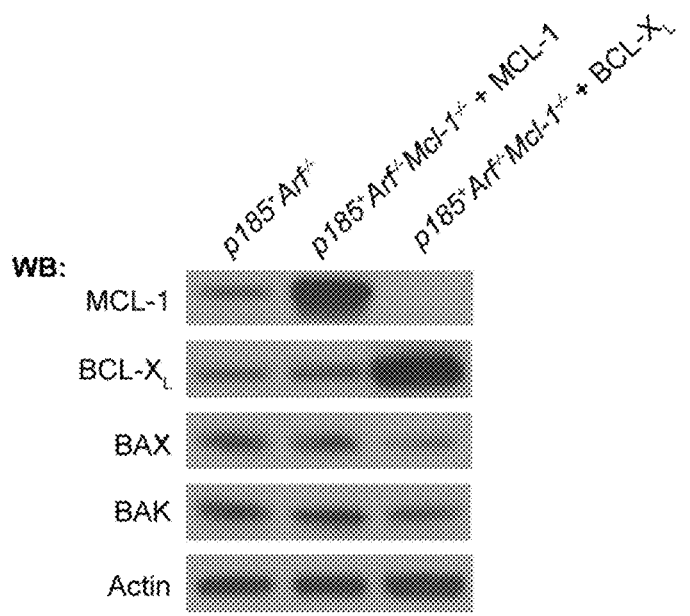

Figure 10. Western Blot Analysis of Genetically-defined $p185^+Arf^{-/-}$ Cells.
Whereas the parental $p185^+Arf^{-/-}$ CML cells express both MCL-1 and BCL-$X_L$, MCL-1- and BCL-$X_L$-rescued $p185^+Arf^{-/-}Mcl-1^{-/-}$ cells demonstrate overexpression of MCL-1 or BCL-$X_L$, respectively. The pro-apoptotic effectors BAX and BAK are expressed at similar levels in all three cell lines.

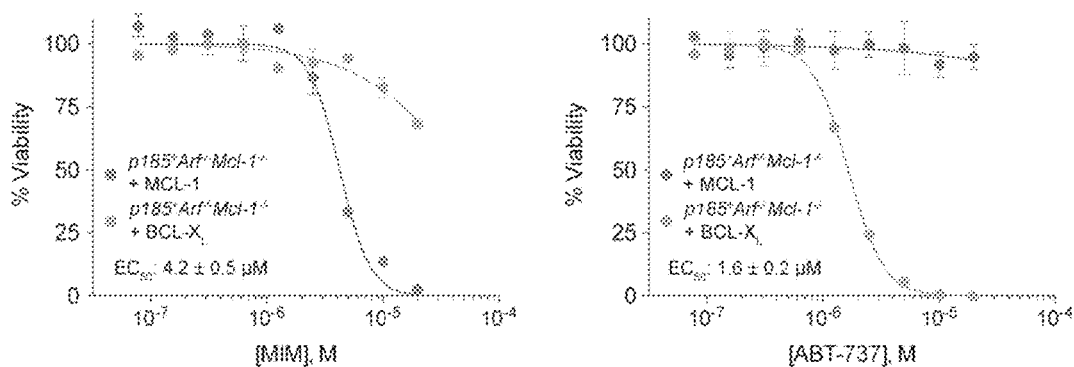

Figure 11. MIM1 Selectively Impairs the Viability of MCL-1-dependent Leukemia Cells. MIM1 dose-responsively induces cell death of $p185^+Arf^{-/-}Mcl-1^{-/-}$ CML cells rescued by overexpression of MCL-1, but not BCL-$X_L$, whereas ABT-737 has the opposite activity profile, as measured by CellTiter-Glo assay at 24 h. Data are mean ± SEM for experiments performed in duplicate, normalized to vehicle control, and repeated at least twice with independent cell cultures.

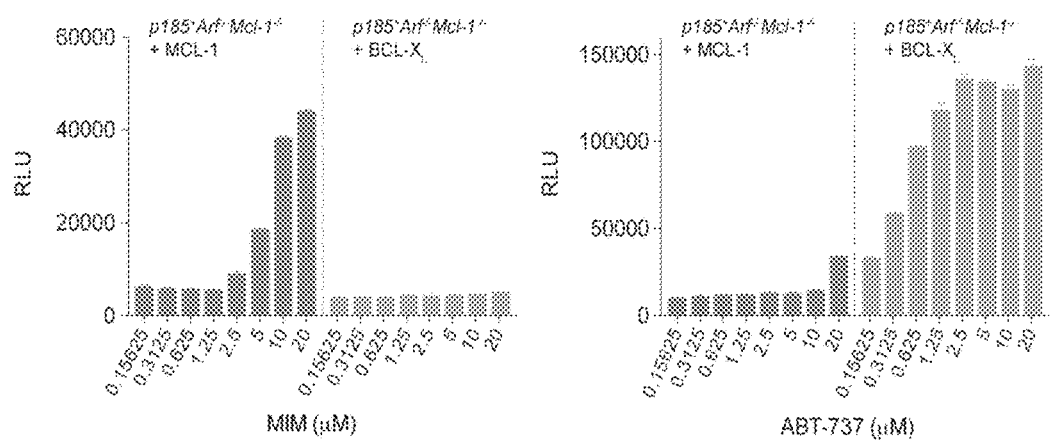

Figure 12. MIM1 Selectively Activates Caspase 3/7 in MCL-1-dependent Leukemia Cells. The selective cytotoxic effects of MIM1 and ABT-737 are accompanied by dose-responsive caspase 3/7 activation in the respective MCL-1 or BCL-X$_L$-rescued $p185^+Arf^{-/-}Mcl-1^{-/-}$ leukemia cell lines, as measured at 8 h post-treatment. Data are mean ± SEM for experiments performed in duplicate, normalized to vehicle control, and repeated at least twice with independent cell cultures.

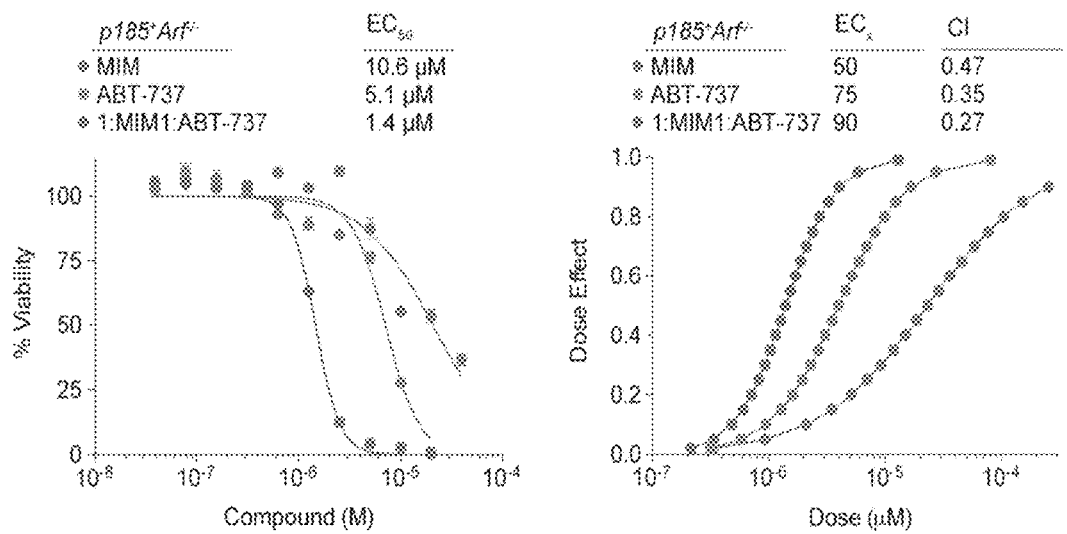

Figure 13. Synergy of MIM1 and ABT-737 in the Context of Dual MCL-1 and BCL-$X_L$ Expression. Combination treatment with MIM1 and ABT-737 induces synergistic killing of parental $p185^+Arf^{-/-}$ CML cells that express both MCL-1 and BCL-$X_L$, as reflected by a leftward shift of the viability isotherm and the CalcuSyn dose effect curve, with calculated CI values of <1 at $ED_{50}$, $ED_{75}$, and $ED_{90}$. CI, combination index; ED, effective dose.

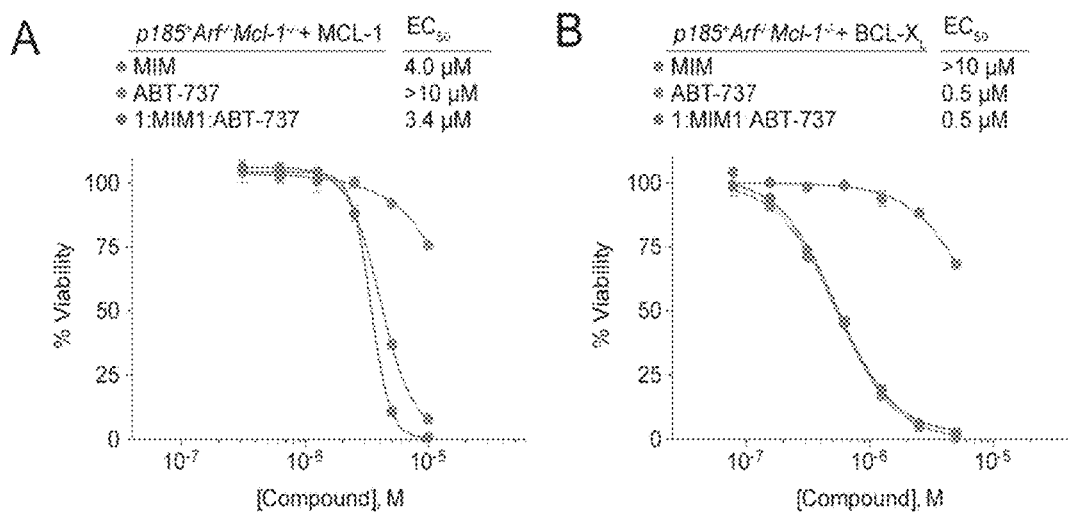

Figure 14. MIM1/ABT-737 Synergy is Dependent on the Co-expression of MCL-1 and BCL-$X_L$, and thus does not Manifest in the Context of Exclusive MCL-1 or BCL-$X_L$ expression. (A) The addition of ABT-737 to MIM1 treatment of MCL-1-rescued $p185^+Arf^{-/-}Mcl-1^{-/-}$ CML cells had little to no additional cytotoxic effect, consistent with the relative inactivity of ABT-737 in the context of MCL-1-dependence. (B) Correspondingly, the addition of MIM1 to ABT-737 treatment of BCL-$X_L$-rescued $p185^+Arf^{-/-}Mcl-1^{-/-}$ CML cells provided no additional cytotoxic effect, consistent with the relative inactivity of MIM1 in the context of BCL-$X_L$-dependence. Data are mean ± SEM for experiments performed in duplicate, normalized to vehicle control, and repeated at least twice with independent cell cultures.

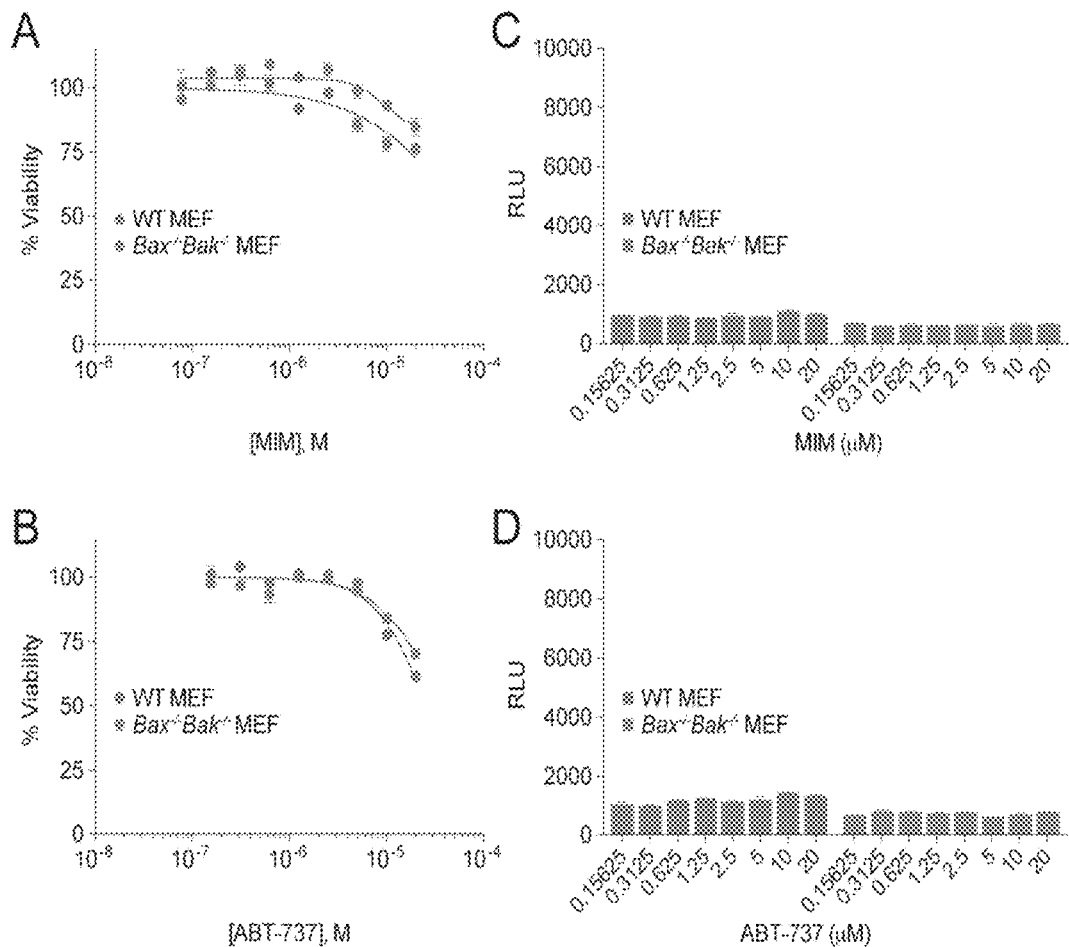

Figure 15. Effect of MIM1 and ABT-737 on Mouse Embryonic Fibroblasts (MEFs). MIM1 and ABT-737 manifest little to no cytotoxicity (24 h) (A, B) or caspase 3/7 activation (8 h) (C, D) in wild-type or $Bax^{-/-}Bak^{-/-}$ MEFs, suggesting the potential of a therapeutic window for MIM1. Data are mean ± SEM for experiments performed in duplicate and repeated at least twice with independent cell cultures with similar results.

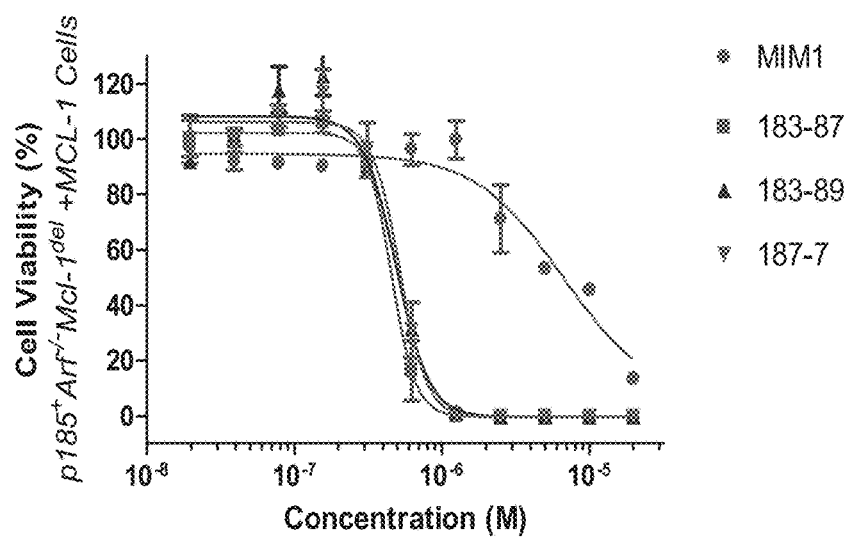
FIG 17. A series of MIM1 analogs with optimized MCL-1 binding activity likewise demonstrate enhanced anti-leukemic activity compared to MIM1 in an MCL-1-dependent context.

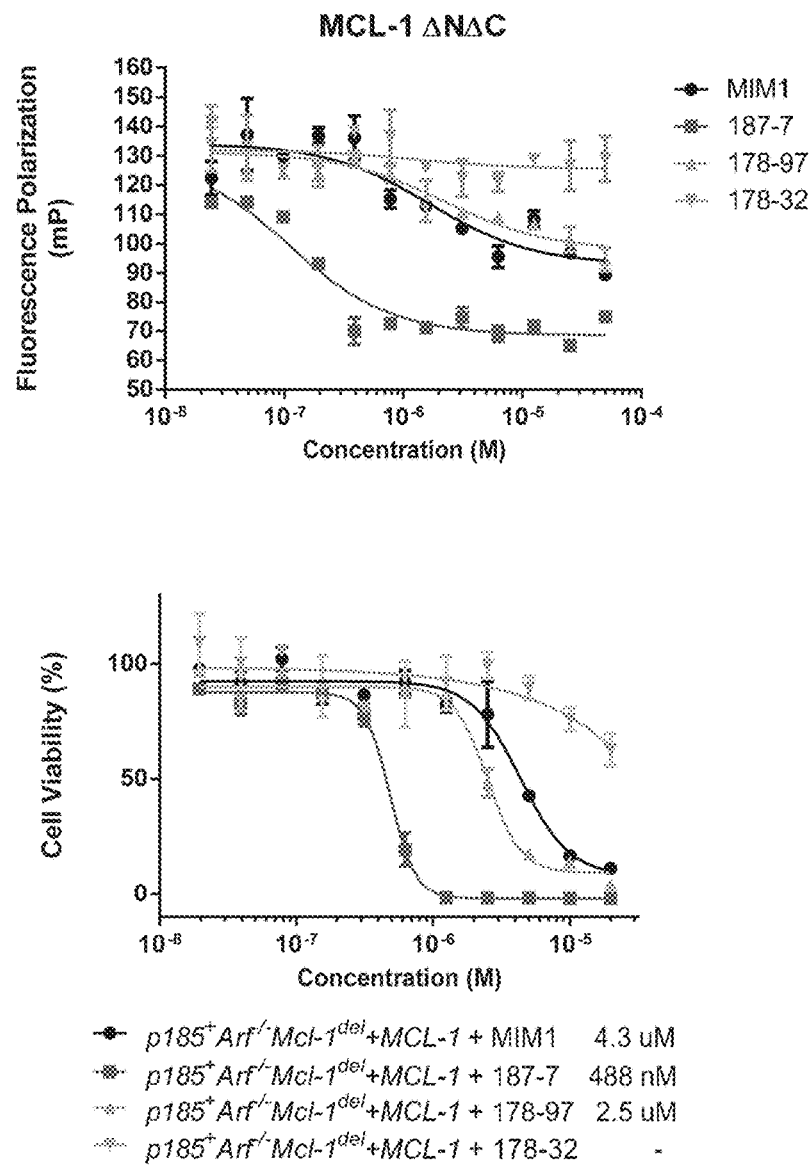
FIG 18. The MCL-1 binding activity of variably potent MCL-1 inhibitor molecules (top) correlates with the degree of cytotoxicity observed in MCL-1-dependent leukemia cells (bottom).

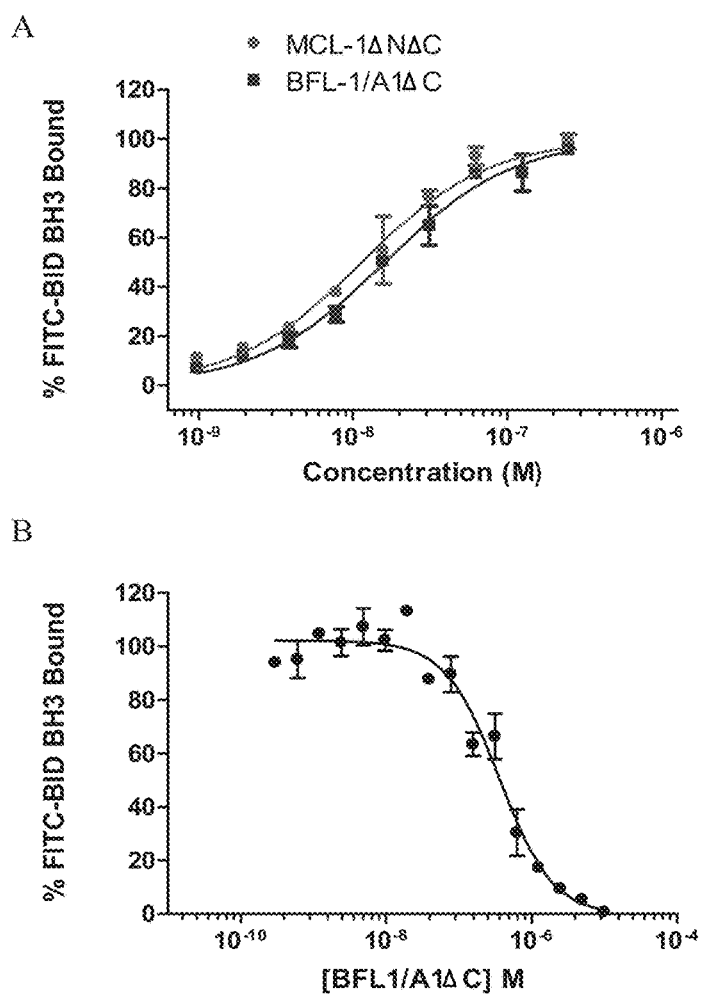

FIG 19. Potent targeting of the anti-apoptotic protein BFL-1/A1 by MIM1. (A) FITC-BID BH3 directly binds to MCL-1ΔNΔC and BFL-1/A1ΔC with similar binding affinity. Thus, the complex between FITC-BID BH3 and BFL-1/A1ΔC was employed in a competitive FP assay to monitor the capacity of MIM1 to target BFL-1/A1ΔC. (B) MIM1 manifests robust targeting of BFL1/A1ΔC, with effective competition in the nanomolar range.

| Compound ID | Molecular Structure | MCL-1 (IC50) | BFL-1/A1 (IC50) |
|---|---|---|---|
| CGDF-187-7 | 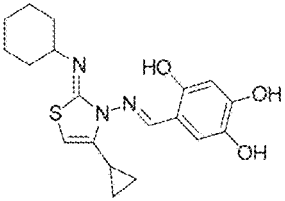 | 123 nM | 26 nM |
| CGDF-183-87 | 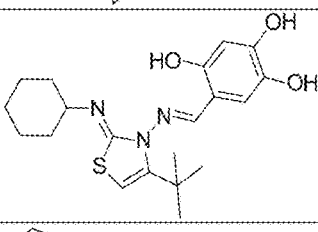 | 151 nM | 42 nM |
| CGDF-187-44 | 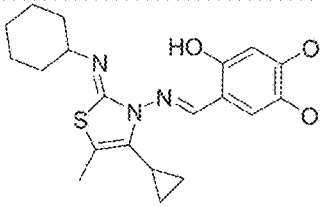 | 587 nM | 117 nM |
| CGDF-183-89 | 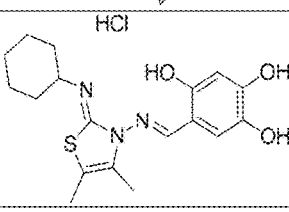 | 780 nM | 581 nM |
Fig. 20A: Dual MCL-1 and BFL-1/A1 Inhibitor Molecules

| Compound ID | Molecular Structure | MCL-1 (IC50) | BFL-1/A1 (IC50) |
|---|---|---|---|
| CGDF-183-20 | 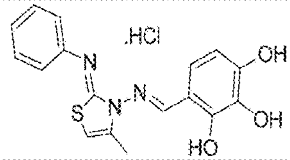 | ND | 264 nM |
| CGDF-183-84 | 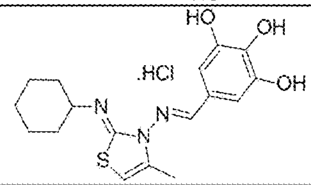 | 13 µM | 316 nM |
| CGDF-190-20 | 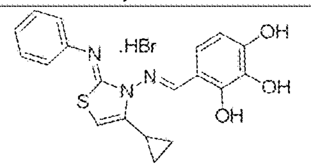 | ND | 365 nM |
| CGDF-183-91 | 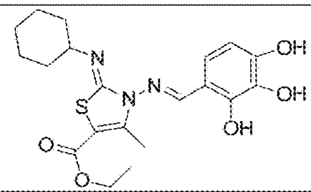 | 11.8 µM | 381 nM |
| CGDF-183-76 | 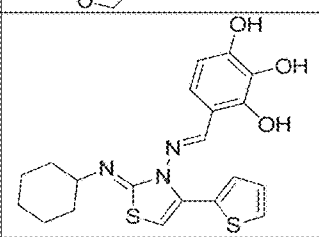 | 11 µM | 388 nM |
| CGDF-187-58 | 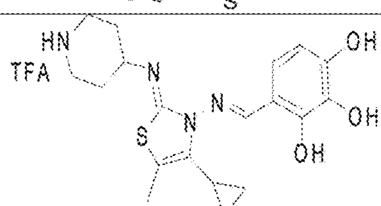 | ND | 689 nM |

FIG 20B. Selective BFL-1/A1 Inhibitor Molecules

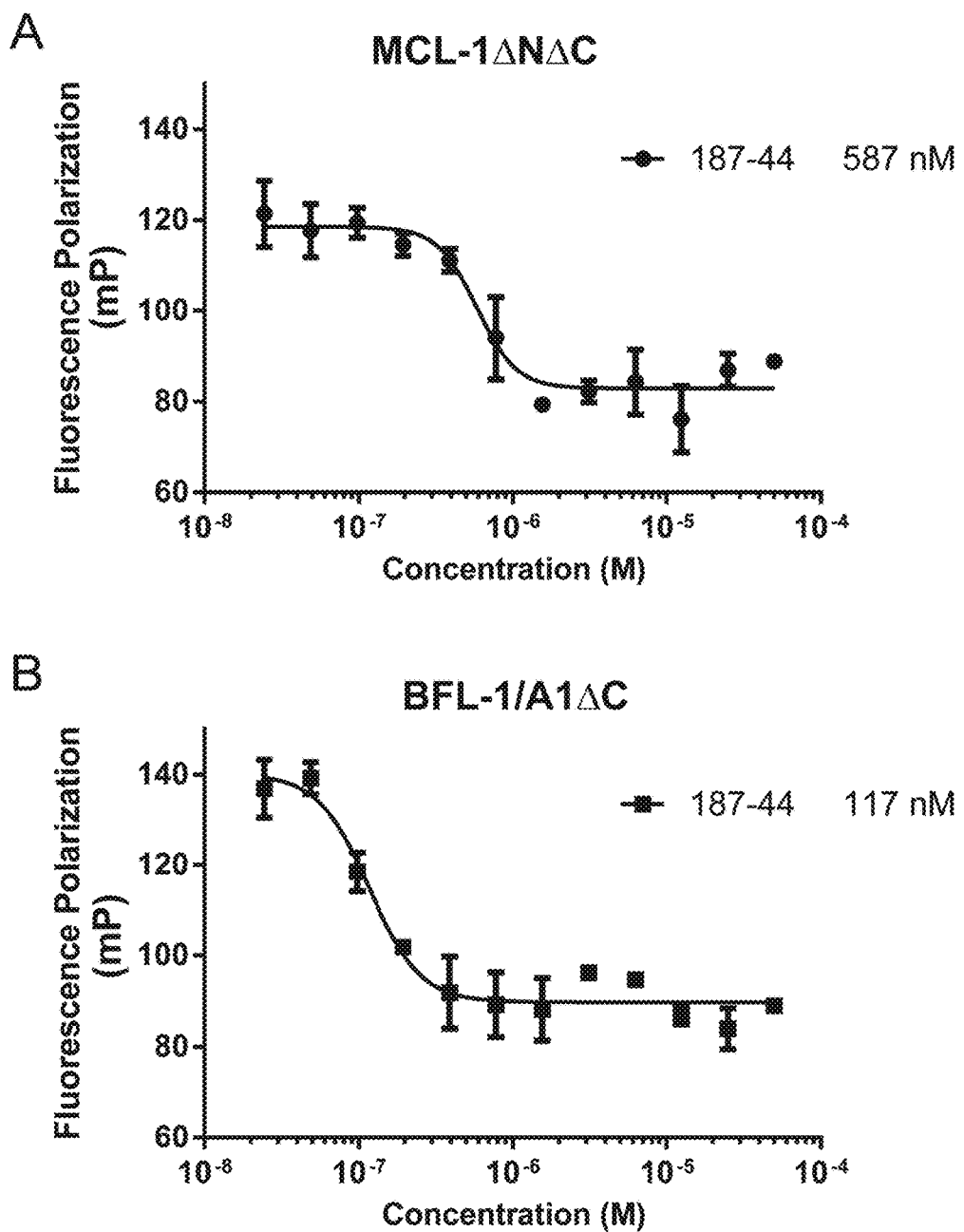
FIG 21. Select MIM1 analogs manifest high affinity competitive binding activity toward both BFL-1/A1ΔC (A) and MCL-1ΔNΔC (B), providing examples of inhibitors with dual specificity.

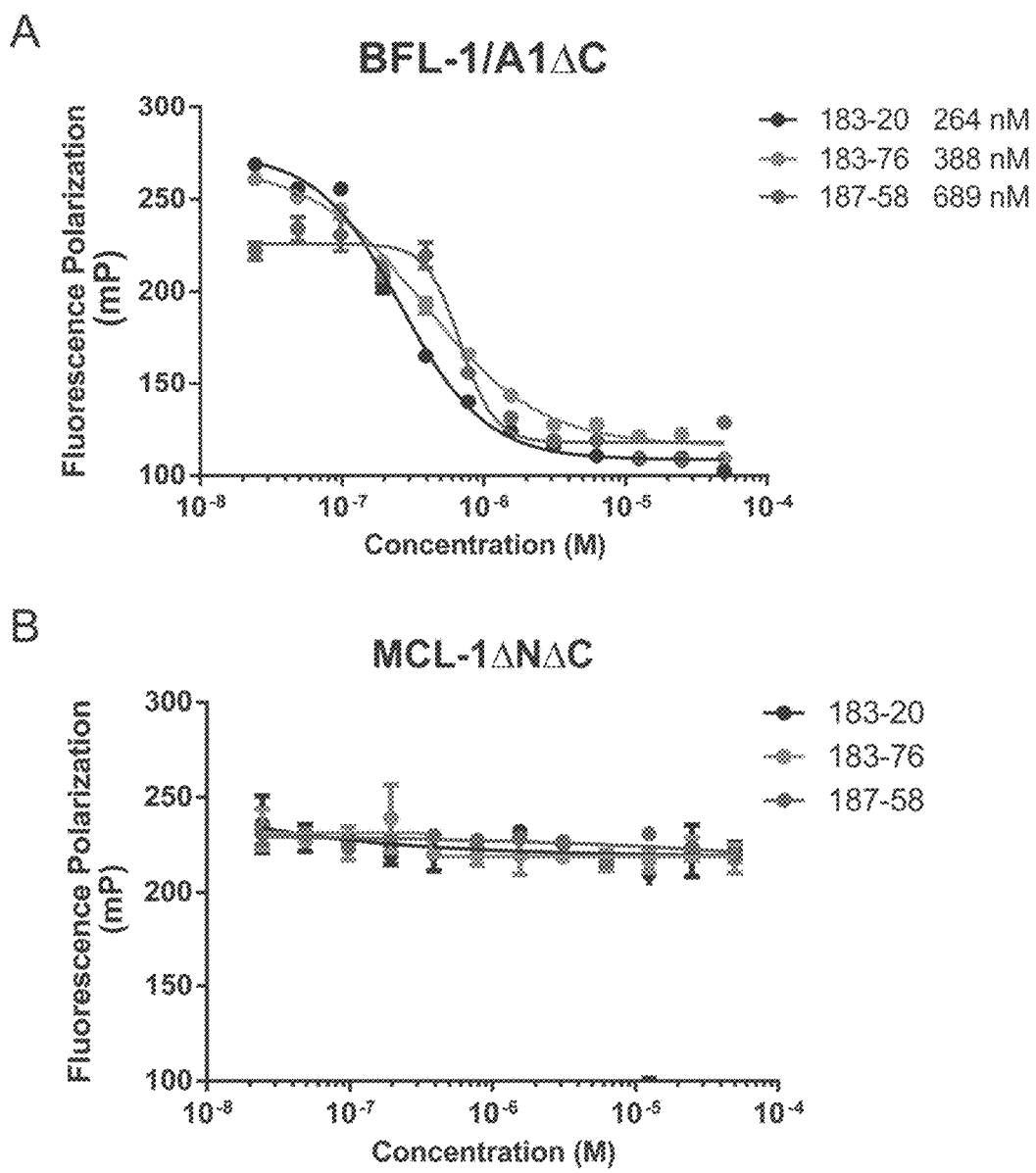
FIG 22. Select MIM1 analogs manifest high affinity competitive binding activity toward BFL-1/A1ΔC (A), but little to no interaction with MCL-1ΔNΔC (B), providing examples of selective BFL-1/A1 inhibitors.

SEQUENCE LISTING

```
<160> NUMBER OF SEQ ID NOS: 6

<210> SEQ ID NO 1
<211> LENGTH: 19
<212> TYPE: PRT
<213> ORGANISM: Artificial Sequence
<220> FEATURE:
<223> OTHER INFORMATION: synthetically generated peptide

<400> SEQUENCE: 1

Lys Ala Leu Glu Thr Leu Arg Val Gly Asp Val Gln Arg Asn His Glu
 1               5                  10                  15

Thr Ala Phe

<210> SEQ ID NO 2
<211> LENGTH: 19
<212> TYPE: PRT
<213> ORGANISM: Artificial Sequence
<220> FEATURE:
<223> OTHER INFORMATION: synthetically generated peptide

<400> SEQUENCE: 2

Lys Ala Leu Glu Thr Leu Arg Arg Val Gly Asp Gly Val Arg Asn His
 1               5                  10                  15

Thr Ala Phe

<210> SEQ ID NO 3
<211> LENGTH: 19
<212> TYPE: PRT
<213> ORGANISM: Artificial Sequence
```

```
<220> FEATURE:
<223> OTHER INFORMATION: synthetically generated peptide

<400> SEQUENCE: 3

Lys Ala Leu Glu Thr Leu Arg Arg Val Gly Asp Gly Val Arg Asn His
1               5                   10                  15

Thr Ala Phe

<210> SEQ ID NO 4
<211> LENGTH: 23
<212> TYPE: PRT
<213> ORGANISM: Artificial Sequence
<220> FEATURE:
<223> OTHER INFORMATION: synthetically generated peptide

<400> SEQUENCE: 4

Asn Leu Trp Ala Ala Gln Arg Tyr Gly Arg Glu Leu Arg Asx Ser Asp
1               5                   10                  15

Phe Val Asp Ser Phe Lys Lys
            20

<210> SEQ ID NO 5
<211> LENGTH: 19
<212> TYPE: PRT
<213> ORGANISM: Artificial Sequence
<220> FEATURE:
<223> OTHER INFORMATION: synthetically generated peptide

<400> SEQUENCE: 5

Asp Ile Ile Arg Asn Ile Ala Arg His Leu Ala Val Gly Asp Asx Asp
1               5                   10                  15

Arg Ser Ile

<210> SEQ ID NO 6
<211> LENGTH: 15
<212> TYPE: PRT
<213> ORGANISM: Artificial Sequence
<220> FEATURE:
<223> OTHER INFORMATION: synthetically generated peptide

<400> SEQUENCE: 6

Val Val His Leu Thr Leu Arg Ala Gly Asp Phe Ser Arg Arg Tyr
1               5                   10                  15
```

INHIBITION OF MCL-1 AND/OR BFL-1/A1

CROSS REFERENCE TO RELATED APPLICATIONS

This application claims the benefit of U.S. Provisional Application No. 61/613,225, filed on Mar. 20, 2012, which is incorporated herein by reference in its entirety.

STATEMENT REGARDING FEDERALLY SPONSORED RESEARCH OR DEVELOPMENT

This invention was made with government support under grant number CA092625 awarded by The National Institutes of Health. The government has certain rights in the invention.

TECHNICAL FIELD

This disclosure features compounds and pharmaceutically acceptable salts thereof that inhibit MCL-1 and/or BFL-1/A1 and compositions and combinations containing the same as well as methods of using the same.

BACKGROUND

BCL-2 is the founding member of a family of anti- and pro-apoptotic proteins that form an interaction network to regulate the critical homeostatic balance between cellular life and death[1,2]. The original discovery of BCL-2 at the t(14;18) chromosomal breakpoint of follicular lymphoma expanded the paradigm for cancer pathogenesis to include the inability to undergo programmed cell death[3-5]. The pathologic overexpression of anti-apoptotic BCL-2 and its functional homologues BCL-$X_L$, BCL-w, MCL-1, and BFL-1/A1 has emerged as a causative mechanism for the development, maintenance, and chemoresistance of many human cancers[6,7].

The anti-apoptotic proteins contain a surface groove that can bind and sequester—with differential potency and specificity—the BH3 death domains of pro-apoptotic members[8,9]. BH3-only pro-apoptotics such as BID and BIM contain a single BH3 domain and function as afferent sensors of cellular stress, delivering their death message to the "multidomain" anti- and pro-apoptotic members, which regulate the cellular life-death decision at the level of the mitochondrion[10]. When activated directly by BH3-only interaction and/or indirectly by BH3-only-mediated competitive displacement from anti-apoptotics, the multidomain pro-apoptotic proteins BAX and BAK undergo a monomer-to-oligomer transformation that results in outer mitochondrial membrane poration and release of apoptogenic factors[11]. Whereas cancer cells deploy the anti-apoptotic proteins to silence this pro-apoptotic pathway, pharmacologic antagonists of anti-apoptotic proteins hold promise to restore the death pathway in cancer. Thus, a series of small molecule screens and structure-based methodologies were initially applied to target BCL-2, yielding an eclectic array of small molecules and peptides with various degrees of biochemical, cellular, and in vivo activity[12-21]. ABT-263 is an orally bioavailable and selective BCL-2/BCL-$X_L$ inhibitor, which is advancing through the clinical trials process, manifesting both safety and preliminary efficacy in BCL-2-dependent cancers[22-25].

Broad experimentation with the ABT-263 molecule and its progenitor ABT-737 revealed that expression of anti-apoptotic proteins lying outside their binding spectra caused resistance[26-29], compelling the development of alternative or complementary agents that would either harbor broader anti-apoptotic targeting capacity or inherent selectivity for anti-apoptotics like MCL-1 and BFL-1/A1 that evade ABT-263/737 antagonism. The small molecule obatoclax[15] and the peptidic Stabilized Alpha-Helix of BCL-2 domains (SAHBs) modeled after the BID and BIM BH3 domains[30-32] are examples of novel agents that more broadly target the BCL-2 family anti-apoptotic proteins.

WO 2011/094708 discloses small molecules that modulate MCL-1 and/or BFL-1/A1 and methods of using the same, as a single agent or in combination with other drugs, for modulating cell death, cell division, cell differentiation, and treating disorders, such as hyperproliferative disorders.

SUMMARY

I

This disclosure features compounds and pharmaceutically acceptable salts thereof that inhibit MCL-1 and/or BFL-1/A1 and compositions containing the same. This disclosure also features combinations that include one or more of the MCL-1/BFL-1/A1 inhibitor compounds described herein, or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the one or more therapeutic agents (as well as compositions containing the same).

Also featured are methods of using any one or more of such MCL-1 and/or BFL-1/A1 inhibitor compounds, salts, combinations, and compositions, alone or in combination with other drugs e.g., for the treatment or prevention of diseases, disorders, and conditions associated with deregulated apoptosis of cells (e.g., diseased or damaged cells; e.g., insufficient apoptosis of diseased or damaged cells or reduced apoptosis of diseased or damaged cells) and/or other cancer treatment therapies (e.g., surgery, radiation).

In one aspect, this disclosure features combinations that include one or more compounds of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737); or (where applicable) a pharmaceutically acceptable salt of the one or more therapeutic agents (as well as compositions containing the same).

Compounds of formula (I) have the following formula:

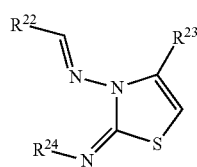

(I)

in which:

$R^{22}$ is aryl, heteroaryl, cycloalkyl, heterocycloalkyl; each of which is optionally substituted with from 1-5 (e.g., 1-3) independently selected Z;

$R^{23}$ is $C_1$-$C_8$ alkyl, $C_1$-$C_8$ haloalkyl $C_2$-$C_8$ alkenyl, $C_2$-$C_8$ alkynyl, $C_1$-$C_6$ alkoxy, or $C_1$-$C_6$ haloalkoxy; or substituted or unsubstituted aryl, substituted or unsubstituted heteroaryl, substituted or unsubstituted cycloalkyl, or substituted or unsubstituted heterocycloalkyl wherein when $R^{23}$ is substituted, it is substituted with from 1-5 (e.g., 1-3) independently selected Z; and $R^{24}$ is $C_1$-$C_8$ alkyl, $C_1$-$C_8$ haloalkyl $C_2$-$C_8$ alkenyl, $C_2$-$C_8$ alkynyl, $C_1$-$C_6$ alkoxy, or $C_1$-$C_6$ haloalkoxy; or substituted or unsubstituted aryl, substituted or unsubstituted heteroaryl, substituted or unsubstituted cycloalkyl, or substituted or unsubstituted heterocycloalkyl wherein when $R^{24}$ is substituted, it is substituted with from 1-5 (e.g., 1-3) independently selected Z; and each occurrence of Z is independently halogen; hydroxyl; oxo (except when $R^{22}$-$R^{24}$ is aromatic); $C_1$-$C_8$ alkyl; $C_1$-$C_8$ haloalkyl; $C_2$-$C_8$ alkenyl; $C_2$-$C_8$ alkynyl; $C_1$-$C_6$ alkoxy; $C_1$-$C_6$ haloalkoxy; or phenyl, heteroaryl, cycloalkyl, or heterocycloalkyl. Each of which is optionally substituted with from 1-3 substituents independently selected from halogen; hydroxyl; oxo (except when $R^{22}$-$R^{24}$ is aromatic); $C_1$-$C_8$ alkyl; $C_1$-$C_8$ haloalkyl; $C_2$-$C_8$ alkenyl; $C_2$-$C_8$ alkynyl; $C_1$-$C_6$ alkoxy; $C_1$-$C_6$ haloalkoxy.

Compounds of formula (II) have the following formula:

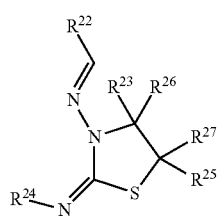

(II)

wherein:

$R^{22}$ is:

(i) $C_6$-$C_{10}$ aryl, which is optionally substituted with from 1-5 independently selected $R^a$;

(ii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^a$; or (iii) phenyl fused to $C_1$-$C_3$ alkylenedioxy, wherein the phenyl portion is optionally substituted with from 1-2 independently selected $R^a$;

$R^{23}$ is:

(i) $C_1$-$C_8$ alkyl or $C_1$-$C_8$ haloalkyl, each of which is optionally substituted with from 1-2 independently selected $R^b$;

(ii) phenyl that is optionally substituted with from independently selected 1-4 $R^c$;

(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 independently selected $R^c$;

(iv) $C_3$-$C_6$ cycloalkyl or $C_3$-$C_6$ cycloalkenyl, each of which is optionally substituted with from 1-4 independently selected $R^d$; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;

$R^{25}$ is:

(i) hydrogen;

(ii) $C_1$-$C_8$ alkyl or $C_1$-$C_8$ haloalkyl, each of which is optionally substituted with from 1-2 independently selected $R^b$;

(iii) $C_3$-$C_6$ cycloalkyl or $C_3$-$C_6$ cycloalkenyl, each of which is optionally substituted with from 1-4 independently selected $R^d$; or (iv) —C(O)O($C_1$-$C_6$ alkyl);

or $R^{23}$ and $R^{25}$, together with the carbon atoms to which each is attached, form:

(i) a 5-6 membered saturated or unsaturated carbocyclic ring, which is optionally substituted with from 1-4 independently selected $R^d$; or (ii) a 5-6 membered saturated or unsaturated hetrocyclic ring, which is optionally substituted with from 1-4 independently selected $R^d$, and wherein from 1-2 of the ring atoms (other than the two ring atoms attached to $R^{23}$ and $R^{24}$) is independently selected from N, NH, N($C_1$-$C_3$ alkyl), NC(O)($C_1$-$C_6$ alkyl), O, and S;

$R^{26}$ and $R^{27}$ together are a bond (form a second or double bond between the carbon atoms to which each is attached); or each of $R^{26}$ and $R^{27}$ is independently selected from hydrogen, halo, and hydroxyl;

$R^{24}$ is:

(i) $C_3$-$C_{10}$ cycloalkyl or $C_3$-$C_{10}$ cycloalkenyl, each of which is optionally substituted with from 1-4 independently selected $R^d$;

(ii) $C_6$-$C_{10}$ aryl, which is optionally substituted with from 1-5 independently selected $R^c$;

(iii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^c$;

(iv) unsubstituted $C_1$-$C_8$ alkyl or unsubstituted $C_1$-$C_8$ haloalkyl;

(v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;

(vi) ($C_1$-$C_6$ alkyl)-($C_3$-$C_8$ cycloalkyl), wherein the cycloalkyl portion is optionally substituted with from 1-4 independently selected $R^d$; or (vii) dihydronaphthyl, tetrahydronaphthyl, indanyl, or indenyl;

$R^a$ at each occurrence is, independently, selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)H;

—C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); and —SO$_2$N(C$_1$-C$_6$ alkyl)$_2$;

R$^b$ at each occurrence is, independently, selected from hydroxyl, C$_1$-C$_6$ alkoxy; C$_1$-C$_6$ thioalkoxy; C$_1$-C$_6$ haloalkoxy; C$_1$-C$_6$ thiohaloalkoxy; —NH$_2$; —NH(C$_1$-C$_6$ alkyl); N(C$_1$-C$_6$ alkyl)$_2$; —NHC(O)(C$_1$-C$_6$ alkyl); cyano; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); and —SO$_2$N(C$_1$-C$_6$ alkyl)$_2$;

R$^c$ at each occurrence is, independently, selected from any one the substituents delineated collectively in (a), (b), (c), and (d) below:

(a) C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, C$_1$-C$_6$ haloalkyl, —NH(C$_1$-C$_6$ alkyl), N(C$_1$-C$_6$ alkyl)$_2$, or —NHC(O)(C$_1$-C$_6$ alkyl), each of which is optionally substituted with —OH, C$_1$-C$_6$ alkoxy, —NH$_2$, or —SH;

(b) halo; —OH; —CN; nitro; —NH$_2$; azido; C$_2$-C$_4$ alkenyl; C$_2$-C$_4$ alkynyl; —C(O)H; —C(O)(C$_1$-C$_6$ alkyl); C(O)OH; —C(O)O(C$_1$-C$_6$ alkyl); —OC(O)(C$_1$-C$_6$ alkyl); —SO$_2$(C$_1$-C$_6$ alkyl); —SO$_2$(C$_1$-C$_6$ haloalkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$; —NHCO(C$_1$-C$_6$ alkyl), —NHSO$_2$(C$_1$-C$_6$ alkyl); —C(O)O—(CH$_2$)$_{1-3(e.g., 1)}$—C(O)-(phenyl optionally substituted as defined in (d) below (e.g., —C(O)O—CH$_2$—C(O)-(phenyl);

(c) L-C$_3$-C$_8$ cycloalkyl, C$_3$-C$_6$ cycloalkoxy, or L-heterocyclyl containing from 5-7 ring atoms, wherein from 1-2 of the ring atoms of the heterocyclyl is independently selected from N, NH, N(C$_1$-C$_6$ alkyl), NC(O)(C$_1$-C$_6$ alkyl), NC(O)O(C$_1$-C$_6$ alkyl), O, and S; and each of said ring systems is optionally substituted with from 1-3 independently selected C$_1$-C$_4$ alkyl groups; and wherein L is a bond or C$_1$-C$_6$ alkylene; and (d) phenyl, —O-(phenyl), or heteroaryl containing from 5-6 ring atoms, wherein from 1-2 of the ring atoms of the heteroaryl is independently selected from N, NH, N(C$_1$-C$_3$ alkyl), O, and S; wherein each of said phenyl and heteroaryl is optionally substituted with from 1-3 substituents independently selected from halo; hydroxyl; cyano; —C(O)(C$_1$-C$_6$ alkyl); C(O)OH; —C(O)O(C$_1$-C$_6$ alkyl); nitro; —NH$_2$; —NH(C$_1$-C$_6$ alkyl), N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl, wherein said alkyl or alkyl portion is optionally substituted with —OH, —NH$_2$, or —SH;

R$^d$ at each occurrence is, independently, selected from any one the substituents delineated collectively in (a) and (b) below:

(a) C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, C$_1$-C$_6$ haloalkyl, —NH(C$_1$-C$_6$ alkyl), N(C$_1$-C$_6$ alkyl)$_2$, or —NHC(O)(C$_1$-C$_6$ alkyl), each of which is optionally substituted with —OH, C$_1$-C$_6$ alkoxy, —NH$_2$, or —SH; or (b) halo; —OH; —CN; nitro; —NH$_2$; azido; C$_2$-C$_4$ alkenyl; C$_2$-C$_4$ alkynyl; —C(O)H; —C(O)(C$_1$-C$_6$ alkyl); C(O)OH; —C(O)O(C$_1$-C$_6$ alkyl); —OC(O)(C$_1$-C$_6$ alkyl); —SO$_2$(C$_1$-C$_6$ alkyl); —SO$_2$(C$_1$-C$_6$ haloalkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$; —NHCO(C$_1$-C$_6$ alkyl), —NHSO$_2$(C$_1$-C$_6$ alkyl).

In some embodiments, it is provided when R$^{25}$ is hydrogen, and R$^{26}$ and R$^{27}$ together are a bond, then one, or more, or all of the following apply:

(1) R$^{24}$ cannot be unsubstituted cyclohexyl when R$^{22}$ is 2,3,4-trihydroxyphenyl, and R$^{23}$ is CH$_3$;

(2) R$^{24}$ cannot be 4-fluorophenyl when R$^{22}$ is 3,4-dihydroxyphenyl, and R$^{23}$ is 2H-benzo[b][1,4]oxazinyl-3 (4H)-onyl;

(3) R$^{24}$ cannot be 2,4-difluorophenyl when R$^{22}$ is 2,4-dihydroxyphenyl, and R$^{23}$ is furyl;

(4) R$^{24}$ cannot be 3-pyridyl when R$^{22}$ is 2,4-dihydroxyphenyl, and R$^{23}$ is furyl;

(5) when R$^{22}$ is 2,3,4-trihydroxyphenyl, then: R$^{24}$ cannot be CH$_3$ when R$^{23}$ is CH$_3$, 3,4-dimethylphenyl, 2-fluorophenyl, thienyl, or 3,4-dichlorophenyl; and R$^{24}$ cannot be n-propyl when R$^{23}$ is CH$_3$; and R$^{24}$ cannot be iso-propyl when R$^{23}$ is thienyl; and R$^{24}$ cannot be ethyl when R$^{23}$ is CH$_3$, (6) R$^{23}$ and R$^{24}$ cannot both be CH$_3$ when R$^{22}$ is 2,4-dihydroxyphenyl, 3,4-dihydroxyphenyl, 2-iodophenyl, 4-hydroxyphenyl, 4-cyanophenyl, or benzo[d][1,3]dioxolyl;

(7) R$^{23}$ cannot be 4-(difluoromethoxy)phenyl when R$^{22}$ is 4-hydroxyphenyl or 4-ethoxyphenyl, and R$^{24}$ is CH$_3$; and (8) R$^{23}$ cannot be 2-fluorophenyl or furyl when R$^{22}$ is 3,4-dihydroxyphenyl, and R$^{24}$ is CH$_3$.

In another aspect, compounds having formula (II), or a pharmaceutically acceptable salt thereof, are featured:

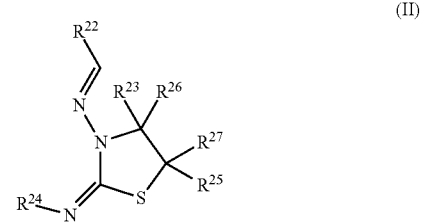

(II)

wherein:

R$^{22}$ is:

(i) C$_6$-C$_{10}$ aryl, which is optionally substituted with from 1-5 independently selected R$^a$;

(ii) heteroaryl, which contains from 5-10 ring atoms, wherein from 1-4 of the ring atoms is independently selected from N, NH, N(C$_1$-C$_3$ alkyl), O, and S; and wherein said heteroaryl ring is optionally substituted with from 1-4 independently selected R$^a$; or (iii) phenyl fused to C$_1$-C$_3$ alkylenedioxy, wherein the phenyl portion is optionally further substituted with from 1-2 independently selected R$^a$;

R$^{23}$ is:

(i) C$_3$-C$_6$ cycloalkyl or C$_3$-C$_6$ cycloalkenyl, each of which is optionally substituted with from 1-4 independently selected R$^d$;

(ii) branched C$_3$-C$_8$ alkyl or C$_1$-C$_8$ haloalkyl, each of which is optionally substituted with from 1-2 independently selected R$^b$; or (iii) heterocyclyl containing from 3-6 ring atoms, wherein from 1-2 of the ring atoms is independently selected from N, NH, N(C$_1$-C$_3$ alkyl), NC(O)(C$_1$-C$_6$ alkyl), O, and S; and wherein said heterocyclyl is optionally substituted with from 1-3 independently selected R$^d$;

R$^{25}$ is:

(i) hydrogen;

(ii) C$_1$-C$_8$ alkyl or C$_1$-C$_8$ haloalkyl, each of which is optionally substituted with from 1-2 independently selected R$^b$;

(iii) $C_3$-$C_6$ cycloalkyl or $C_3$-$C_6$ cycloalkenyl, each of which is optionally substituted with from 1-4 independently selected $R^d$; or (iv) —C(O)O($C_1$-$C_6$ alkyl);

$R^{26}$ and $R^{27}$ together are a bond (form a second or double bond between the carbon atoms to which each is attached);

$R^{24}$ is:

(i) $C_3$-$C_{10}$ cycloalkyl or $C_3$-$C_{10}$ cycloalkenyl, each of which is optionally substituted with from 1-4 independently selected $R^d$;

(ii) $C_6$-$C_{10}$ aryl, which is optionally substituted with from 1-5 independently selected $R^c$;

(iii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^c$;

(iv) unsubstituted $C_1$-$C_8$ alkyl or unsubstituted $C_1$-$C_8$ haloalkyl; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;

$R^a$ at each occurrence is, independently, selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;

$R^b$ at each occurrence is, independently, selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —NH$_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;

$R^c$ at each occurrence is, independently, selected from any one the substituents delineated collectively in (a), (b), (c), and (d) below:

(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —NH$_2$, or —SH;

(b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), —NHSO$_2$($C_1$-$C_6$ alkyl); —C(O)O—(CH$_2$)$_{1-3\ (e.g.,\ 1)}$—C(O)-(phenyl optionally substituted as defined in (d) below (e.g., —C(O)O—CH$_2$—C(O)-(phenyl);

(c) L-$C_3$-$C_8$ cycloalkyl, $C_3$-$C_6$ cycloalkoxy, or L-heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of said ring systems is optionally substituted with from 1-3 independently selected $C_1$-$C_4$ alkyl groups; and wherein L is a bond or $C_1$-$C_6$ alkylene; and (d) phenyl, —O-(phenyl), or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —NH$_2$, or —SH; and $R^d$ at each occurrence is, independently, selected from any one the substituents delineated collectively in (a) and (b) below:

(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —NH$_2$, or —SH; or (b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), —NHSO$_2$($C_1$-$C_6$ alkyl).

In a further aspect, compounds having formula (II), or a pharmaceutically acceptable salt thereof, are featured:

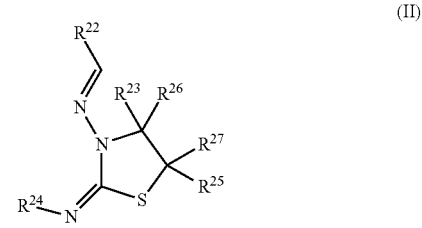

(II)

wherein:

$R^{22}$ is:

(i) $C_6$-$C_{10}$ aryl, which is optionally substituted with from 1-5 independently selected $R^a$;

(ii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^a$; or (iii) phenyl fused to $C_1$-$C_3$ alkylenedioxy, wherein the phenyl portion is optionally substituted with from 1-2 independently selected $R^a$;

$R^{23}$ is:

(i) $C_1$-$C_8$ alkyl or $C_1$-$C_8$ haloalkyl, each of which is optionally substituted with from 1-2 independently selected $R^b$;

(ii) phenyl that is optionally substituted with from independently selected 1-4 $R^c$;

(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from independently selected 1-3 $R^c$; or (iv) $C_3$-$C_6$ cycloalkyl or $C_3$-$C_6$ cycloalkenyl, each of which is optionally substituted with from 1-4 independently selected $R^d$; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;

$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl);

$R^{26}$ and $R^{27}$ together are a bond (form a second or double bond between the carbon atoms to which each is attached);

$R^{24}$ is:
(i) $C_3$-$C_{10}$ cycloalkyl or $C_3$-$C_{10}$ cycloalkenyl, each of which is optionally substituted with from 1-4 independently selected $R^d$; or
(ii) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;

$R^a$ at each occurrence is, independently, selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); and —$SO_2$N($C_1$-$C_6$ alkyl)$_2$;

$R^b$ at each occurrence is, independently, selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —$NH_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); and —$SO_2$N($C_1$-$C_6$ alkyl)$_2$;

$R^c$ at each occurrence is, independently, selected from any one the substituents delineated collectively in (a), (b), (c), and (d) below:
(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —$NH_2$, or —SH;
(b) halo; —OH; —CN; nitro; —$NH_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —$SO_2$($C_1$-$C_6$ alkyl); —$SO_2$($C_1$-$C_6$ haloalkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; —NHCO($C_1$-$C_6$ alkyl), —$NHSO_2$($C_1$-$C_6$ alkyl); —C(O)O—($CH_2$)$_{1-3(e.g., 1)}$—C(O)-(phenyl optionally substituted as defined in (d) below (e.g., —C(O)O—$CH_2$—C(O)-(phenyl);
(c) L-$C_3$-$C_8$ cycloalkyl, $C_3$-$C_6$ cycloalkoxy, or L-heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of said ring systems is optionally substituted with from 1-3 independently selected $C_1$-$C_4$ alkyl groups; and wherein L is a bond or $C_1$-$C_6$ alkylene; and
(d) phenyl, —O-(phenyl), or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —$NH_2$, or —SH;

$R^d$ at each occurrence is, independently, selected from any one the substituents delineated collectively in (a) and (b) below:
(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —$NH_2$, or —SH; or
(b) halo; —OH; —CN; nitro; —$NH_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —$SO_2$($C_1$-$C_6$ alkyl); —$SO_2$($C_1$-$C_6$ haloalkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH($C_1$-$C_6$ alkyl); —$SO_2$N($C_1$-$C_6$ alkyl)$_2$; —NHCO($C_1$-$C_6$ alkyl), —$NHSO_2$($C_1$-$C_6$ alkyl).

In some embodiments, it is provided when $R^{25}$ is hydrogen, $R^{24}$ cannot be unsubstituted cyclohexyl when $R^{22}$ is 2,3,4-trihydroxyphenyl, and $R^{23}$ is $CH_3$.

In still another aspect, compounds having formula (II), or a pharmaceutically acceptable salt thereof, are featured:

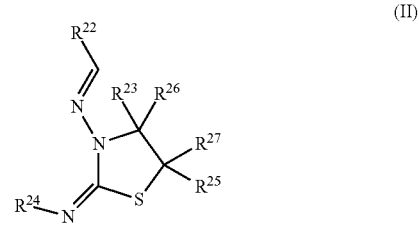

(II)

wherein:
$R^{22}$ is $C_6$-$C_{10}$ aryl, which is substituted with three hydroxyl groups and optionally further substituted with from 1-2 independently selected $R^a$;

$R^{23}$ is:
(i) $C_1$-$C_8$ alkyl or $C_1$-$C_8$ haloalkyl, each of which is optionally substituted with from 1-2 independently selected $R^b$;
(ii) phenyl that is optionally substituted with from independently selected 1-4 $R^c$;
(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from independently selected 1-3 $R^c$;
(iv) $C_3$-$C_6$ cycloalkyl or $C_3$-$C_6$ cycloalkenyl, each of which is optionally substituted with from 1-4 independently selected $R^d$; or
(v) heterocyclyl containing from 3-6 ring atoms, wherein from 1-2 of the ring atoms is independently selected from N, NH, N(C$_1$-C$_3$ alkyl), NC(O)(C$_1$-C$_6$ alkyl), O, and S; and wherein said heterocyclyl is optionally substituted with from 1-3 independently selected R$^d$;

R$^{25}$ is:
(i) hydrogen;
(ii) C$_1$-C$_8$ alkyl or C$_1$-C$_8$ haloalkyl, each of which is optionally substituted with from 1-2 independently selected R$^b$;
(iii) C$_3$-C$_6$ cycloalkyl or C$_3$-C$_6$ cycloalkenyl, each of which is optionally substituted with from 1-4 independently selected R$^d$; or
(iv) —C(O)O(C$_1$-C$_6$ alkyl);

R$^{26}$ and R$^{27}$ together are a bond (form a second or double bond between the carbon atoms to which each is attached);

R$^{24}$ is:
(i) C$_3$-C$_{10}$ cycloalkyl or C$_3$-C$_{10}$ cycloalkenyl, each of which is optionally substituted with from 1-4 independently selected R$^d$;
(ii) C$_6$-C$_{10}$ aryl, which is optionally substituted with from 1-5 independently selected R$^c$;
(iii) heteroaryl, which contains from 5-10 ring atoms, wherein from 1-4 of the ring atoms is independently selected from N, NH, N(C$_1$-C$_3$ alkyl), O, and S; and wherein said heteroaryl ring is optionally substituted with from 1-4 independently selected R$^c$; or
(iv) heterocyclyl containing from 3-6 ring atoms, wherein from 1-2 of the ring atoms is independently selected from N, NH, N(C$_1$-C$_3$ alkyl), NC(O)(C$_1$-C$_6$ alkyl), O, and S; and wherein said heterocyclyl is optionally substituted with from 1-3 independently selected R$^d$;

R$^a$ at each occurrence is, independently, selected from halo, hydroxyl, C$_1$-C$_6$ alkoxy; C$_1$-C$_6$ haloalkoxy; C$_1$-C$_6$ thiohaloalkoxy; —NHC(O)(C$_1$-C$_6$ alkyl); cyano; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); and —SO$_2$N(C$_1$-C$_6$ alkyl)$_2$;

R$^b$ at each occurrence is, independently, selected from hydroxyl, C$_1$-C$_6$ alkoxy; C$_1$-C$_6$ thioalkoxy; C$_1$-C$_6$ haloalkoxy; C$_1$-C$_6$ thiohaloalkoxy; —NH$_2$; —NH(C$_1$-C$_6$ alkyl); N(C$_1$-C$_6$ alkyl)$_2$; —NHC(O)(C$_1$-C$_6$ alkyl); cyano; —C(O)H; —C(O)(C$_1$-C$_6$ alkyl); —C(O)(C$_1$-C$_6$ haloalkyl); C(O)OH; —C(O)O(C$_1$-C$_6$ alkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); and —SO$_2$N(C$_1$-C$_6$ alkyl)$_2$;

R$^c$ at each occurrence is, independently, selected from any one the substituents delineated collectively in (a), (b), (c), and (d) below:
(a) C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, C$_1$-C$_6$ haloalkyl, —NH(C$_1$-C$_6$ alkyl), N(C$_1$-C$_6$ alkyl)$_2$, or —NHC(O)(C$_1$-C$_6$ alkyl), each of which is optionally substituted with —OH, C$_1$-C$_6$ alkoxy, —NH$_2$, or —SH;
(b) halo; —OH; —CN; nitro; —NH$_2$; azido; C$_2$-C$_4$ alkenyl; C$_2$-C$_4$ alkynyl; —C(O)H; —C(O)(C$_1$-C$_6$ alkyl); C(O)OH; —C(O)O(C$_1$-C$_6$ alkyl); —OC(O)(C$_1$-C$_6$ alkyl); —SO$_2$(C$_1$-C$_6$ alkyl); —SO$_2$(C$_1$-C$_6$ haloalkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$; —NHCO(C$_1$-C$_6$ alkyl), —NHSO$_2$(C$_1$-C$_6$ alkyl); —C(O)O—(CH$_2$)$_{1-3(e.g., 1)}$—C(O)-(phenyl optionally substituted as defined in (d) below (e.g., —C(O)O—CH$_2$—C(O)-(phenyl);
(c) L-C$_3$-C$_8$ cycloalkyl, C$_3$-C$_6$ cycloalkoxy, or L-heterocyclyl containing from 5-7 ring atoms, wherein from 1-2 of the ring atoms of the heterocyclyl is independently selected from N, NH, N(C$_1$-C$_6$ alkyl), NC(O)(C$_1$-C$_6$ alkyl), NC(O)O(C$_1$-C$_6$ alkyl), O, and S; and each of said ring systems is optionally substituted with from 1-3 independently selected C$_1$-C$_4$ alkyl groups; and wherein L is a bond or C$_1$-C$_6$ alkylene; and
(d) phenyl, —O-(phenyl), or heteroaryl containing from 5-6 ring atoms, wherein from 1-2 of the ring atoms of the heteroaryl is independently selected from N, NH, N(C$_1$-C$_3$ alkyl), O, and S; wherein each of said phenyl and heteroaryl is optionally substituted with from 1-3 substituents independently selected from halo; hydroxyl; cyano; —C(O)(C$_1$-C$_6$ alkyl); C(O)OH; —C(O)O(C$_1$-C$_6$ alkyl); nitro; —NH$_2$; —NH(C$_1$-C$_6$ alkyl), N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl, wherein said alkyl or alkyl portion is optionally substituted with —OH, —NH$_2$, or —SH;

R$^d$ at each occurrence is, independently, selected from any one the substituents delineated collectively in (a) and (b) below:
(a) C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, C$_1$-C$_6$ haloalkyl, —NH(C$_1$-C$_6$ alkyl), N(C$_1$-C$_6$ alkyl)$_2$, or —NHC(O)(C$_1$-C$_6$ alkyl), each of which is optionally substituted with —OH, C$_1$-C$_6$ alkoxy, —NH$_2$, or —SH; or
(b) halo; —OH; —CN; nitro; —NH$_2$; azido; C$_2$-C$_4$ alkenyl; C$_2$-C$_4$ alkynyl; —C(O)H; —C(O)(C$_1$-C$_6$ alkyl); C(O)OH; —C(O)O(C$_1$-C$_6$ alkyl); —OC(O)(C$_1$-C$_6$ alkyl); —SO$_2$(C$_1$-C$_6$ alkyl); —SO$_2$(C$_1$-C$_6$ haloalkyl); —C(O)NH$_2$; —C(O)NH(C$_1$-C$_6$ alkyl); C(O)N(C$_1$-C$_6$ alkyl)$_2$; —SO$_2$(C$_1$-C$_6$ alkyl); —SO$_2$NH$_2$; —SO$_2$NH(C$_1$-C$_6$ alkyl); —SO$_2$N(C$_1$-C$_6$ alkyl)$_2$; —NHCO(C$_1$-C$_6$ alkyl), —NHSO$_2$(C$_1$-C$_6$ alkyl).

In some embodiments, it is provided when R$^{25}$ is hydrogen, then:
(1) R$^{24}$ cannot be unsubstituted cyclohexyl when R$^{22}$ is 2,3,4-trihydroxyphenyl, and R$^{23}$ is CH$_3$;
(2) R$^{24}$ cannot be 4-fluorophenyl when R$^{22}$ is 3,4-dihydroxyphenyl, and R$^{23}$ is 2H-benzo[b][1,4]oxazinyl-3 (4H)-onyl;
(3) R$^{24}$ cannot be 2,4-difluorophenyl when R$^{22}$ is 2,4-dihydroxyphenyl, and R$^{23}$ is furyl; and
(4) R$^{24}$ cannot be 3-pyridyl when R$^{22}$ is 2,4-dihydroxyphenyl, and R$^{23}$ is furyl.

The compounds, salts, combinations, and compositions described herein are therapeutically useful for treating (e.g., controlling, relieving, ameliorating, alleviating, or slowing the progression of) or preventing (e.g., delaying the onset of or reducing the risk of developing) diseases, disorders, and conditions associated with deregulated apoptosis of cells (e.g., diseased or damaged cells; e.g., insufficient apoptosis of diseased or damaged cells; or lack of apoptosis of diseased or damaged cells). Examples of such diseases, disorders, and conditions include (but are not limited to) those associated with blockade(s) of cell death pathways (e.g., over-expression of anti-apoptotic BCL-2 proteins; e.g., over-expression of anti-apoptotic BCL-2 proteins that fall outside of the inhibitory spectrum of a particular anti-apoptotic BCL-2 protein inhibitor, such as ABT-263 or ABT-737). Examples of such diseases, disorders, and conditions include hyperproliferative diseases, such as cancer.

While not wishing to be bound by theory, it is believed that the compounds, salts, combinations, and compositions described herein induce and increase apoptosis in target cells (e.g., pathogenic cells including, but not limited to, cancer cells), thereby suppressing tumor growth and/or proliferation. It is further believed that increasing apoptosis in such target cells reestablishes the normal apoptotic control that, during homeostasis, is associated with a regulated balance between pro- and anti-apoptotic protein functions.

II

In embodiments, the compounds, compositions, combinations, and methods described herein can include any one or more of the features described below throughout sections [A] through [G] below.

[A] In some embodiments, the compound of formula (I) and/or (II) selectively inhibit MCL-1 and/or BFL-1/A1. As used herein, a compound of formula (I) that "selectively inhibits MCL-1 and/or BFL-1/A1" meets at least one of the four performance criteria described in sections [1], [2], [3], and [4] below.

[1] The first performance criteria is that the formula (I) and/or (II) compound exhibits a preference for MCL-1ΔNΔC, as defined both by >50% displacement of the FITC-MCL-1 SAHB$_A$/MCL-1ΔNΔC interaction and a >45% difference in peptide displacement from MCL-1ΔNΔC vs. BCL-X$_L$ΔC. MCL-1 SAHBs are hydrocarbon-stapled MCL-1 BH3 helices that were previously shown using chemical, structural, and biological methods to selectively target MCL-1 and sensitize cancer cells to caspase-dependent apoptosis[34]. MCL-1 SAHB$_A$ is utilized herein as a high fidelity screening tool due to its potency and specificity-of-action. FITC indicates that the stapled peptide is labeled with Fluorescein isothiocyanate. The following two competitive fluorescence polarization (FP) assays are used to evaluate whether a formula (I) compound meets the first performance criteria: (i) a fluorescence polarization (FP) screening assay (Z-factor, 0.62) based on the direct binding interaction between FITC-MCL-1 SAHB$_A$ and MCL-1ΔNΔC (EC$_{50}$, 14 nM) (Figure S1A-C), in which the compound is screened for its capacity to displace FITC-MCL-1 SAHB$_A$ from recombinant MCL-1ΔNΔC (aa 172-327); and (ii) a counterscreen using a competitive FP assay (Z-factor, 0.71) developed based on the direct and selective interaction between FITC-BAD BH3 and BCL-X$_L$ΔC (EC$_{50}$, 26 nM). See Examples section for a description of these assays.

[2] The second performance criteria is that the formula (I) and/or (II) compound competes with FITC-MCL-1 SAHB$_A$ for MCL-1ΔNΔC binding at IC$_{50}$ potencies of <30 μM. The following in vitro binding assays are used to evaluate whether a formula (I) compound meets the second performance criteria: (i) repeat single-dose testing in the differential competitive FP screen (supra); (ii) alternative single-dose selectivity screen of confirmed MCL-1-directed antagonists comparing relative displacement of FITC-BID BH3, a dual binder,[35] from MCL-1ΔNΔC vs. BCL-X$_L$ΔC; and then (iii) dose-responsive competitive binding against the FITC-MCL-1 SAHB$_A$/MCL-1ΔNΔC complex. See Examples section for a description of these assays.

[3] The third performance criteria is that the formula (I) and/or (II) compound (i) competes with FITC-MCL-1 SAHB$_A$ for MCL-1ΔNΔC binding with an IC$_{50}$ of less than 10 μM (e.g., less than 5 μM); (ii) competes with FITC-BID BH3 for MCL-1ΔNΔC binding with an IC$_{50}$ of less than 10 μM (e.g., less than 5 μM); and (iii) exhibits an IC$_{50}$>50 μM in its capacity to displace FITC-BID BH3 from BCL-X$_L$ΔC (IC$_{50}$>50 μM). See Examples section for a description of these assays.

[4] A fourth performance criteria is that the formula (I) and/or (II) compound competes with FITC-BID BH3 for BFL-1/A1ΔC binding with an IC$_{50}$ of less than 10 μM (e.g., less than 5 μM); and (iii) exhibits an IC$_{50}$>50 μM in its capacity to displace FITC-BID BH3 from BCL-X$_L$ΔC (IC$_{50}$>50 μM). See Examples section for a description of these assays. Compounds of the formula (I) and/or (II) compound may fulfill performance criteria 1-3 (selective MCL-1 targeting), 1-4 (selective MCL-1 and BFL-1/A1 targeting), or 4 (selective BFL-1/A1 targeting).

[5] Accordingly, in another aspect, methods for identifying selective MCL-I and BFL-1/A1 binding agents are featured, which include contacting an MCL-I and/or BFL-1/A1 polypeptide bound to an MCL-1 or BFL-1/A1-binding BH3 peptide or SAHB with a test compound under conditions suitable for interaction of the test compound with the MCL-I and/or BFL-1/A1 polypeptide; and detecting dissociation of the BH3 peptide or SAHB from the MCL-1 and/or BFL-1/A1 polypeptide, where detection of such dissociation identifies a test compound as a selective MCL-1 and/or BFL-1/A1 binding agent. In another embodiment, the MCL-1 and/or BFL-1/A1 binding agent is a selective MCL-1 inhibitor, selective MCL-1 and BFL-1/A1 inhibitor, or a selective BFL-1/A1 inhibitor. In a further embodiment, the MCL-1 or BFL-1/A1 polypeptide, or, optionally, the BH3 peptide or SAHB, is labeled, e.g., with FITC. In still other embodiments, the methods further include contacting a non-MCL-1 or non-BFL-1/A1, anti-apoptotic BCL-2 family polypeptide bound to an inhibitor of said non-MCL-1 or non-BFL-1/A1, anti-apoptotic BCL-2 family polypeptide with a test compound under conditions suitable for interaction of the test compound with the non-MCL-1 or non-BFL-1/A1, anti-apoptotic BCL-2 family polypeptide; and detecting dissociation (if any) of the inhibitor from the non-MCL-1 or non-BFL-1/A1, anti-apoptotic BCL-2 family polypeptide. Effects that may be observed include, but are not limited to, those described in the Examples section.

[B] The compound of formula (I) can include any one or more of the following features.

In some embodiments, $R^{22}$ is aryl (e.g., phenyl), which is optionally substituted with from 1-5 (e.g., 1-3) independently selected Z (e.g., hydroxyl). In certain embodiments, $R^{22}$ is phenyl, which is optionally substituted with from 1-3 hydroxyl groups.

In some embodiments, $R^{23}$ is $C_1$-$C_8$ (e.g., $C_1$-$C_4$) alkyl; e.g., $CH_3$.

In some embodiments, $R^{24}$ is unsubstituted cycloalkyl or cycloalkyl (e.g., $C_3$-$C_7$) that is substituted with from 1-5 (e.g., 1-3) independently selected Z; e.g., unsubstituted cycloalkyl, e.g., cyclohexyl.

In some embodiments:

$R^{22}$ is aryl (e.g., phenyl), which is optionally substituted with from 1-5 (e.g., 1-3) independently selected Z (e.g., hydroxyl). In certain embodiments, $R^{22}$ is phenyl, which is optionally substituted with from 1-3 hydroxyl groups; and $R^{23}$ is $C_1$-$C_8$ (e.g., $C_1$-$C_4$) alkyl; e.g., $CH_3$; and $R^{24}$ is unsubstituted cycloalkyl or cycloalkyl (e.g., $C_3$-$C_7$) that is substituted with from 1-5 (e.g., 1-3) independently selected Z; e.g., unsubstituted cycloalkyl, e.g., cyclohexyl.

In certain embodiments, the compound is:

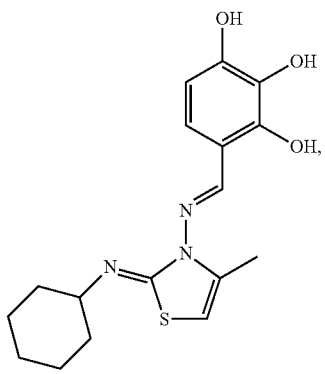

MIM1 which is sometimes referred to herein as "MIM1."

Other exemplary compounds of formula (I) include those disclosed in FIG. 16 (also disclosed in FIG. 4D of WO 2011/094708, which is incorporated herein by reference.

The compounds of formula (II) can include any one or more of the following features as well as any one or more of the features described in the detailed description and/or the claims.

$R^{26}$ and $R^{27}$ together are a bond.

$R^{25}$ is:

(i) hydrogen;

(ii) $C_1$-$C_8$ alkyl or $C_1$-$C_8$ haloalkyl, each of which is optionally substituted with from 1-2 independently selected $R^b$;

(iii) $C_3$-$C_6$ cycloalkyl or $C_3$-$C_6$ cycloalkenyl, each of which is optionally substituted with from 1-4 independently selected $R^d$; or (iv) —C(O)O($C_1$-$C_6$ alkyl).

$R^{22}$ can be $C_6$-$C_{10}$ (e.g., $C_6$) aryl, which is optionally substituted with from 1-5 (e.g., 1-3, e.g., 3) independently selected $R^a$.

$R^{22}$ can be $C_6$-$C_{10}$ (e.g., $C_6$) aryl, which is substituted with from 1-5 (e.g., 1-3, e.g., 3) independently selected $R^a$.

Each $R^a$ can be independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

Each $R^a$ can be independently selected from halo, hydroxyl, $C_1$-$C_6$ alkoxy; —NHC(O)($C_1$-$C_6$ alkyl); and C(O)OH.

One, two, or three (e.g., three) of the independently selected $R^a$ can be hydroxyl.

$R^{22}$ can have formula (A):

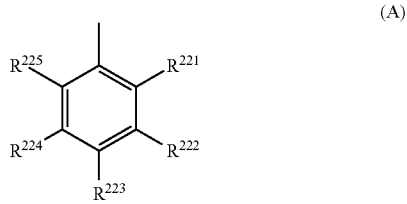

(A)

wherein:

one, two, or three (e.g., three) of $R^{221}$, $R^{222}$, $R^{223}$, $R^{224}$, and $R^{225}$ are each independently selected $R^a$, and the others are hydrogen.

$R^{22}$ can have formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are each independently selected $R^a$, and the others are hydrogen (e.g., each of the three $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH; e.g., each of the three $R^a$ is independently selected from halo, hydroxyl, $C_1$-$C_6$ alkoxy; —NHC(O)($C_1$-$C_6$ alkyl); and C(O)OH; e.g., each of the three $R^a$ is hydroxyl).

$R^{25}$ can be hydrogen.

$R^{25}$ can be a substituent other than hydrogen, such as $C_1$-$C_8$ alkyl or $C_1$—C haloalkyl, each of which is optionally substituted with from 1-2 independently selected $R^b$. For example, $R^{25}$ can be $C_1$-$C_8$ alkyl, which is optionally substituted with from 1-2 independently selected $R^b$; e.g., $R^{25}$ can be unsubstituted $C_1$-$C_8$ alkyl (e.g., $C_1$-$C_3$ alkyl, e.g., $CH_3$).

$R^{23}$ can be $C_3$-$C_6$ cycloalkyl (e.g., cyclopropyl), which is optionally substituted with from 1-4 independently selected $R^d$ (e.g., $C_1$-$C_6$ alkyl, $C_1$-$C_3$ alkyl).

$R^{23}$ can be $C_1$-$C_8$ (e.g., $C_1$-$C_3$, e.g., $C_1$-$C_2$, $CH_3$; $C_2$-$C_8$, $C_3$-$C_8$, $C_4$-$C_8$, tert-butyl) alkyl, which is optionally substituted with from 1-2 independently selected $R^b$.

$R^{23}$ can be unsubstituted $C_1$-$C_8$ alkyl (e.g., unsubstituted $C_2$-$C_8$ alkyl, unsubstituted $C_3$-$C_8$ alkyl, unsubstituted branched $C_3$-$C_8$ alkyl, unsubstituted branched $C_4$-$C_8$ alkyl). For example, $R^{23}$ is $CH_3$. As another example, $R^{23}$ can be tert-butyl.

In some embodiments, $R^{24}$ can be $C_3$-$C_{10}$ (e.g., $C_3$-$C_8$, e.g., $C_3$-$C_6$, e.g., $C_6$) cycloalkyl, which is optionally substituted with from 1-4 independently selected $R^d$ (as defined above or anywhere herein).

[C] In some embodiments, the one or more additional therapeutic agents that bind to and inhibit anti-apoptotic proteins (e.g., agents that inhibit anti-apoptotic BCL-2 proteins), are selected from ABT-199, ABT-263, ABT-737, obatoclax, gossypol derivatives, IAP inhibitors, and stapled peptides that target anti-apoptotic proteins (MCL-1 SAHB (see, Stewart et al, Nature Chem Biol, 2010), BID SAHB (Walensky et al Science 2004), BAD SAHB (Danial et al Nature Medicine 2008), and BIM SAHB (Gavathiotis et al Nature 2008), etc.). In certain embodiments, the one or more additional therapeutic agents that bind to and inhibit anti-apoptotic proteins are selected from ABT-199, ABT-263 and ABT-737, e.g., ABT-737.

"ABT-263" refers to N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenyl-sulfanyl)methyl)propyl)amino)-3-((trifluoromethyl)sulfonyl)benzenesulfonamide.

"ABT-737" refers to N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide.

"ABT-199" refers to (Souers et al. Nat Med 2013, 19, p 202-208):

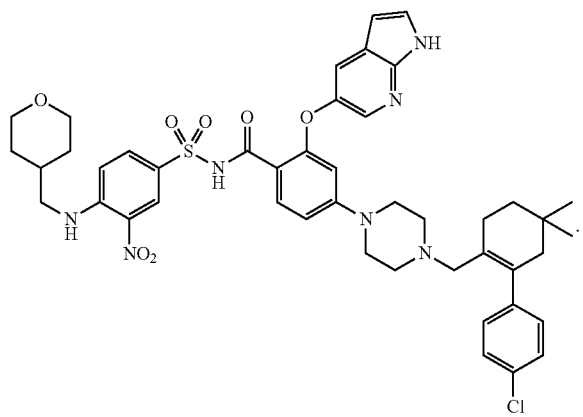 [SMILES: CC1(C)CCC(CN2CCN(c3ccc(C(=O)NS(=O)(=O)c4ccc(NCC5CCOCC5)c([N+](=O)[O-])c4)c(Oc4cnc5[nH]ccc5c4)c3)CC2)=C(c2ccc(Cl)cc2)C1]

[D] In some embodiments, the compound of formula (I) and/or (II) has an interaction profile that is opposite to the interaction profile of the one or more additional therapeutic agents that bind to and inhibit anti-apoptotic proteins (see, e.g., the difference in interaction profiles between the compound described herein as "MIM1" and that of ABT-737).

In some embodiments, the combination of a compound of formula (I) and/or (II), or a pharmaceutically acceptable salt thereof (e.g., a compound of formula (I) and/or (II) or a salt thereof that selectively inhibits MCL-1 and/or BFL-1/A1), and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737) exhibits greater than additive anti-cancer activity (e.g., greater than additive cancer cell cytotoxicity, e.g., greater than additive leukemia cancer cell cytotoxicity).

In some embodiments:

(i) the compound of formula (I) and/or (II) has an interaction profile that is opposite to the interaction profile of the one or more additional therapeutic agents that bind to and inhibit, or indirectly modulate, anti-apoptotic proteins (see, e.g., the difference in interaction profiles between the compound described herein as "MIM1" and that of ABT-737); and (ii) the combination of a compound of formula (I) and/or (II), or a pharmaceutically acceptable salt thereof (e.g., a compound of formula (I) or a salt thereof that selectively inhibits MCL-1 and/or BFL-1/A1), and one or more additional therapeutic agents that bind to and inhibit, or indirectly modulate, anti-apoptotic proteins (e.g., agents that bind to and inhibit anti-apoptotic BCL-2, BCL-$X_L$, BCL-w, MCL-1, and BFL-1/A1; e.g., agents that bind to and inhibit anti-apoptotic BCL-2/BCL-$X_L$; e.g., agents such as ABT-263 and ABT-737; e.g., ABT-737) exhibits greater than additive anti-cancer activity (e.g., greater than additive cancer cell cytotoxicity, e.g., greater than additive leukemia cancer cell cytotoxicity).

[E] In some embodiments, the one or more additional therapeutic agents bind to and inhibit, or indirectly modulate, anti-apoptotic proteins.

In some embodiments, the one or more additional therapeutic agents directly activate pro-apoptotic proteins, such as BIM SAHB, ref Labelle et al JCI, 2012, 122 p. 2018-31) or selective activators of BAX or BAK (Gavathiotis et al. Nat Chem Biol, 2012, 8, 639-645).

In certain embodiments, combinations can include one or more additional therapeutic agents bind to and inhibit, or indirectly modulate, anti-apoptotic proteins and/or one or more additional therapeutic agents directly activate pro-apoptotic proteins, such as BIM SAHB, ref Labelle et al JCI, 2012, 122 p. 2018-31) or selective activators of BAX or BAK (Gavathiotis et al. Nat Chem Biol, 2012, 8, 639-645).

In some embodiments, the one or more additional therapeutic agents transcriptionally repress anti-apoptotic proteins (rather than directly bind and inhibit them); see, e.g., Wei et al Cancer Cell, 2012, 21, p 547-562.

In certain embodiments, the one or more additional therapeutic agents include: agents that induce apoptosis; polynucleotides (e.g., anti-sense, ribozymes, siRNA); polypeptides (e.g., enzymes and antibodies); biological mimetics (BH3 mimetics); alkaloids; alkylating agents; antitumor antibiotics; antimetabolites; hormones; platinum compounds; monoclonal or polyclonal antibodies (e.g., antibodies conjugated with anticancer drugs, toxins, defensins, etc.), toxins, radionuclides; biological response modifiers (e.g., interferons (e.g., IFN-α, etc.) and interleukins (e.g., IL-2, etc.), etc.); adoptive immunotherapy agents; hematopoietic growth factors; agents that induce tumor cell differentiation (e.g., all-trans-retinoic acid, etc.); gene therapy reagents (e.g., antisense therapy reagents and nucleotides); tumor vaccines; angiogenesis inhibitors; proteosome inhibitors: NF kappa β modulators; anti-CDK compounds; HDAC inhibitors; and the like.

In certain embodiments, at least one of the one or more additional therapeutic agents is a chemotherapeutic agent selected from an alkylating agent (e.g., carboplatin), an anti-metabolite (e.g., methotrexate), an anthracycline (e.g., doxorubicin), a plant alkaloid (e.g., vincristine), an antibody (e.g., rituxan), a steroid (e.g., dexamethasone), a targeted therapy (e.g., TRAIL, bortezamib), or another cytotoxic or cytostatic agent.

In certain embodiments, at least one of the one or more additional therapeutic agents is an agent that induces or stimulates apoptosis, including, but are not limited to, kinase inhibitors (e.g., Epidermal Growth Factor Receptor (EGFR) kinase inhibitor, Vascular Growth Factor Receptor (VGFR) kinase inhibitor, Fibroblast Growth Factor Receptor (FGFR) kinase inhibitor, Platelet-derived Growth Factor Receptor (PDGFR) kinase inhibitor, and Bcr-Abl kinase inhibitors such as GLEEVEC); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDI-APRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; and staurosporine, and the like.

In certain embodiments, at least one of the one or more additional therapeutic agents is a chemotherapeutic agent (e.g., as defined above) and at least one of the one or more additional therapeutic agents is an agent that induces or stimulates apoptosis (e.g., as defined above), e.g., one or more therapeutic agents that bind to and inhibit, or indirectly modulate, anti-apoptotic proteins and/or one or more additional therapeutic agents directly activate pro-apoptotic proteins, such as BIM SAHB, ref Labelle et al JCI, 2012, 122 p. 2018-31) or selective activators of BAX or BAK (Gavathiotis et al. Nat Chem Biol, 2012, 8, 639-645); and/or one or more additional therapeutic agents that transcriptionally repress anti-apoptotic proteins (rather than directly bind and inhibit them); see, e.g., Wei et al Cancer Cell, 2012, 21, p 547-562.

[F] In some embodiments, the combinations further include one or more conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. Thus, the combinations can be in the form of a pharmaceutical composition.

[G] In some embodiments, (i) the compound of formula (I) and/or (II), or a pharmaceutically acceptable salt thereof; (ii) the one or more additional therapeutic agents that bind to and inhibit, or indirectly modulate, anti-apoptotic proteins; (iii) the one or more additional therapeutic agents (if present); and (iv) one or more conventional non-toxic pharmaceutically-acceptable carriers, adjuvants or vehicles (if present) form part of a single composition (e.g., a pharmaceutical composition) or single dosage form.

In other embodiments, at least one of (i), (ii), (iii), (iv) immediately above is/(are) contained or packaged separately from the other components of the combination (e.g., as part of a kit). In certain embodiments, when (i), (ii), and/or (iii) is separately contained or packaged, said separately contained or packaged therapeutic agent can be combined with one or more conventional non-toxic pharmaceutically-acceptable carriers, adjuvants or vehicles.

III

[A] In one aspect, methods for treating (e.g., controlling, relieving, ameliorating, alleviating, or slowing the progression of) or preventing (e.g., delaying the onset of or reducing the risk of developing) diseases, disorders, and conditions associated with deregulated apoptosis of cells (e.g., diseased or damaged cells; e.g., insufficient apoptosis of diseased or damaged cells; or the lack of apoptosis of diseased or damaged cells) in a subject in need thereof are featured. The methods include administering to the subject (e.g., an effective amount of) a compound of formula (I) and/or (II), or a pharmaceutically acceptable salt thereof or a combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the agent.

[B] In another aspect, methods for treating (e.g., controlling, relieving, ameliorating, alleviating, or slowing the progression of) or preventing (e.g., delaying the onset of or reducing the risk of developing) diseases, disorders, and conditions associated with blockade(s) of cell death pathways (e.g., over-expression of anti-apoptotic proteins BCL-2 proteins) in a subject in need thereof are featured. The methods include administering to the subject (e.g., an effective amount of) a compound of formula (I) and/or (II), or a pharmaceutically acceptable salt thereof or a combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the agent.

[C] In a further aspect, methods for treating (e.g., controlling, relieving, ameliorating, alleviating, or slowing the progression of) or preventing (e.g., delaying the onset of or reducing the risk of developing) a hyperproliferative disease in a subject in need thereof are featured. The methods include administering to the subject (e.g., an effective amount of) a compound of formula (I) and/or (II), or a pharmaceutically acceptable salt thereof or a combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737)), or (where applicable) a pharmaceutically acceptable salt of the agent.

In an aspect, methods for treating (e.g., controlling, relieving, ameliorating, alleviating, or slowing the progression of) a hyperproliferative disease in a subject in need thereof are featured. The methods include administering to the subject (e.g., an effective amount of) a compound of formula (I) and/or (II), or a pharmaceutically acceptable salt thereof or a combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the agent.

[D] In still another aspect, methods for treating (e.g., controlling, relieving, ameliorating, alleviating, or slowing the progression of) or preventing (e.g., delaying the onset of or reducing the risk of developing) cancer in a subject in need thereof are featured. The methods include administering to the subject (e.g., an effective amount of) a compound of formula (I) and/or (II), or a pharmaceutically acceptable salt thereof or a combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the agent.

In an aspect, methods for treating (e.g., controlling, relieving, ameliorating, alleviating, or slowing the progression of) cancer in a subject in need thereof are featured. The methods include administering to the subject (e.g., an effective amount of) a compound of formula (I) and/or (II), or a pharmaceutically acceptable salt thereof or a combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the agent.

[E] In yet another aspect, methods of modulating (e.g., increasing) apoptosis in vitro or in vivo are featured. Also featured are methods of modulating (e.g., decreasing) cell division in vitro or in vivo are featured.

In certain embodiments, the methods include contacting a sample (e.g., containing one or more cancer cells) with a compound of formula (I) and/or (II), or a pharmaceutically acceptable salt thereof or a combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the agent.

In other embodiments, the methods include administering a a compound of formula (I) and/or (II), or a pharmaceutically acceptable salt thereof or combination that includes a compound of formula (I) and/or (II), or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-$X_L$, BCL-w, MCL-1, and/or BFL-1/A1; e.g., one or more therapeutic agents that directly bind to and inhibit anti-apoptotic BCL-2/BCL-$X_L$; e.g., agents such as ABT-199, ABT-263 and ABT-737; e.g., ABT-737), or (where applicable) a pharmaceutically acceptable salt of the agent to a subject (e.g., a subject in need thereof, e.g., a mammal, such as a human).

[F] In some embodiments, the methods described above and throughout this disclosure can include one or more of the following features.

[1] The cancer can include carcinomas (originating in the outer layer of cells of the skin and internal membranes, e.g., breasts, lungs, intestines, skin, prostate, etc.); sarcomas (arising from connective tissue such as bone, muscle, cartilage and blood vessels), and hematologic malignancies (e.g., lymphomas and leukemias, which arise in the blood or blood-forming organs such as the spleen, lymph nodes and bone marrow). Cancer cells can include, for example, tumor cells, neoplastic cells, malignant cells, metastatic cells, and hyperplastic cells.

Non-limiting examples of cancers include breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

In an embodiment, the disease or disorder is a hyperproliferative disorder, e.g., a lymphoma, leukemia, carcinoma (e.g. hepatic, breast, lung), multiple myeloma, or a sarcoma. In one embodiment, the leukemia is AML or ALL. In a related embodiment, the hyperproliferative disorder is a resistant hyperproliferative disorder; optionally, one that is resistant to a BCL-2 inhibitor. In another embodiment, the hyperproliferative disorder is a relapsed or refractory cancer.

[2] The subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

[3] The one or more additional therapeutic agents that bind to and inhibit anti-apoptotic proteins and any additional therapeutic agents may be administered separately, as part of a multiple dose regimen, from the compound of formula (I) and/or (II) (e.g., sequentially, e.g., on different overlapping schedules with the administration of one or more compounds of formula (I) and/or (II) (including any subgenera or specific compounds thereof)). In other embodiments, the one or more additional therapeutic agents that bind to and inhibit anti-apoptotic proteins and any additional therapeutic agents may be part of a single dosage form, mixed together with the compound of formula (I) and/or (II) in a single composition. In still another embodiment, the one or more additional therapeutic agents that bind to and inhibit anti-apoptotic proteins and any additional therapeutic agents can be given as a separate dose that is administered at about the same time that one or more compounds of formula (I) and/or (II) are administered (e.g., simultaneously with the administration of one or more compounds of formula (I) and/or (II) (including any subgenera or specific compounds thereof)). Both the compound of formula (I) and/or (II) and the one or more additional therapeutic agents that bind to and inhibit anti-apoptotic proteins and any additional therapeutic agents can be present at dosage levels of between about 1 to 100%, and more preferably between about 5 to 95% of the dosage normally administered in a monotherapy regimen.

[4] The methods described above and throughout this disclosure can include any one or more of the features described throughout any one or more of sections [II][A] through [II][G].

IV

In embodiments, an amount of a compound of formula (I) and/or (II) or salt thereof can be an effective amount. "An effective amount" refers to an amount of a compound that confers a therapeutic effect (e.g., treats, e.g., controls, relieves, ameliorates, alleviates, or slows the progression of; or prevents, e.g., delays the onset of or reduces the risk of developing, a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (Here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, and polycyclic rings.

The following definitions are used unless otherwise described. Specific and general values listed below for radicals, substituents, and ranges are for illustration only. They do not exclude other defined values or other values within defined ranges for the radicals and substituents. Unless otherwise indicated, alkyl, alkylene, alkoxy, alkenyl, and the like denote both straight and branched groups.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more subsitutents. Examples of alkyl groups include, without limitation, methyl, ethyl, n-propyl, isopropyl, and tert-butyl.

The term "haloalkyl" refers to an alkyl group in which at least one hydrogen atom is replaced by halo. In some embodiments, more than one hydrogen atom (e.g., 2, 3, 4, 5, 6, 7, 8, 9, 10, 11, 12, 13, or 14) is replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—OCH$_3$), ethoxy, propoxy, isopropoxy, or butoxy.

The term "oxo" refers to doubly nond oxygen.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include groups such as ethynyl, propargyl, and 3-hexynyl. One of the triple bond carbons can optionally be the point of attachment of the alkynyl substituent.

The term "cycloalkyl" refers to a fully saturated monocyclic, bicyclic, tricyclic, or other polycyclic hydrocarbon group. Any atom can be optionally substituted, e.g., by one or more substituents. A ring carbon serves as the point of attachment of a cycloalkyl group to another moiety. Cycloalkyl moieties can include groups such as cyclopropyl, cyclobutyl, cyclopentyl, cyclohexyl, cycloheptyl, adamantyl, and norbornyl (bicyclo[2.2.1]heptyl).

The term "aryl" refers to an aromatic monocyclic, bicyclic (2 fused rings), tricyclic (3 fused rings), or polycyclic (>3 fused rings) hydrocarbon ring system. One or more ring atoms can be optionally substituted by one or more substituents for example. Aryl moieties include groups such as phenyl and naphthyl.

The term "heteroaryl" refers to a stable 5- to 13-membered aromatic heterocycle having in the range of from 1 up to 4 heteroatoms from the group consisting of nitrogen, phosphorus, oxygen and sulfur, which ring or ring system can be linked via a carbon atom or a nitrogen atom, if such an atom is present. For purposes of this invention, the heteroaryl ring radical may be a monocyclic, bicyclic or tricyclic ring system. Examples of such heteroaryl radicals are: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolicenyl, indolyl, benzo[b]thienyl, benzo[b]furyl, benzothiazolyl, benzothiadiazolyl, indazolyl, quinolyl, isoquinolyl, isoquinolyl, naphthyridinyl, quinazolinyl, oxadiazolyl, benzoxazolyl, tetrazoyl, triazolyl, thiadiazolyl, and benzimidazolyl.

The term "heterocycloalkyl" or "heterocyclyl" refers to a stable 3 to 13 membered saturated or partially unsaturated heterocycle having in the range from 1 up to 4 heteroatoms from the group consisting of nitrogen, phosphorus, oxygen and sulfur, which ring or ring system can be linked via a carbon atom or a nitrogen atom, if such an atom is present. For purposes of this invention, the heterocyclic ring radical may be a monocyclic, bicyclic or tricyclic ring system, which may include fused, bridged or spiro ring systems. Examples of such heterocyclyl radicals are: tetrahydropyranyl, aziridyl, azepanyl, tetrahydrofuryl, pyrrolidinyl, pyrrolinyl, piperidinyl, 1,2 dihydropyridinyl, 1,4 dihydropyridinyl, piperazinyl, morpholinyl, thiomorpholinyl, azepinyl, oxazolinyl, thiazolinyl and 1,4 diazepinyl.

The term "substituent" refers to a group "substituted" on groups such as an alkyl, haloalkyl, cycloakyl, heterocyclyl, aryl, or heteroaryl group at any atom of that group. In one aspect, the substituent(s) on a group are independently any one single or any combination of two or more of the permissible atoms or groups of atoms delineated for that substituent. In another aspect, a substituent may itself be substituted with any one of the above substituents.

Further, as used herein, the phrase "optionally substituted" means unsubstituted (e.g., substituted with hydrogen (H)) or substituted. As used herein, the term "substituted" means that a hydrogen atom is removed and replaced by a substituent. It is understood that substitution at a given atom is limited by valency.

Descriptors such as "$C_6$-$C_{10}$ aryl that is optionally substituted with from 1-4 independently selected $R^b$ (and the like) is intended to include both an unsubstituted $C_6$-$C_{10}$ aryl group and a $C_6$-$C_{10}$ aryl group that is substituted with from 1-4 independently selected $R^b$. The use of a substituent (radical) prefix name such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A and 1B are graphical representations of data related to the development of a Stapled Peptide-based High-Throughput Competitive Screening Assay for Identifying MCL-1-selective Small Molecules. High-throughput competitive fluorescence polarization (FP) binding assays were developed based on the direct binding interaction between FITC-MCL-1 SAHB$_A$ and MCL-1ΔNΔC (EC$_{50}$, 14 nM) and FITC-BAD BH3 and BCL-X$_L$ΔC C (EC$_{50}$, 26 nM).

FIGS. 2A and 2B show Positive and Negative Controls for Screening Conditions. The initial screening conditions were validated for (A) MCL-1 screening using a positive control for complete displacement (BID SAHB$_A$) and a negative control for no displacement (BCL-2 SAHB$_A$), and for (B) BCL-X$_L$ counterscreening using a positive control for complete displacement (BAD SAHB$_A$) and a negative control for no displacement (MCL-1 SAHB$_A$).

FIGS. 3A and 3B show Z-factor Determination for the MCL-1 Screen and BCL-X$_L$ Counterscreen. (A) The MCL-1 screen yielded a Z-factor of 0.62, and (B) the BCL-X$_L$ counterscreen yielded a Z-factor of 0.71.

FIG. 4 shows Identification of a Selective Inhibitor of Anti-apoptotic MCL-1. A high-throughput stapled peptide-based screen for small molecules that selectively target MCL-1ΔNΔC identified MIM1. The molecular structure of MIM1 is characterized by a thiazolyl core substituted with methyl, cyclohexylimino, and benzenetriol R groups.

FIG. 5 shows $^1$H NMR of MIM1.

FIGS. 6A, 6B, and 6C show MIM1 binds MCL-1 selectively in an FP competition assay. (A) MCL-1 SAHB$_D$ and MIM1 dose-responsively compete with FITC-MCL-1 SAHB$_A$ for binding to MCL-1ΔNΔC, whereas the BCL-2/BCL-X$_L$-selective antagonist ABT-737 has no effect. (B) Similarly, MCL-1 SAHB$_D$ and MIM1, but not ABT-737, effectively compete with FITC-BID BH3 peptide for binding to MCL-1ΔNΔC. (C) In contrast, ABT-737 dose-responsively competes with FITC-BID BH3 for binding to BCL-X$_L$ΔC, whereas MCL-1 SAHB$_D$ and MIM1 show no BCL-X$_L$ΔC-binding activity. Data are mean±SEM for experiments performed in duplicate and repeated twice with independent preparations of recombinant protein with similar results.

FIG. 7 shows MIM1 Targets the Canonical BH3-Binding Pocket of MCL-1. Measured chemical shift changes of $^{15}$N-MCL-1ΔNΔC upon MIM1 titration up to a ratio of 2:1 MIM1:MCL-1 are plotted as a function of MCL-1ΔNΔC residue. Affected residues are represented as purple bars in the plot (calculated significance threshold >0.0197 p.p.m.). Residues with significant backbone amide chemical shift changes (purple) are concentrated in a subregion of the canonical BH3-binding pocket (green). Of note, MCL-1ΔNΔC residues M250, V253, F254, S255, D256, G257, G262, and R263 are unassigned.

FIG. 8 shows Molecular Docking of MIM1 on MCL-1ΔNΔC. The docked structure of MIM1 at the canonical BH3-binding pocket of MCL-1ΔNΔC predicts that (1) the cyclohexyl group makes complementary hydrophobic contacts with the region of the protein interface flanked by MCL-1 SAHB$_D$ residues L213 and V216, (2) the thiazolyl core and its methyl substituent points directly into a deep crevice occupied by MCL-1 SAHB$_D$ L213 in the stapled peptide/protein complex, and (3) the benzene-1,2,3-triol (or pyrogallol) moiety engages in hydrophilic contacts with D256 and R263, two charged MCL-1 residues implicated in complementary electrostatic interactions with R214 and D218 of MCL-1 SAHB$_D$.

FIGS. 9A, 9B, 9C, and 9D show Selective Blockade of MCL-1-mediated Suppression of BAX activation by MIM1. (A) BH3-only protein tBID directly activates BAX-mediated liposomal release, which is effectively suppressed by treatment with anti-apoptotic MCL-1ΔNΔC and BCL-X$_L$ΔC. (B) MCL-1 SAHB$_D$ selectively inhibits MCL-1ΔNΔC suppression of tBID-induced BAX activation. (C) ABT-737 selectively inhibits BCL-X$_L$ΔC suppression of tBID-induced BAX activation. (D) The activity profile of MIM1 in the liposomal release assay mirrors the MCL-1 selectivity of MCL-1 SAHB$_D$. Liposomal assays were conducted in triplicate for each condition using two independent preparations of recombinant BAX with similar results.

FIG. 10 shows Western Blot Analysis of Genetically-defined p185$^+$Arf$^{-/-}$ Cells. Whereas the parental p185$^+$Arf$^{-/-}$ CML cells express both MCL-1 and BCL-X$_L$, MCL-1- and BCL-X$_L$-rescued p185$^+$Arf$^1$-Mcl-1$^{-/-}$ cells demonstrate overexpression of MCL-1 or BCL-X$_L$, respectively. The pro-apoptotic effectors BAX and BAK are expressed at similar levels in all three cell lines.

FIG. 11 shows MIM1 Selectively Impairs the Viability of MCL-1-dependent Leukemia Cells. MIM1 dose-responsively induces cell death of p185$^+$Arf$^{-/-}$Mcl-1$^{-/-}$ CML cells rescued by overexpression of MCL-1, but not BCL-X$_L$, whereas ABT-737 has the opposite activity profile, as measured by CellTiter-Glo assay at 24 h. Data are mean±SEM for experiments performed in duplicate, normalized to vehicle control, and repeated at least twice with independent cell cultures.

FIG. 12 shows MIM1 Selectively Activates Caspase 3/7 in MCL-1-dependent Leukemia Cells. The selective cytotoxic effects of MIM1 and ABT-737 are accompanied by dose-responsive caspase 3/7 activation in the respective MCL-1 or BCL-X$_L$-rescued p185$^+$Arf$^{-/-}$Mcl-1$^{-/-}$ leukemia cell lines, as measured at 8 h post-treatment. Data are mean±SEM for experiments performed in duplicate, normalized to vehicle control, and repeated at least twice with independent cell cultures.

FIG. 13 shows Synergy of MIM1 and ABT-737 in the Context of Dual MCL-1 and BCL-X$_L$ Expression. Combination treatment with MIM1 and ABT-737 induces synergistic killing of parental p185$^+$Arf$^{-/-}$ CML cells that express both MCL-1 and BCL-X$_L$, as reflected by a leftward shift of the viability isotherm and the CalcuSyn dose effect curve, with calculated CI values of <1 at ED$_{50}$, ED$_{75}$, and ED$_{90}$. CI, combination index; ED, effective dose.

FIGS. 14A and 14B show MIM1/ABT-737 Synergy is Dependent on the Co-expression of MCL-1 and BCL-X$_L$, and thus does not Manifest in the Context of Exclusive MCL-1 or BCL-X$_L$ expression. (A) The addition of ABT-737 to MIM1 treatment of MCL-1-rescued p185$^+$Arf$^{-/-}$Mcl-1$^{-/-}$ CML cells had little to no additional cytotoxic effect, consistent with the relative inactivity of ABT-737 in the context of MCL-1-dependence. (B) Correspondingly, the addition of MIM1 to ABT-737 treatment of BCL-X$_L$-rescued p185$^+$Arf$^{-/-}$Mcl-1$^{-/-}$ CML cells provided no additional cytotoxic effect, consistent with the relative inactivity of MIM1 in the context of BCL-X$_L$-dependence. Data are mean±SEM for experiments performed in duplicate, normalized to vehicle control, and repeated at least twice with independent cell cultures.

FIGS. 15A, 15B, 15C, and 15D show Effect of MIM1 and ABT-737 on Mouse Embryonic Fibroblasts (MEFs). MIM1 and ABT-737 manifest little to no cytotoxicity (24 h) (A, B) or caspase 3/7 activation (8 h) (C, D) in wild-type or Bax$^{-/-}$Bak$^{-/-}$ MEFs, suggesting the potential of a therapeutic window for MIM1. Data are mean±SEM for experiments performed in duplicate and repeated at least twice with independent cell cultures with similar results.

FIG. 17 includes two graphs that show that compounds with enhanced binding activity to MCL-1 compared to MIM1 are more cytotoxic to MCL-1-dependent leukemia cells.

FIG. 18 includes two graphs that show that exemplary formula (I)/(II) compounds with variably enhanced MCL-1 binding activity exhibit a level of cytotoxicity in MCL-1-dependent leukemia cells that correlates with MCL-1 binding potency.

FIG. 19A and FIG. 19B are graphs that show potent targeting of the anti-apoptotic protein BFL-1/A1 by MIM1. FIG. 19A shows that FITC-BID BH3 directly binds to MCL-1ΔNΔC and BFL-1/A1ΔC with similar binding affinity. Thus, the complex between FITC-BID BH3 and BFL-1/A1ΔC was employed in a competitive FP assay to monitor the capacity of MIM1 to target BFL-1/A1ΔC. FIG. 19B shows that MIM1 manifests robust targeting of BFL1/A1ΔC, with effective competition in the nanomolar range.

FIGS. 20A and 20B shows exemplary formula (I)/(II) compounds that target both MCL-1 and BFL-1/A1 (20A) and that selectively target BFL-1/A1 (20B).

FIGS. 21A and 21B are graphs showing an example of an optimized compound with dual MCL-1 (20A) and BFL-1/A1 (20B) binding activity.

FIGS. 22A and 22B are graphs showing that select compounds of the formula (I)/(II) bind with high potency and selectivity to BFL-1/A1 (FIG. 22A), with little to no observed interaction with MCL-1 (FIG. 22B).

DETAILED DESCRIPTION

Figure 16:
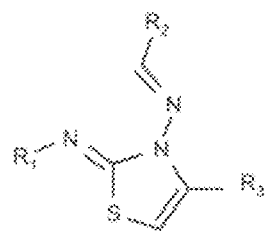
FIG. 16 shows exemplary formula (I) compounds.

This disclosure features compounds and pharmaceutically acceptable salts thereof that inhibit MCL-1 and/or BFL-1/A1 and compositions containing the same. This disclosure also features combinations that include one or more of the MCL-1/BFL-1/A inhibitor compounds described herein, or a pharmaceutically acceptable salt thereof; and one or more additional therapeutic agents (e.g., one or more chemotherapeutic agents (including but not limited to small molecule and/or anti-body based chemotherapy and/or radiation); e.g., one or more therapeutic agents that modulate apoptosis; e.g., one or more therapeutic agents that bind to and inhibit anti-apoptotic proteins or modulate them indirectly; e.g., one or more therapeutic agents that bind to and inhibit, or indirectly modulate, anti-apoptotic BCL-2, BCL-X$_L$, BCL-w, MCL-1, and/or BFL-1/A1; e.g., one or more therapeutic agents that directly bind to and inhibit anti-apoptotic BCL-2/BCL-X$_L$; e.g., agents such as ABT-199, ABT-263 and ABT-737; e.g., ABT-737), or (where applicable) a pharmaceutically acceptable salt of the one or more therapeutic agents (as well as compositions containing the same).

Also featured are methods of using any one or more of such MCL-1 and/or BFL-1/A1 inhibitor compounds, salts, combinations, and compositions, alone or in combination with other drugs e.g., for the treatment or prevention of diseases, disorders, and conditions associated with deregulated apoptosis of cells (e.g., diseased or damaged cells; e.g., insufficient apoptosis of diseased or damaged cells or reduced apoptosis of diseased or damaged cells) and/or other cancer treatment therapies (e.g., surgery, radiation).

The compounds, salts, combinations, and compositions described herein are therapeutically useful for treating (e.g., controlling, relieving, ameliorating, alleviating, or slowing the progression of) or preventing (e.g., delaying the onset of or reducing the risk of developing) diseases, disorders, and conditions associated with deregulated apoptosis of cells (e.g., diseased or damaged cells; e.g., insufficient apoptosis of diseased or damaged cells; or lack of apoptosis of diseased or damaged cells). Examples of such diseases, disorders, and conditions include (but are not limited to) those associated with blockade(s) of cell death pathways (e.g., over-expression of anti-apoptotic BCL-2 proteins; e.g., over-expression of anti-apoptotic BCL-2 proteins that fall outside of the inhibitory spectrum of a particular anti-apoptotic BCL-2 protein inhibitor, such as ABT-263 or ABT-737). Examples of such diseases, disorders, and conditions include hyperproliferative diseases, such as cancer.

While not wishing to be bound by theory, it is believed that the compounds, salts, combinations, and compositions described herein induce and increase apoptosis in target cells (e.g., pathogenic cells including, but not limited to, cancer cells), thereby suppressing tumor growth and/or proliferation. It is further believed that increasing apoptosis in such target cells reestablishes the normal apoptotic control that, during homeostasis, is associated with a regulated balance between pro- and anti-apoptotic protein functions.

Compounds

Formula (I) Compounds

In some embodiments, $R^{22}$ is aryl (e.g., phenyl), which is optionally substituted with from 1-5 (e.g., 1-3) independently selected Z (e.g., hydroxyl). In certain embodiments, $R^{22}$ is phenyl, which is optionally substituted with from 1-3 hydroxyl groups.

In some embodiments, $R^{23}$ is $C_1$-$C_8$ (e.g., $C_1$-$C_4$) alkyl; e.g., $CH_3$.

In some embodiments, $R^{24}$ is unsubstituted cycloalkyl or cycloalkyl (e.g., $C_3$-$C_7$) that is substituted with from 1-5 (e.g., 1-3) independently selected Z; e.g., unsubstituted cycloalkyl, e.g., cyclohexyl.

In some embodiments:

$R^{22}$ is aryl (e.g., phenyl), which is optionally substituted with from 1-5 (e.g., 1-3) independently selected Z (e.g., hydroxyl). In certain embodiments, $R^{22}$ is phenyl, which is optionally substituted with from 1-3 hydroxyl groups; and $R^{23}$ is $C_1$-$C_8$ (e.g., $C_1$-$C_4$) alkyl; e.g., $CH_3$; and $R^{24}$ is unsubstituted cycloalkyl or cycloalkyl (e.g., $C_3$-$C_7$) that is substituted with from 1-5 (e.g., 1-3) independently selected Z; e.g., unsubstituted cycloalkyl, e.g., cyclohexyl.

In certain embodiments, the compound is:

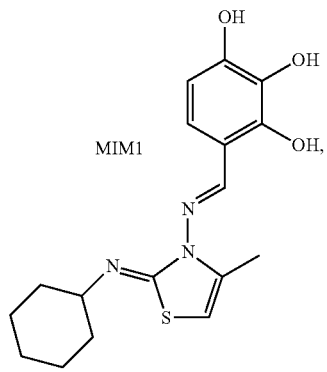

which is sometimes referred to herein as "MIM1."

Formula (II) Compounds

Variable $R^{22}$

In some embodiments, $R^{22}$ is $C_6$-$C_{10}$ (e.g., $C_6$) aryl, which is optionally substituted with from 1-5 (e.g., 1-3, e.g., 3) independently selected $R^a$.

In some embodiments, $R^{22}$ is $C_6$-$C_{10}$ (e.g., $C_6$) aryl, which is substituted with from 1-5 (e.g., 1-3, e.g., 3) independently selected $R^a$.

In certain embodiments, each $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In certain embodiments, each $R^a$ is independently selected from halo, hydroxyl, $C_1$-$C_6$ alkoxy; —NHC(O)($C_1$-$C_6$ alkyl); and C(O)OH.

In certain embodiments, one, two, or three (e.g., three) of the independently selected $R^a$ are hydroxyl.

In some embodiments, $R^{22}$ is $C_6$-$C_{10}$ (e.g., $C_6$) aryl, which is optionally substituted with from 1-5 (e.g., 1-3, e.g., 3) independently selected $R^a$, wherein three of the independently selected $R^a$ are hydroxyl.

In some embodiments, $R^{22}$ has formula (A):

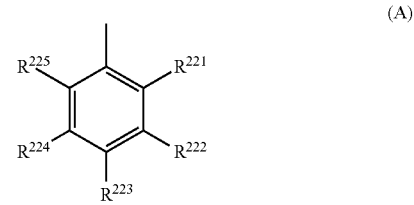

wherein:

one, two, or three (e.g., three) of $R^{221}$, $R^{222}$, $R^{223}$, $R^{224}$, and $R^{225}$ are each independently selected $R^a$, and the others are hydrogen.

In certain embodiments, each $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In certain embodiments, each $R^a$ is independently selected from halo, hydroxyl, $C_1$-$C_6$ alkoxy; —NHC(O)($C_1$-$C_6$ alkyl); and C(O)OH.

In certain embodiments, each $R^a$ is hydroxyl.

In certain embodiments, three of $R^{221}$, $R^{222}$, $R^{223}$, $R^{224}$, and $R^{225}$ are each independently selected $R^a$, and the other two are hydrogen.

For example, $R^{221}$, $R^{222}$, and $R^{223}$ can each be independently selected $R^a$, and $R^{224}$ and $R^{225}$ can be hydrogen.

In embodiments, $R^{221}$, $R^{222}$, and $R^{223}$ are each independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH. (e.g., e.g.,).

In embodiments, $R^{221}$, $R^{222}$, and $R^{223}$ are each independently selected from halo, hydroxyl, $C_1$-$C_6$ alkoxy; —NHC(O)($C_1$-$C_6$ alkyl); and C(O)OH.

In embodiments, $R^{221}$, $R^{222}$, and $R^{223}$ are each independently selected from halo and hydroxyl.

In embodiments, each of $R^{221}$, $R^{222}$, and $R^{223}$ is hydroxyl.

As another example, $R^{221}$, $R^{223}$, and $R^{224}$ are each independently selected $R^a$, and $R^{222}$ and $R^{225}$ are hydrogen.

In embodiments, $R^{221}$, $R^{223}$, and $R^{224}$ are each independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In embodiments, $R^{221}$, $R^{223}$, and $R^{224}$ are each independently selected from halo, hydroxyl, $C_1$-$C_6$ alkoxy; —NHC(O)($C_1$-$C_6$ alkyl); and C(O)OH.

In embodiments, $R^{221}$, $R^{223}$, and $R^{224}$ are each independently selected from halo and hydroxyl.

In embodiments, each of $R^{221}$, $R^{223}$, and $R^{224}$ is hydroxyl.

In embodiments, two of $R^{221}$, $R^{223}$, and $R^{224}$ (e.g., $R^{223}$ and $R^{224}$) are hydroxyl, and the other (e.g., $R^{221}$) is halo.

As a further example, $R^{222}$, $R^{223}$, and $R^{224}$ are each independently selected Ra, and $R^{221}$ and $R^{225}$ are hydrogen.

In embodiments, $R^{222}$, $R^{223}$, and $R^{224}$ are each independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In embodiments, $R^{222}$, $R^{223}$, and $R^{224}$ are each independently selected from halo, hydroxyl, $C_1$-$C_6$ alkoxy; —NHC(O)($C_1$-$C_6$ alkyl); and C(O)OH.

In embodiments, $R^{222}$, $R^{223}$, and $R^{224}$ are each independently selected from halo and hydroxyl.

In embodiments, each of $R^{222}$, $R^{223}$, and $R^{224}$ is hydroxyl.

In certain embodiments, two of $R^{221}$, $R^{222}$, $R^{223}$, $R^{224}$, and $R^{225}$ (e.g., $R^{222}$ and $R^{223}$; $R^{221}$ and $R^{222}$; or $R^{221}$ and $R^{223}$) are each independently selected $R^a$, and the other three are hydrogen.

In embodiments, each $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In embodiments, each $R^a$ is independently selected from halo, hydroxyl, $C_1$-$C_6$ alkoxy; —NHC(O)($C_1$-$C_6$ alkyl); and C(O)OH.

In embodiments, each $R^a$ is hydroxyl.

In certain embodiments, one of $R^{221}$, $R^{222}$, $R^{223}$, $R^{224}$, and $R^{225}$ (e.g., $R^{223}$) is $R^a$, and the other four are hydrogen.

In embodiments, $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In embodiments, $R^a$ is independently selected from halo, hydroxyl, $C_1$-$C_6$ alkoxy; —NHC(O)($C_1$-$C_6$ alkyl); and C(O)OH.

In embodiments, $R^a$ is hydroxyl.

Variable $R^{23}$

In some embodiments, $R^{23}$ is:
(i) $C_1$-$C_8$ alkyl or $C_1$-$C_8$ haloalkyl, each of which is optionally substituted with from 1-2 independently selected $R^b$;
(ii) phenyl that is optionally substituted with from independently selected 1-4 $R^c$;
(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 independently selected $R^c$;
(iv) $C_3$-$C_6$ cycloalkyl or $C_3$-$C_6$ cycloalkenyl, each of which is optionally substituted with from 1-4 independently selected $R^d$; or
(v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

In some embodiments, $R^{23}$ is:
(i) $C_3$-$C_6$ cycloalkyl or $C_3$-$C_6$ cycloalkenyl, each of which is optionally substituted with from 1-4 independently selected $R^d$; or
(ii) $C_1$-$C_8$ alkyl or $C_1$-$C_8$ haloalkyl, each of which is optionally substituted with from 1-2 independently selected $R^b$;

In some embodiments, $R^{23}$ is $C_3$-$C_6$ cycloalkyl or $C_3$-$C_6$ cycloalkenyl, each of which is optionally substituted with from 1-4 independently selected $R^d$.

In some embodiments, $R^{23}$ is $C_3$-$C_6$ cycloalkyl (e.g., cyclopropyl), which is optionally substituted with from 1-4 independently selected $R^d$ (e.g., $C_1$-$C_6$ alkyl, $C_1$-$C_3$ alkyl).

In certain embodiments, $R^{23}$ is unsubstituted $C_3$-$C_6$ cycloalkyl (e.g., cyclopropyl).

In certain embodiments, $R^{23}$ is unsubstituted cyclopropyl.

In some embodiments, $R^{23}$ is $C_1$-$C_8$ alkyl or $C_1$-$C_8$ haloalkyl, each of which is optionally substituted with from 1-2 independently selected $R^b$.

In some embodiments, $R^{23}$ is $C_1$-$C_8$ alkyl, which is optionally substituted with from 1-2 independently selected $R^b$.

In some embodiments, $R^{23}$ is $C_1$-$C_3$ (e.g., $C_1$-$C_2$) alkyl, which is optionally substituted with from 1-2 independently selected $R^b$.

In some embodiments, $R^{23}$ is $C_2$-$C_8$ alkyl (e.g., tert-butyl), which is optionally substituted with from 1-2 independently selected $R^b$.

In some embodiments, $R^{23}$ is $C_3$-$C_8$ alkyl (e.g., tert-butyl), which is optionally substituted with from 1-2 independently selected $R^b$.

In certain embodiments, $R^{23}$ is straight chain $C_3$-$C_8$ alkyl, which is optionally substituted with from 1-2 independently selected $R^b$.

In certain embodiments, $R^{23}$ is branched $C_3$-$C_8$ alkyl (e.g., tert-butyl), which is optionally substituted with from 1-2 independently selected $R^b$.

In some embodiments, $R^{23}$ is $C_4$-$C_8$ alkyl, which is optionally substituted with from 1-2 independently selected $R^b$.

In certain embodiments, $R^{23}$ is straight chain $C_4$-$C_8$ alkyl, which is optionally substituted with from 1-2 independently selected $R^b$.

In certain embodiments, $R^{23}$ is branched $C_4$-$C_8$ alkyl (e.g., tert-butyl), which is optionally substituted with from 1-2 independently selected $R^b$.

In some embodiments, $R^{23}$ is unsubstituted $C_1$-$C_8$ alkyl (e.g., unsubstituted $C_2$-$C_8$ alkyl, unsubstituted $C_3$-$C_8$ alkyl, unsubstituted branched $C_3$-$C_8$ alkyl, unsubstituted branched $C_4$-$C_8$ alkyl).

In certain embodiments, $R^{23}$ is $CH_3$.

In certain embodiments, $R^{23}$ is tert-butyl.

In some embodiments, $R^{23}$ is heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 independently selected $R^c$ (e.g., thienyl).

Variable $R^{24}$

In some embodiments, $R^{24}$ is:

(i) $C_3$-$C_{10}$ (e.g., $C_3$-$C_8$) cycloalkyl or $C_3$-$C_{10}$ (e.g., $C_3$-$C_8$) cycloalkenyl, each of which is optionally substituted with from 1-4 independently selected $R^d$;

(ii) $C_6$-$C_{10}$ aryl, which is optionally substituted with from 1-5 independently selected $R^c$;

(iii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^c$;

(iv) unsubstituted $C_1$-$C_8$ alkyl or unsubstituted $C_1$-$C_8$ haloalkyl; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

In some embodiments, $R^{24}$ is:

(i) $C_3$-$C_{10}$ (e.g., $C_3$-$C_8$) cycloalkyl or $C_3$-$C_{10}$ (e.g., $C_3$-$C_8$) cycloalkenyl, each of which is optionally substituted with from 1-4 independently selected $R^d$;

(ii) $C_6$-$C_{10}$ aryl, which is optionally substituted with from 1-5 independently selected $R^c$;

(iii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^c$;

(iv) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

In some embodiments, $R^{24}$ is:

(i) $C_3$-$C_{10}$ (e.g., $C_3$-$C_8$) cycloalkyl or $C_3$-$C_{10}$ (e.g., $C_3$-$C_8$) cycloalkenyl, each of which is optionally substituted with from 1-4 independently selected $R^d$; or (ii) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

In some embodiments, $R^{24}$ is:

(i) $C_6$-$C_{10}$ aryl, which is optionally substituted with from 1-5 independently selected $R^c$; or (ii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^c$;

In some embodiments, $R^{24}$ is $C_3$-$C_{10}$ (e.g., $C_3$-$C_8$) cycloalkyl or $C_3$-$C_{10}$ (e.g., $C_3$-$C_8$) cycloalkenyl, each of which is optionally substituted with from 1-4 independently selected $R^d$.

In certain embodiments, $R^d$ at each occurrence is, independently, selected from any one the substituents delineated collectively in (a) and/or (b) below:

(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —NH$_2$, or —SH; or (b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), —NHSO$_2$($C_1$-$C_6$ alkyl).

In certain embodiments, $R^d$ at each occurrence is, independently, selected from any one the substituents delineated collectively in (a) (e.g., $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl).

In certain embodiments, $R^d$ at each occurrence is, independently, selected from any one the substituents delineated collectively in (a) (e.g., $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl); halo; and —OH.

In some embodiments, $R^{24}$ is $C_3$-$C_{10}$ (e.g., $C_3$-$C_8$) cycloalkyl, which is optionally substituted with from 1-4 independently selected $R^d$ (as defined above or anywhere herein).

In certain embodiments, $R^{24}$ is unsubstituted $C_3$-$C_{10}$ (e.g., $C_3$-$C_8$) cycloalkyl.

In certain embodiments, $R^{24}$ is $C_3$-$C_8$ (e.g., $C_3$-$C_6$, e.g., $C_6$) cycloalkyl, which is optionally substituted with from 1-4 independently selected $R^d$ (as defined above or anywhere herein).

In certain embodiments, $R^{24}$ is unsubstituted $C_3$-$C_8$ (e.g., $C_3$-$C_6$, e.g., $C_6$) cycloalkyl.

In certain embodiments, $R^{24}$ is cyclohexyl.

In some embodiments, $R^{24}$ is $C_6$-$C_{10}$ aryl (e.g., phenyl), which is optionally substituted with from 1-5 independently selected $R^c$.

In certain embodiments, $R^{24}$ is unsubstituted $C_6$-$C_{10}$ aryl (e.g., phenyl).

In some embodiments, $R^{24}$ is unsubstituted $C_1$-$C_8$ alkyl or unsubstituted $C_1$-$C_8$ haloalkyl (e.g., unsubstituted $C_1$-$C_8$ alkyl; e.g., unsubstituted $C_3$-$C_8$ alkyl; e.g., unsubstituted branched $C_3$-$C_8$ alkyl).

In some embodiments, $R^{24}$ is heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

In certain embodiments, $R^{24}$ is piperidinyl.

Variables $R^{25}$, $R^{26}$, and $R^{27}$

In some embodiments, $R^{26}$ and $R^{27}$ together are a bond.

In some embodiments, $R^{25}$ is:

(i) hydrogen;

(ii) $C_1$-$C_8$ alkyl or $C_1$-$C_8$ haloalkyl, each of which is optionally substituted with from 1-2 independently selected $R^b$;

(iii) $C_3$-$C_6$ cycloalkyl or $C_3$-$C_6$ cycloalkenyl, each of which is optionally substituted with from 1-4 independently selected $R^d$; or (iv) —C(O)O($C_1$-$C_6$ alkyl).

In some embodiments, $R^{25}$ is hydrogen.

In some embodiments, $R^{25}$ is a substituent other than hydrogen, such as $C_1$-$C_8$ alkyl or $C_1$-$C_8$ haloalkyl, each of which is optionally substituted with from 1-2 independently selected $R^b$; or —C(O)O($C_1$-$C_6$ alkyl).

In certain embodiments, $R^{25}$ is $C_1$-$C_8$ alkyl, which is optionally substituted with from 1-2 independently selected $R^b$.

In certain embodiments, $R^{25}$ is unsubstituted $C_1$-$C_8$ alkyl (e.g., $C_1$-$C_3$ alkyl, e.g., $CH_3$).

Non-limiting Combinations

[A] In some embodiments:
$R^{26}$ and $R^{27}$ together are a bond;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl).

[B] In some embodiments:
$R^{23}$ is:
(i) $C_1$-$C_8$ alkyl or $C_1$-$C_8$ haloalkyl, each of which is optionally substituted with from 1-2 independently selected $R^b$;
(ii) phenyl that is optionally substituted with from independently selected 1-4 $R^c$;
(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 independently selected $R^c$;
(iv) $C_3$-$C_6$ cycloalkyl or $C_3$-$C_6$ cycloalkenyl, each of which is optionally substituted with from 1-4 independently selected $R^d$; or
(v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl).

[C] In some embodiments:
$R^{26}$ and $R^{27}$ together are a bond;
and
$R^{23}$ is:
(i) $C_1$-$C_8$ alkyl or $C_1$-$C_8$ haloalkyl, each of which is optionally substituted with from 1-2 independently selected $R^b$;
(ii) phenyl that is optionally substituted with from independently selected 1-4 $R^c$;
(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 independently selected $R^c$;
(iv) $C_3$-$C_6$ cycloalkyl or $C_3$-$C_6$ cycloalkenyl, each of which is optionally substituted with from 1-4 independently selected $R^d$; or
(v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl).

[D] In some embodiments:
$R^{22}$ is $C_6$-$C_{10}$ (e.g., $C_6$) aryl, which is substituted with from 1-5 (e.g., 1-3, e.g., 3) independently selected $R^a$ (e.g., hydroxyl);
and
$R^{23}$ is:
(i) $C_3$-$C_6$ cycloalkyl or $C_3$-$C_6$ cycloalkenyl, each of which is optionally substituted with from 1-4 independently selected $R^d$;
(ii) branched $C_3$-$C_8$ alkyl or $C_1$-$C_8$ haloalkyl, each of which is optionally substituted with from 1-2 independently selected $R^b$; or
(iii) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl);
and
$R^{26}$ and $R^{27}$ together are a bond (form a second or double bond between the carbon atoms to which each is attached);
and
$R^{24}$ is:
(i) $C_3$-$C_{10}$ cycloalkyl or $C_3$-$C_{10}$ cycloalkenyl, each of which is optionally substituted with from 1-4 independently selected $R^d$;
(ii) $C_6$-$C_{10}$ aryl, which is optionally substituted with from 1-5 independently selected $R^c$;
(iii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^c$;
(iv) unsubstituted $C_1$-$C_8$ alkyl or unsubstituted $C_1$-$C_8$ haloalkyl; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

[E] In some embodiments:

$R^{22}$ is $C_6$-$C_{10}$ (e.g., $C_6$) aryl, which is substituted with from 1-5 (e.g., 1-3, e.g., 3) independently selected $R^a$ (e.g., hydroxyl);

and $R^{23}$ is:

(i) $C_3$-$C_6$ cycloalkyl or $C_3$-$C_6$ cycloalkenyl, each of which is optionally substituted with from 1-4 independently selected $R^d$;

(ii) branched $C_3$-$C_8$ alkyl or $C_1$-$C_8$ haloalkyl, each of which is optionally substituted with from 1-2 independently selected $R^b$; or and $R^{25}$ is:

(i) hydrogen;

(ii) $C_1$-$C_8$ alkyl or $C_1$-$C_8$ haloalkyl, each of which is optionally substituted with from 1-2 independently selected $R^b$;

(iii) $C_3$-$C_6$ cycloalkyl or $C_3$-$C_6$ cycloalkenyl, each of which is optionally substituted with from 1-4 independently selected $R^d$; or (iv) —C(O)O($C_1$-$C_6$ alkyl);

and $R^{26}$ and $R^{27}$ together are a bond (form a second or double bond between the carbon atoms to which each is attached);

and $R^{24}$ is:

(i) $C_3$-$C_{10}$ cycloalkyl or $C_3$-$C_{10}$ cycloalkenyl, each of which is optionally substituted with from 1-4 independently selected $R^d$;

(ii) $C_6$-$C_{10}$ aryl, which is substituted with from 1-5 independently selected $R^c$;

(iii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-4 independently selected $R^c$;

(iv) unsubstituted $C_1$-$C_8$ alkyl or unsubstituted $C_1$-$C_8$ haloalkyl; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

[F] In some embodiments:

$R^{22}$ is $C_6$-$C_{10}$ (e.g., $C_6$) aryl, which is substituted with from 1-5 (e.g., 1-3, e.g., 3) independently selected Ra (e.g., hydroxyl);

and $R^{23}$ is:

(i) $C_1$-$C_8$ alkyl or $C_1$-$C_8$ haloalkyl, each of which is optionally substituted with from 1-2 independently selected $R^b$;

(ii) phenyl that is optionally substituted with from independently selected 1-4 $R^c$;

(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from independently selected 1-3 $R^c$; or (iv) $C_3$-$C_6$ cycloalkyl or $C_3$-$C_6$ cycloalkenyl, each of which is optionally substituted with from 1-4 independently selected $R^d$; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;

and $R^{25}$ is:

(i) hydrogen;

(ii) $C_1$-$C_8$ alkyl or $C_1$-$C_8$ haloalkyl, each of which is optionally substituted with from 1-2 independently selected $R^b$;

(iii) $C_3$-$C_6$ cycloalkyl or $C_3$-$C_6$ cycloalkenyl, each of which is optionally substituted with from 1-4 independently selected $R^d$; or (iv) —C(O)O($C_1$-$C_6$ alkyl);

and $R^{26}$ and $R^{27}$ together are a bond (form a second or double bond between the carbon atoms to which each is attached);

and $R^{24}$ is:

(i) $C_3$-$C_{10}$ cycloalkyl or $C_3$-$C_{10}$ cycloalkenyl, each of which is optionally substituted with from 1-4 independently selected $R^d$; or (ii) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$.

[G] In some embodiments:

$R^{22}$ is $C_6$-$C_{10}$ (e.g., $C_6$) aryl, which is substituted with from 1-5 (e.g., 1-3, e.g., 3) independently selected $R^a$ (e.g., hydroxyl);

and $R^{23}$ is:

(i) $C_1$-$C_8$ alkyl or $C_1$-$C_8$ haloalkyl, each of which is optionally substituted with from 1-2 independently selected $R^b$;

(ii) phenyl that is optionally substituted with from independently selected 1-4 $R^c$;

(iii) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from independently selected 1-3 $R^c$; or (iv) $C_3$-$C_6$ cycloalkyl or $C_3$-$C_6$ cycloalkenyl, each of which is optionally substituted with from 1-4 independently selected $R^d$; or (v) heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$;

and $R^{25}$ is:

(i) hydrogen;

(ii) $C_1$-$C_8$ alkyl or $C_1$-$C_8$ haloalkyl, each of which is optionally substituted with from 1-2 independently selected $R^b$;

(iii) $C_3$-$C_6$ cycloalkyl or $C_3$-$C_6$ cycloalkenyl, each of which is optionally substituted with from 1-4 independently selected $R^d$; or (iv) —C(O)O($C_1$-$C_6$ alkyl);
and
$R^{26}$ and $R^{27}$ together are a bond (form a second or double bond between the carbon atoms to which each is attached);
and
$R^{24}$ is $C_3$-$C_{10}$ cycloalkyl or $C_3$-$C_{10}$ cycloalkenyl, each of which is optionally substituted with from 1-4 independently selected $R^d$.

[H] In some embodiments:
$R^{22}$ is $C_6$-$C_{10}$ (e.g., $C_6$) aryl, which is substituted with from 1-5 (e.g., 1-3, e.g., 3) independently selected $R^a$ (e.g., hydroxyl);
and
$R^{23}$ is $C_3$-$C_6$ cycloalkyl or $C_3$-$C_6$ cycloalkenyl, each of which is optionally substituted with from 1-4 independently selected $R^d$;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl);
and
$R^{26}$ and $R^{27}$ together are a bond (form a second or double bond between the carbon atoms to which each is attached);
and
$R^{24}$ is $C_3$-$C_{10}$ cycloalkyl or $C_3$-$C_{10}$ cycloalkenyl, each of which is optionally substituted with from 1-4 independently selected $R^d$.

In some embodiments, $R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are each independently selected $R^a$, and the others are hydrogen.

In certain embodiments, each of the three $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In certain embodiments, each of the three $R^a$ is independently selected from halo, hydroxyl, $C_1$-$C_6$ alkoxy; —NHC(O)($C_1$-$C_6$ alkyl); and C(O)OH.

In certain embodiments, each of the three $R^a$ is hydroxyl.

In some embodiments, $R^{25}$ is hydrogen.

In some embodiments, $R^{25}$ is a substituent other than hydrogen, such as $C_1$-$C_8$ alkyl or $C_1$-$C_8$ haloalkyl, each of which is optionally substituted with from 1-2 independently selected $R^b$.

In certain embodiments, $R^{25}$ is $C_1$-$C_8$ alkyl, which is optionally substituted with from 1-2 independently selected $R^b$.

In certain embodiments, $R^{25}$ is unsubstituted $C_1$-$C_8$ alkyl (e.g., $C_1$-$C_3$ alkyl, e.g., $CH_3$).

In some embodiments, $R^{23}$ is $C_3$-$C_6$ cycloalkyl (e.g., cyclopropyl), which is optionally substituted with from 1-4 independently selected $R^d$ (e.g., $C_1$-$C_6$ alkyl, $C_1$-$C_3$ alkyl).

In some embodiments, $R^{24}$ is $C_3$-$C_8$ (e.g., $C_3$-$C_6$, e.g., $C_6$) cycloalkyl, which is optionally substituted with from 1-4 independently selected $R^d$ (as defined above or anywhere herein).

[I] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are each independently selected $R^a$, and the others are hydrogen (e.g., each of the three $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH; e.g., each of the three $R^a$ is independently selected from halo, hydroxyl, $C_1$-$C_6$ alkoxy; —NHC(O)($C_1$-$C_6$ alkyl); and C(O)OH; e.g., each of the three $R^a$ is hydroxyl);
and
$R^{23}$ is $C_3$-$C_6$ cycloalkyl or $C_3$-$C_6$ cycloalkenyl (e.g., $C_3$-$C_6$ cycloalkyl), each of which is optionally substituted with from 1-4 independently selected $R^d$;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$;
and
$R^{26}$ and $R^{27}$ together are a bond (form a second or double bond between the carbon atoms to which each is attached);
and
$R^{24}$ is $C_3$-$C_{10}$ cycloalkyl or $C_3$-$C_{10}$ cycloalkenyl (e.g., $C_3$-$C_{10}$ cycloalkyl), each of which is optionally substituted with from 1-4 independently selected $R^d$.

In some embodiments, $R^{25}$ is hydrogen.

In some embodiments, $R^{25}$ is $C_1$-$C_8$ alkyl or $C_1$-$C_8$ haloalkyl, each of which is optionally substituted with from 1-2 independently selected $R^b$.

In certain embodiments, $R^{25}$ is $C_1$-$C_8$ alkyl, which is optionally substituted with from 1-2 independently selected $R^b$.

In certain embodiments, $R^{25}$ is unsubstituted $C_1$-$C_8$ alkyl (e.g., $C_1$-$C_3$ alkyl, e.g., $CH_3$).

In some embodiments, $R^{23}$ is $C_3$-$C_6$ cycloalkyl (e.g., cyclopropyl), which is optionally substituted with from 1-4 independently selected $R^d$ (e.g., $C_1$-$C_6$ alkyl, $C_1$-$C_3$ alkyl).

In some embodiments, $R^{24}$ is $C_3$-$C_8$ (e.g., $C_3$-$C_6$, e.g., $C_6$) cycloalkyl, which is optionally substituted with from 1-4 independently selected $R^d$ (as defined above or anywhere herein).

[J] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are hydroxyl, and the others are hydrogen;
and
$R^{23}$ is $C_3$-$C_6$ cycloalkyl or $C_3$-$C_6$ cycloalkenyl (e.g., $C_3$-$C_6$ cycloalkyl), each of which is optionally substituted with from 1-4 independently selected $R^d$;
and
$R^{25}$ is:
(i) hydrogen; or
(ii) $C_1$-$C_8$ alkyl, which is optionally substituted with from 1-2 independently selected $R^b$;
and
$R^{26}$ and $R^{27}$ together are a bond (form a second or double bond between the carbon atoms to which each is attached);
and
$R^{24}$ is $C_3$-$C_{10}$ cycloalkyl or $C_3$-$C_{10}$ cycloalkenyl (e.g., $C_3$-$C_{10}$ cycloalkyl), each of which is optionally substituted with from 1-4 independently selected $R^d$.

In some embodiments, $R^{25}$ is hydrogen.

In some embodiments, $R^{25}$ is $C_1$-$C_8$ alkyl or $C_1$-$C_8$ haloalkyl, each of which is optionally substituted with from 1-2 independently selected $R^b$.

In certain embodiments, $R^{25}$ is $C_1$-$C_8$ alkyl, which is optionally substituted with from 1-2 independently selected $R^b$.

In certain embodiments, $R^{25}$ is unsubstituted $C_1$-$C_8$ alkyl (e.g., $C_1$-$C_3$ alkyl, e.g., $CH_3$).

In some embodiments, $R^{23}$ is $C_3$-$C_6$ cycloalkyl (e.g., cyclopropyl), which is optionally substituted with from 1-4 independently selected $R^d$ (e.g., $C_1$-$C_6$ alkyl, $C_1$-$C_3$ alkyl).

In some embodiments, $R^{24}$ is $C_3$-$C_8$ (e.g., $C_3$-$C_6$, e.g., $C_6$) cycloalkyl, which is optionally substituted with from 1-4 independently selected $R^d$ (as defined above or anywhere herein).

[K] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are hydroxyl, and the others are hydrogen;
and
$R^{23}$ is $C_3$-$C_6$ cycloalkyl, which is optionally substituted with from 1-4 independently selected $R^d$;
and
$R^{25}$ is hydrogen; or $C_1$-$C_3$ alkyl (e.g., $CH_3$);
and
$R^{26}$ and $R^{27}$ together are a bond (form a second or double bond between the carbon atoms to which each is attached);
and
$R^{24}$ is $C_3$-$C_{10}$ cycloalkyl, which is optionally substituted with from 1-4 independently selected $R^d$.

In some embodiments, $R^{25}$ is hydrogen.

In certain embodiments, $R^{25}$ is unsubstituted $C_1$-$C_3$ alkyl, e.g., $CH_3$.

In some embodiments, $R^{23}$ is cyclopropyl, which is optionally substituted with from 1-4 independently selected $R^d$ (e.g., $C_1$-$C_6$ alkyl, $C_1$-$C_3$ alkyl).

In some embodiments, $R^{24}$ is cyclohexyl, which is optionally substituted with from 1-4 independently selected $R^d$ (as defined above or anywhere herein).

[L] In some embodiments:
$R^{22}$ is $C_6$-$C_{10}$ (e.g., $C_6$) aryl, which is substituted with from 1-5 (e.g., 1-3, e.g., 3) independently selected $R^a$ (e.g., hydroxyl);
and
$R^{23}$ is $C_1$-$C_8$ alkyl or $C_1$-$C_8$ haloalkyl, each of which is optionally substituted with from 1-2 independently selected $R^b$;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl);
and
$R^{26}$ and $R^{27}$ together are a bond (form a second or double bond between the carbon atoms to which each is attached);
and
$R^{24}$ is $C_3$-$C_{10}$ cycloalkyl or $C_3$-$C_{10}$ cycloalkenyl, each of which is optionally substituted with from 1-4 independently selected $R^d$.

In some embodiments, $R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are each independently selected $R^a$, and the others are hydrogen.

In certain embodiments, each of the three $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

In certain embodiments, each of the three $R^a$ is independently selected from halo, hydroxyl, $C_1$-$C_6$ alkoxy; —NHC(O)($C_1$-$C_6$ alkyl); and C(O)OH.

In certain embodiments, each of the three $R^a$ is hydroxyl.

In some embodiments, $R^{25}$ is hydrogen.

In some embodiments, $R^{25}$ is a substituent other than hydrogen, such as $C_1$-$C_8$ alkyl or $C_1$-$C_8$ haloalkyl, each of which is optionally substituted with from 1-2 independently selected $R^b$.

In certain embodiments, $R^{25}$ is $C_1$-$C_8$ alkyl, which is optionally substituted with from 1-2 independently selected $R^b$.

In certain embodiments, $R^{25}$ is unsubstituted $C_1$-$C_8$ alkyl (e.g., $C_1$-$C_3$ alkyl, e.g., $CH_3$).

In some embodiments, $R^{24}$ is $C_3$-$C_8$ (e.g., $C_3$-$C_6$, e.g., $C_6$) cycloalkyl, which is optionally substituted with from 1-4 independently selected $R^d$ (as defined above or anywhere herein).

In some embodiments, $R^{23}$ is $C_1$-$C_8$ alkyl, which is optionally substituted with from 1-2 independently selected $R^b$.

In some embodiments, $R^{23}$ is $C_1$-$C_3$ (e.g., $C_1$-$C_2$) alkyl, which is optionally substituted with from 1-2 independently selected $R^b$.

In some embodiments, $R^{23}$ is $C_2$-$C_8$ alkyl (e.g., tert-butyl), which is optionally substituted with from 1-2 independently selected $R^b$.

In some embodiments, $R^{23}$ is $C_3$-$C_8$ alkyl (e.g., tert-butyl), which is optionally substituted with from 1-2 independently selected $R^b$.

In certain embodiments, $R^{23}$ is straight chain $C_3$-$C_8$ alkyl, which is optionally substituted with from 1-2 independently selected $R^b$.

In certain embodiments, $R^{23}$ is branched $C_3$-$C_8$ alkyl (e.g., tert-butyl), which is optionally substituted with from 1-2 independently selected $R^b$.

In some embodiments, $R^{23}$ is $C_4$-$C_8$ alkyl, which is optionally substituted with from 1-2 independently selected $R^b$.

In certain embodiments, $R^{23}$ is straight chain $C_4$-$C_8$ alkyl, which is optionally substituted with from 1-2 independently selected $R^b$.

In certain embodiments, $R^{23}$ is branched $C_4$-$C_8$ alkyl (e.g., tert-butyl), which is optionally substituted with from 1-2 independently selected $R^b$.

In some embodiments, $R^{23}$ is unsubstituted $C_1$-$C_8$ alkyl (e.g., unsubstituted $C_2$-$C_8$ alkyl, unsubstituted $C_3$-$C_8$ alkyl, unsubstituted branched $C_3$-$C_8$ alkyl, unsubstituted branched $C_4$-$C_8$ alkyl).

In certain embodiments, $R^{23}$ is $CH_3$.

In certain embodiments, $R^{23}$ is tert-butyl.

[M] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are each independently selected $R^a$, and the others are hydrogen (e.g., each of the three $R^a$ is independently selected from halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH; e.g., each of the three $R^a$ is independently selected from halo, hydroxyl, $C_1$-$C_6$ alkoxy; —NHC(O)($C_1$-$C_6$ alkyl); and C(O)OH; e.g., each of the three $R^a$ is hydroxyl);
and
$R^{23}$ is $C_1$-$C_8$ alkyl or $C_1$-$C_8$ haloalkyl (e.g., $C_1$-$C_8$ alkyl), each of which is optionally substituted with from 1-2 independently selected $R^b$;
and
$R^{25}$ is:
(i) hydrogen;
(ii) $C_1$-$C_8$ alkyl or $C_1$-$C_8$ haloalkyl, each of which is optionally substituted with from 1-2 independently selected $R^b$; or
(iv) —C(O)O($C_1$-$C_6$ alkyl);
and
$R^{26}$ and $R^{27}$ together are a bond (form a second or double bond between the carbon atoms to which each is attached);
and
$R^{24}$ is $C_3$-$C_{10}$ cycloalkyl or $C_3$-$C_{10}$ cycloalkenyl (e.g., $C_3$-$C_{10}$ cycloalkyl), each of which is optionally substituted with from 1-4 independently selected $R^d$.

In some embodiments, $R^{25}$ is hydrogen.

In some embodiments, $R^{25}$ is $C_1$-$C_8$ alkyl or $C_1$-$C_8$ haloalkyl, each of which is optionally substituted with from 1-2 independently selected $R^b$.

In certain embodiments, $R^{25}$ is $C_1$-$C_8$ alkyl, which is optionally substituted with from 1-2 independently selected $R^b$.

In certain embodiments, $R^{25}$ is unsubstituted $C_1$-$C_8$ alkyl (e.g., $C_1$-$C_3$ alkyl, e.g., $CH_3$).

In some embodiments, $R^{24}$ is $C_3$-$C_8$ (e.g., $C_3$-$C_6$, e.g., $C_6$) cycloalkyl, which is optionally substituted with from 1-4 independently selected $R^d$ (as defined above or anywhere herein).

In some embodiments, $R^{23}$ is $C_1$-$C_8$ alkyl, which is optionally substituted with from 1-2 independently selected $R^b$.

In some embodiments, $R^{23}$ is $C_1$-$C_3$ (e.g., $C_1$-$C_2$) alkyl, which is optionally substituted with from 1-2 independently selected $R^b$.

In some embodiments, $R^{23}$ is $C_2$-$C_8$ alkyl (e.g., tert-butyl), which is optionally substituted with from 1-2 independently selected $R^b$.

In some embodiments, $R^{23}$ is $C_3$-$C_8$ alkyl (e.g., tert-butyl), which is optionally substituted with from 1-2 independently selected $R^b$.

In certain embodiments, $R^{23}$ is straight chain $C_3$-$C_8$ alkyl, which is optionally substituted with from 1-2 independently selected $R^b$.

In certain embodiments, $R^{23}$ is branched $C_3$-$C_8$ alkyl (e.g., tert-butyl), which is optionally substituted with from 1-2 independently selected $R^b$.

In some embodiments, $R^{23}$ is $C_4$-$C_8$ alkyl, which is optionally substituted with from 1-2 independently selected $R^b$.

In certain embodiments, $R^{23}$ is straight chain $C_4$-$C_8$ alkyl, which is optionally substituted with from 1-2 independently selected $R^b$.

In certain embodiments, $R^{23}$ is branched $C_4$-$C_8$ alkyl (e.g., tert-butyl), which is optionally substituted with from 1-2 independently selected $R^b$.

In some embodiments, $R^{23}$ is unsubstituted $C_1$-$C_8$ alkyl (e.g., unsubstituted $C_2$-$C_8$ alkyl, unsubstituted $C_3$-$C_8$ alkyl, unsubstituted branched $C_3$-$C_8$ alkyl, unsubstituted branched $C_4$-$C_8$ alkyl).

In certain embodiments, $R^{23}$ is $CH_3$.
In certain embodiments, $R^{23}$ is tert-butyl.

[N] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are hydroxyl, and the others are hydrogen;
and
$R^{23}$ is $C_1$-$C_8$ alkyl or $C_1$-$C_8$ haloalkyl (e.g., $C_1$-$C_8$ alkyl), each of which is optionally substituted with from 1-2 independently selected $R^b$;
and
$R^{25}$ is:
(i) hydrogen; or
(ii) $C_1$-$C_8$ alkyl, which is optionally substituted with from 1-2 independently selected $R^b$; or
(iv) —C(O)O($C_1$-$C_6$ alkyl);
and
$R^{26}$ and $R^{27}$ together are a bond (form a second or double bond between the carbon atoms to which each is attached);
and
$R^{24}$ is $C_3$-$C_{10}$ cycloalkyl or $C_3$-$C_{10}$ cycloalkenyl (e.g., $C_3$-$C_{10}$ cycloalkyl), each of which is optionally substituted with from 1-4 independently selected $R^d$.

In some embodiments, $R^{25}$ is hydrogen.

In some embodiments, $R^{25}$ is $C_1$-$C_8$ alkyl or $C_1$-$C_8$ haloalkyl, each of which is optionally substituted with from 1-2 independently selected $R^b$.

In certain embodiments, $R^{25}$ is $C_1$-$C_8$ alkyl, which is optionally substituted with from 1-2 independently selected $R^b$.

In certain embodiments, $R^{25}$ is unsubstituted $C_1$-$C_8$ alkyl (e.g., $C_1$-$C_3$ alkyl, e.g., $CH_3$).

In some embodiments, $R^{24}$ is $C_3$-$C_8$ (e.g., $C_3$-$C_6$, e.g., $C_6$) cycloalkyl, which is optionally substituted with from 1-4 independently selected $R^d$ (as defined above or anywhere herein).

In some embodiments, $R^{23}$ is $C_1$-$C_8$ alkyl, which is optionally substituted with from 1-2 independently selected $R^b$.

In some embodiments, $R^{23}$ is $C_1$-$C_3$ (e.g., $C_1$-$C_2$) alkyl, which is optionally substituted with from 1-2 independently selected $R^b$.

In some embodiments, $R^{23}$ is $C_2$-$C_8$ alkyl (e.g., tert-butyl), which is optionally substituted with from 1-2 independently selected $R^b$.

In some embodiments, $R^{23}$ is $C_3$-$C_8$ alkyl (e.g., tert-butyl), which is optionally substituted with from 1-2 independently selected $R^b$.

In certain embodiments, $R^{23}$ is straight chain $C_3$-$C_8$ alkyl, which is optionally substituted with from 1-2 independently selected $R^b$.

In certain embodiments, $R^{23}$ is branched $C_3$-$C_8$ alkyl (e.g., tert-butyl), which is optionally substituted with from 1-2 independently selected $R^b$.

In some embodiments, $R^{23}$ is $C_4$-$C_8$ alkyl, which is optionally substituted with from 1-2 independently selected $R^b$.

In certain embodiments, $R^{23}$ is straight chain $C_4$-$C_8$ alkyl, which is optionally substituted with from 1-2 independently selected $R^b$.

In certain embodiments, $R^{23}$ is branched $C_4$-$C_8$ alkyl (e.g., tert-butyl), which is optionally substituted with from 1-2 independently selected $R^b$.

In some embodiments, $R^{23}$ is unsubstituted $C_1$-$C_8$ alkyl (e.g., unsubstituted $C_2$-$C_8$ alkyl, unsubstituted $C_3$-$C_8$ alkyl, unsubstituted branched $C_3$-$C_8$ alkyl, unsubstituted branched $C_4$-$C_8$ alkyl).

In certain embodiments, $R^{23}$ is $CH_3$.
In certain embodiments, $R^{23}$ is tert-butyl.

[O] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are hydroxyl, and the others are hydrogen;
and
$R^{23}$ is $C_1$-$C_8$ alkyl (e.g., $C_3$-$C_8$ alkyl, branched $C_3$-$C_8$ alkyl, e.g., tert-butyl; or $CH_3$), which is optionally substituted with from 1-2 independently selected $R^b$;
and
$R^{25}$ is hydrogen; $C_1$-$C_3$ alkyl (e.g., $CH_3$); or (—C(O)O ($C_1$-$C_6$ alkyl); (e.g., hydrogen; $C_1$-$C_3$ alkyl (e.g., $CH_3$));
and
$R^{26}$ and $R^{27}$ together are a bond (form a second or double bond between the carbon atoms to which each is attached);
and
$R^{24}$ is $C_3$-$C_{10}$ cycloalkyl, which is optionally substituted with from 1-4 independently selected $R^d$.

In some embodiments, $R^{25}$ is hydrogen.

In certain embodiments, $R^{25}$ is unsubstituted $C_1$-$C_3$ alkyl, e.g., $CH_3$.

In some embodiments, $R^{24}$ is cyclohexyl, which is optionally substituted with from 1-4 independently selected $R^d$ (as defined above or anywhere herein).

In some embodiments, $R^{23}$ is $C_1$-$C_3$ (e.g., $C_1$-$C_2$) alkyl, which is optionally substituted with from 1-2 independently selected $R^b$.

In some embodiments, $R^{23}$ is $C_2$-$C_8$ alkyl (e.g., tert-butyl), which is optionally substituted with from 1-2 independently selected $R^b$.

In some embodiments, $R^{23}$ is $C_3$-$C_8$ alkyl (e.g., tert-butyl), which is optionally substituted with from 1-2 independently selected $R^b$.

In certain embodiments, $R^{23}$ is straight chain $C_3$-$C_8$ alkyl, which is optionally substituted with from 1-2 independently selected $R^b$.

In certain embodiments, $R^{23}$ is branched $C_3$-$C_8$ alkyl (e.g., tert-butyl), which is optionally substituted with from 1-2 independently selected $R^b$.

In some embodiments, $R^{23}$ is $C_4$-$C_8$ alkyl, which is optionally substituted with from 1-2 independently selected $R^b$.

In certain embodiments, $R^{23}$ is straight chain $C_4$-$C_8$ alkyl, which is optionally substituted with from 1-2 independently selected $R^b$.

In certain embodiments, $R^{23}$ is branched $C_4$-$C_8$ alkyl (e.g., tert-butyl), which is optionally substituted with from 1-2 independently selected $R^b$.

In some embodiments, $R^{23}$ is unsubstituted $C_1$-$C_8$ alkyl (e.g., unsubstituted $C_2$-$C_8$ alkyl, unsubstituted $C_3$-$C_8$ alkyl, unsubstituted branched $C_3$-$C_8$ alkyl, unsubstituted branched $C_4$-$C_8$ alkyl).

In certain embodiments, $R^{23}$ is $CH_3$.

In certain embodiments, $R^{23}$ is tert-butyl.

[P] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are hydroxyl, and the others are hydrogen;
and
$R^{23}$ is:
(i) $C_3$-$C_6$ cycloalkyl, which is optionally substituted with from 1-4 independently selected $R^d$; or
(ii) $C_1$-$C_8$ alkyl (e.g., $C_3$-$C_8$ alkyl, branched $C_3$-$C_8$ alkyl, e.g., tert-butyl; or $CH_3$), which is optionally substituted with from 1-2 independently selected $R^b$;
and
$R^{25}$ is hydrogen; or $C_1$-$C_3$ alkyl (e.g., $CH_3$);
and
$R^{26}$ and $R^{27}$ together are a bond (form a second or double bond between the carbon atoms to which each is attached);
and
$R^{24}$ is heterocyclyl containing from 3-6 ring atoms, wherein from 1-2 of the ring atoms is independently selected from N, NH, N($C_1$-$C_3$ alkyl), NC(O)($C_1$-$C_6$ alkyl), O, and S; and wherein said heterocyclyl is optionally substituted with from 1-3 independently selected $R^d$ (e.g., piperidinyl).

In some embodiments, $R^{25}$ is hydrogen.

In certain embodiments, $R^{25}$ is unsubstituted $C_1$-$C_3$ alkyl, e.g., $CH_3$.

In some embodiments, $R^{23}$ is cyclopropyl, which is optionally substituted with from 1-4 independently selected $R^d$ (e.g., $C_1$-$C_6$ alkyl, $C_1$-$C_3$ alkyl).

[Q] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are hydroxyl, and the others are hydrogen;
and
$R^{23}$ is:
(i) $C_3$-$C_6$ cycloalkyl, which is optionally substituted with from 1-4 independently selected $R^d$; or
(ii) $C_1$-$C_8$ alkyl (e.g., $C_3$-$C_8$ alkyl, branched $C_3$-$C_8$ alkyl, e.g., tert-butyl; or $CH_3$), which is optionally substituted with from 1-2 independently selected $R^b$;
and
$R^{25}$ is hydrogen; or $C_1$-$C_3$ alkyl (e.g., $CH_3$);
and
$R^{26}$ and $R^{27}$ together are a bond (form a second or double bond between the carbon atoms to which each is attached);
and
$R^{24}$ is $C_6$-$C_{10}$ aryl, which is optionally substituted with from 1-5 independently selected R; (e.g., phenyl).

In some embodiments, $R^{25}$ is hydrogen.

In certain embodiments, $R^{25}$ is unsubstituted $C_1$-$C_3$ alkyl, e.g., $CH_3$.

In some embodiments, $R^{23}$ is cyclopropyl, which is optionally substituted with from 1-4 independently selected $R^d$ (e.g., $C_1$-$C_6$ alkyl, $C_1$-$C_3$ alkyl).

[R] In some embodiments:
$R^{22}$ has formula (A) as defined herein, in which three of $R^{221}$, $R^{222}$, $R^{223}$, $R^{224}$, and $R^{225}$ (e.g., $R^{221}$, $R^{223}$, and $R^{224}$; or $R^{221}$, $R^{222}$, and $R^{223}$) are hydroxyl, and the others are hydrogen;
and
$R^{23}$ is heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 independently selected $R^c$ (e.g., thienyl).
and
$R^{25}$ is hydrogen; or $C_1$-$C_3$ alkyl (e.g., $CH_3$);
and
$R^{26}$ and $R^{27}$ together are a bond (form a second or double bond between the carbon atoms to which each is attached);
and
$R^{24}$ is $C_3$-$C_{10}$ cycloalkyl, which is optionally substituted with from 1-4 independently selected $R^d$.

In some embodiments, $R^{25}$ is hydrogen.

In certain embodiments, $R^{25}$ is unsubstituted $C_1$-$C_3$ alkyl, e.g., $CH_3$.

In some embodiments, $R^{23}$ is cyclopropyl, which is optionally substituted with from 1-4 independently selected $R^d$ (e.g., $C_1$-$C_6$ alkyl, $C_1$-$C_3$ alkyl).

In some embodiments, $R^{24}$ is cyclohexyl, which is optionally substituted with from 1-4 independently selected $R^d$ (as defined above or anywhere herein).

Exemplary compounds include those in Table A below; see also the compounds delineated in FIGS. 20A and 20B. In certain embodiments, the compound is 187-7.

TABLE A

| ID | Structure | MCL-1 (IC$_{50}$) | BFL-1/A1 (IC$_{50}$) |
|---|---|---|---|
| 187-7 | 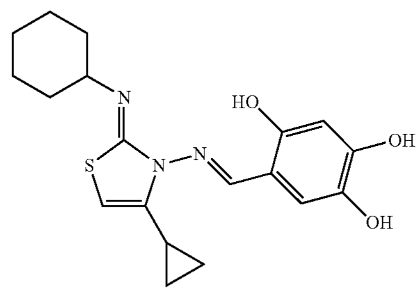 [SMILES: Oc1cc(O)c(/C=N/n2c(C3CC3)cs/c2=N\C2CCCCC2)cc1O] | 123 nM | 26 nM |
| 183-87 | 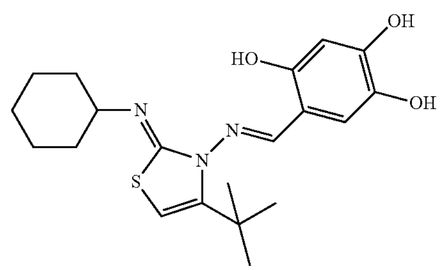 [SMILES: CC(C)(C)c1cs/c(=N\C2CCCCC2)n1/N=C/c1cc(O)c(O)cc1O] | 151 nM | 42 nM |
| 183-44 | 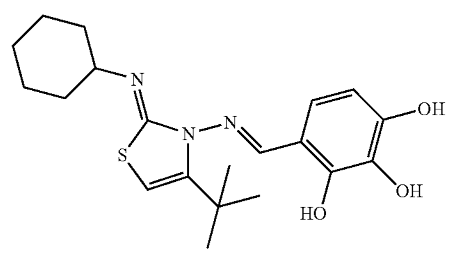 [SMILES: CC(C)(C)c1cs/c(=N\C2CCCCC2)n1/N=C/c1ccc(O)c(O)c1O] | 540 nM | 914 nM |
| 187-44 | 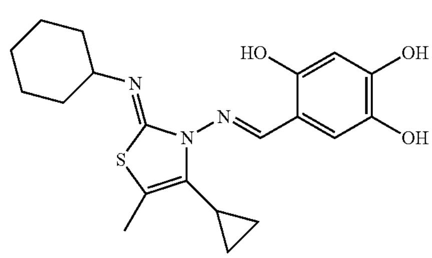 [SMILES: Cc1s/c(=N\C2CCCCC2)n(/N=C/c2cc(O)c(O)cc2O)c1C1CC1] | 587 nM | 117 nM |
| 183-89 | 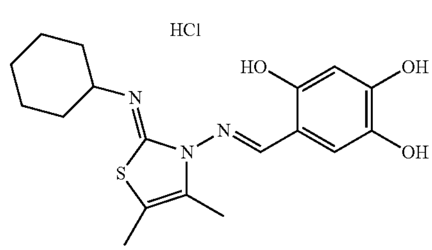 [SMILES: Cl ; Cc1s/c(=N\C2CCCCC2)n(/N=C/c2cc(O)c(O)cc2O)c1C] | 780 nM | 581 nM |

TABLE A-continued

| ID | Structure | MCL-1 (IC$_{50}$) | BFL-1/A1 (IC$_{50}$) |
| --- | --- | --- | --- |
| 187-19 | 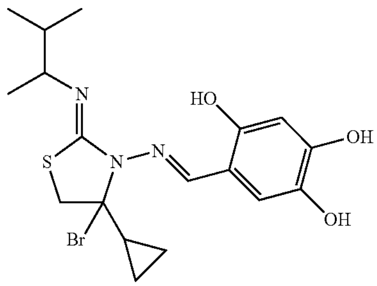 [SMILES: CC(C)C(C)/N=C1\SCC(Br)(C2CC2)N1/N=C/c1cc(O)c(O)cc1O] | 891 nM | 124 nM |
| 178-83 | 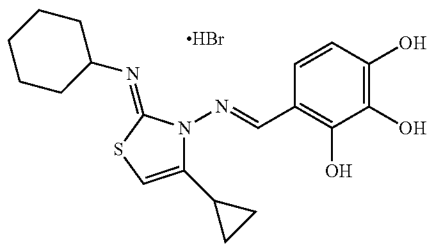 [SMILES: Oc1ccc(/C=N/n2c(C3CC3)cs/c2=N\C2CCCCC2)c(O)c1O ; Br] | 910 nM | 785 nM |
| 187-79 | 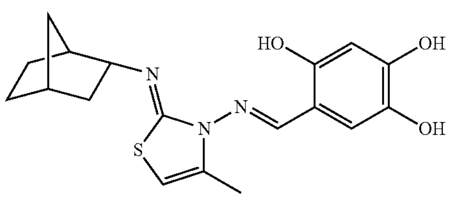 [SMILES: Cc1cs/c(=N\C2CC3CCC2C3)n1/N=C/c1cc(O)c(O)cc1O] | 937 nM | 272 nM |
| 183-82 | 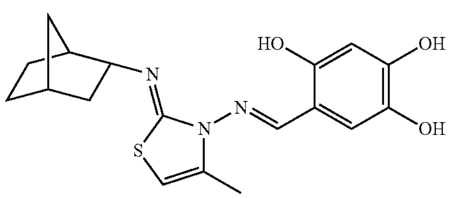 [SMILES: Cc1cs/c(=N\C2CC3CCC2C3)n1/N=C/c1cc(O)c(O)cc1O] | 1.0 uM | 169 nM |
| 183-88 | 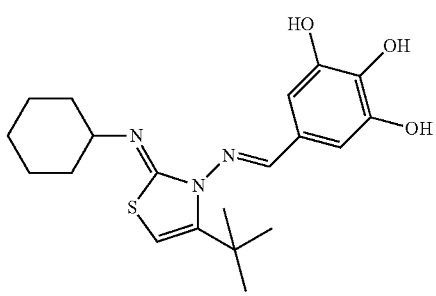 [SMILES: CC(C)(C)c1cs/c(=N\C2CCCCC2)n1/N=C/c1cc(O)c(O)c(O)c1] | 1.16 uM | 759 nM |
| 187-22 | 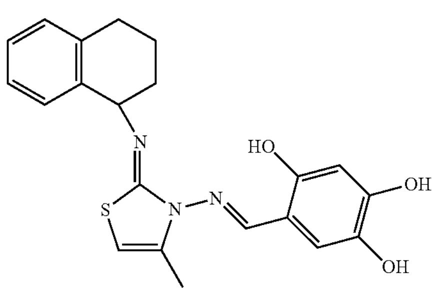 [SMILES: Cc1cs/c(=N\C2CCCc3ccccc32)n1/N=C/c1cc(O)c(O)cc1O] | 1.41 uM | 144 nM |

TABLE A-continued

| ID | Structure | MCL-1 (IC$_{50}$) | BFL-1/A1 (IC$_{50}$) |
| --- | --- | --- | --- |
| 183-8 | (cyclohexyl-N=thiazole(4,5-dimethyl)-N-N=CH-phenyl(2,3,4-triOH)) ·HCl | 1.5 uM | 712 nM |
| 187-20 | (sec-butyl-NH-thiazole(4-methyl)-N-N=CH-phenyl(2,3,4-triOH)) | 1.78 uM | 2.1 uM |
| 183-70 | (cyclohexyl-N=thiazole(4-neopentyl)-N-N=CH-phenyl(2,3,4-triOH)) HCl | 1.97 uM | 1.5 uM |
| 178-82 | (cyclohexyl-N=thiazole(4-ethyl)-N-N=CH-phenyl(2,3,4-triOH)) ·HBr | 2.1 uM | 1.2 uM |
| 183-22 | (cyclopentyl-N=thiazole(4-cyclopropyl)-N-N=CH-phenyl(2,3,4-triOH)) ·HBr | 2.4 uM | 601 nM |
| 187-5 | (cyclohexylmethyl-N=thiazole(4-methyl)-N-N=CH-phenyl(2,3,4-triOH)) | 2.7 uM | 1.1 uM |

TABLE A-continued
| ID | Structure | MCL-1 (IC$_{50}$) | BFL-1/A1 (IC$_{50}$) |
|---|---|---|---|
| 183-51 | 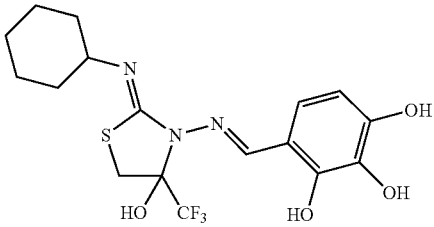 [SMILES: Oc1ccc(/C=N/N2/C(=N/C3CCCCC3)SCC2(O)C(F)(F)F)c(O)c1O] | 2.9 uM | 1.2 uM |
| 183-19 | 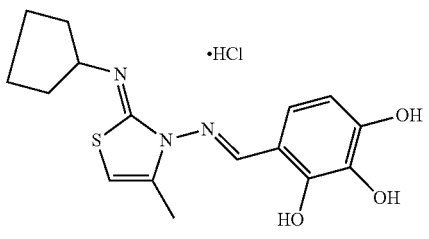 [SMILES: Cc1cs/c(=N\C2CCCC2)n1/N=C/c1ccc(O)c(O)c1O ; Cl] | 3.1 uM | 631 nM |
| 183-21 | 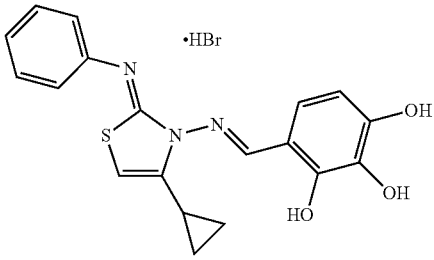 [SMILES: Oc1ccc(/C=N/n2c(C3CC3)cs/c2=N\c2ccccc2)c(O)c1O ; Br] | 4.3 uM | 719 nM |
| 187-27 | 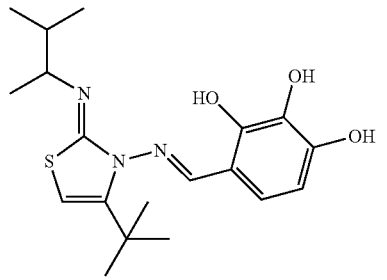 [SMILES: CC(C)C(C)/N=c1\scc(C(C)(C)C)n1/N=C/c1ccc(O)c(O)c1O] | 4.3 uM | 1.5 uM |
| 187-23 | 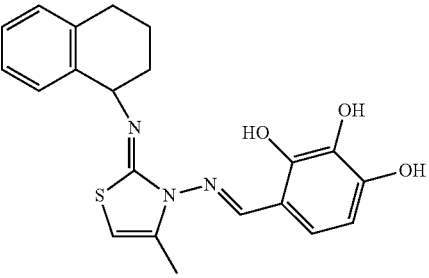 [SMILES: Cc1cs/c(=N\C2CCCc3ccccc32)n1/N=C/c1ccc(O)c(O)c1O] | 4.36 uM | 1.1 uM |

TABLE A-continued

| ID | Structure | MCL-1 (IC$_{50}$) | BFL-1/A1 (IC$_{50}$) |
| --- | --- | --- | --- |
| 183-81 | 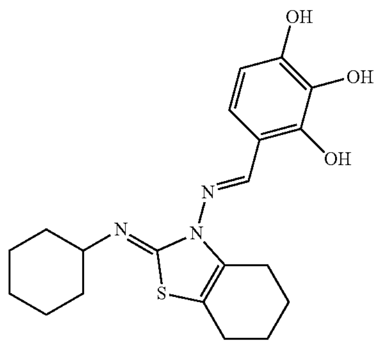 [SMILES: Oc1ccc(/C=N/n2c3c(s/c2=N\C2CCCCC2)CCCC3)c(O)c1O] | 4.5 uM | 1.3 uM |
| 187-39 | 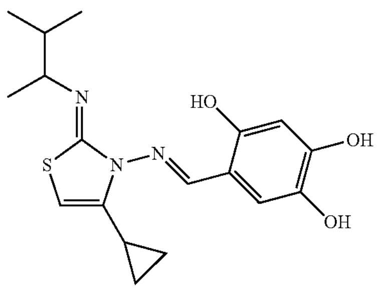 [SMILES: CC(C)C(C)/N=c1\scc(C2CC2)n1/N=C/c1cc(O)c(O)cc1O] | 7.3 uM | 1.1 uM |
| 183-85 | 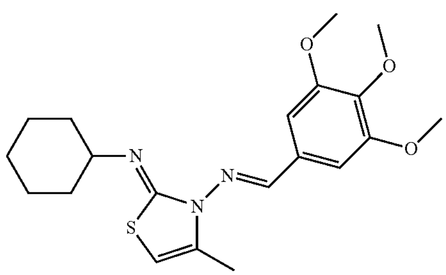 [SMILES: COc1cc(/C=N/n2c(C)cs/c2=N\C2CCCCC2)cc(OC)c1OC] | 7.6 uM | — |
| 178-97 | 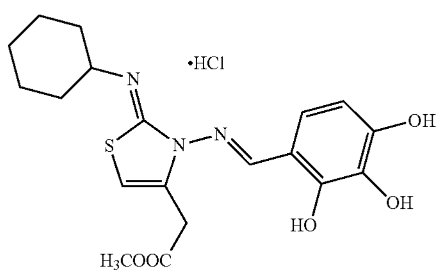 | 9.5 uM | 1.0 uM |
| 183-76 | 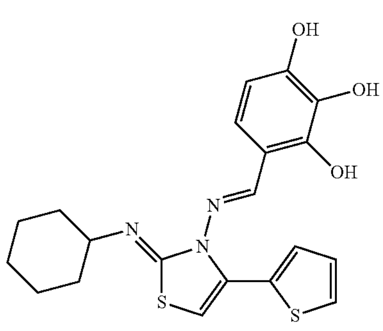 [SMILES: Oc1ccc(/C=N/n2c(-c3cccs3)cs/c2=N\C2CCCCC2)c(O)c1O] | 11 uM | 388 nM |

TABLE A-continued

| ID | Structure | MCL-1 (IC$_{50}$) | BFL-1/A1 (IC$_{50}$) |
| --- | --- | --- | --- |
| 183-91 | 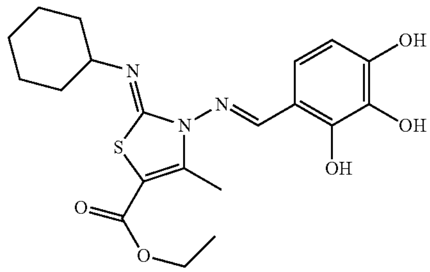 [SMILES: CCOC(=O)c1s/c(=N\C2CCCCC2)n(/N=C/c2ccc(O)c(O)c2O)c1C] | 11.8 uM | 381 nM |
| 183-38 | 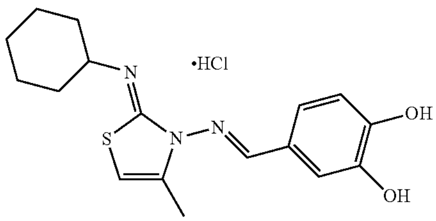 [SMILES: Cc1cs/c(=N\C2CCCCC2)n1/N=C/c1ccc(O)c(O)c1 ; Cl] | 12 uM | 282 nM |
| 183-84 | 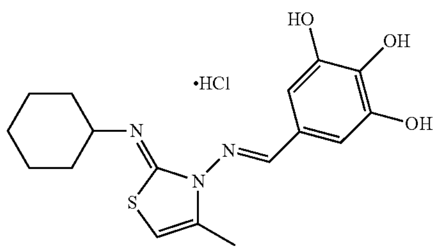 [SMILES: Cc1cs/c(=N\C2CCCCC2)n1/N=C/c1cc(O)c(O)c(O)c1 ; Cl] | 13 uM | 316 nM |
| 187-82 | 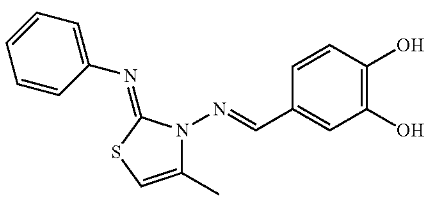 [SMILES: Cc1cs/c(=N\c2ccccc2)n1/N=C/c1ccc(O)c(O)c1] | 13.3 uM | 8.1 uM |
| 183-63 | 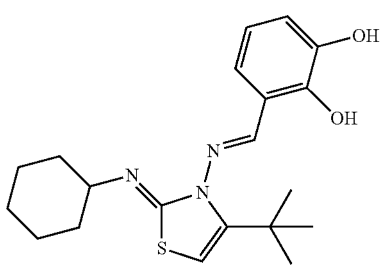 [SMILES: CC(C)(C)c1cs/c(=N\C2CCCCC2)n1/N=C/c1cccc(O)c1O] | — | — |
| 178-32 | 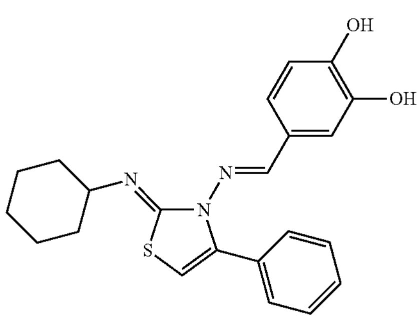 [SMILES: Oc1ccc(/C=N/n2c(-c3ccccc3)cs/c2=N\C2CCCCC2)cc1O] | — | — |

TABLE A-continued

| ID | Structure | MCL-1 (IC$_{50}$) | BFL-1/A1 (IC$_{50}$) |
|---|---|---|---|
| 178-21 | 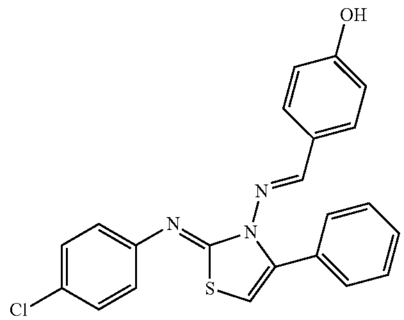 [SMILES: Oc1ccc(/C=N/n2c(-c3ccccc3)cs/c2=N\c2ccc(Cl)cc2)cc1] | — | — |
| 178-23 | 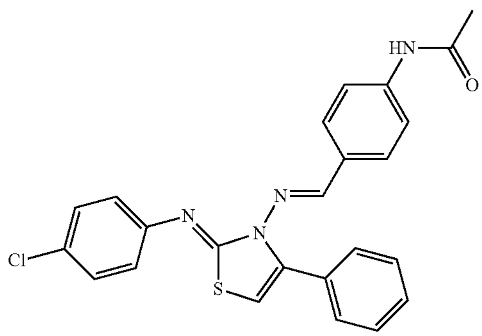 [SMILES: CC(=O)Nc1ccc(/C=N/n2c(-c3ccccc3)cs/c2=N\c2ccc(Cl)cc2)cc1] | — | — |
| 187-10 | 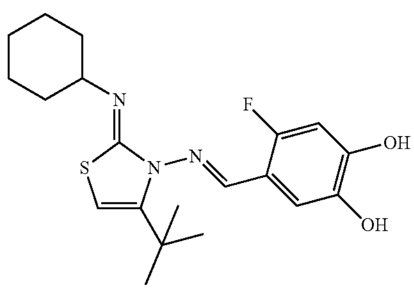 [SMILES: CC(C)(C)c1cs/c(=N\C2CCCCC2)n1/N=C/c1cc(O)c(O)cc1F] | — | 9.1 uM |
| 187-37 | 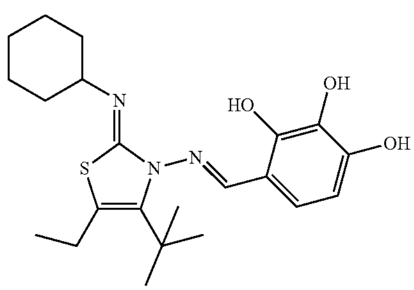 [SMILES: CCc1s/c(=N\C2CCCCC2)n(/N=C/c2ccc(O)c(O)c2O)c1C(C)(C)C] | — | 2.8 uM |
| 178-31 | 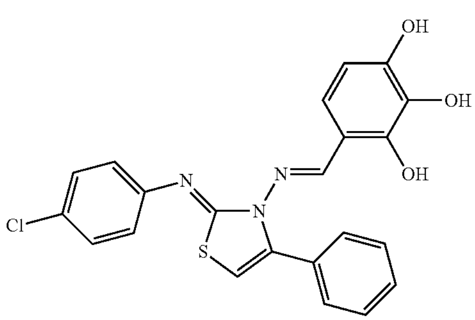 [SMILES: Oc1ccc(/C=N/n2c(-c3ccccc3)cs/c2=N\c2ccc(Cl)cc2)c(O)c1O] | — | — |

TABLE A-continued

| ID | Structure | MCL-1 (IC$_{50}$) | BFL-1/A1 (IC$_{50}$) |
|---|---|---|---|
| 187-50 | | — | 735 nM |
| 187-58 | | — | 689 nM |
| 187-60 | 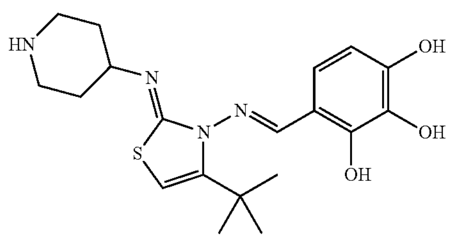 [SMILES: CC(C)(C)c1cs/c(=N\C2CCNCC2)n1/N=C/c1ccc(O)c(O)c1O] | — | 718 nM |
| 187-81 | 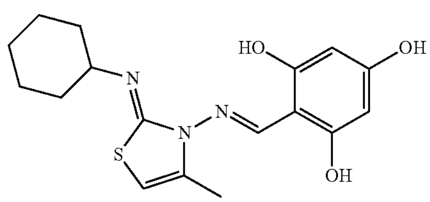 [SMILES: Cc1cs/c(=N\C2CCCCC2)n1/N=C/c1c(O)cc(O)cc1O] | — | 31 uM |
| 187-50 | | — | 735 nM |
| 187-58 | | — | 265 nM |

TABLE A-continued

| ID | Structure | MCL-1 (IC$_{50}$) | BFL-1/A1 (IC$_{50}$) |
| --- | --- | --- | --- |
| 187-60 | 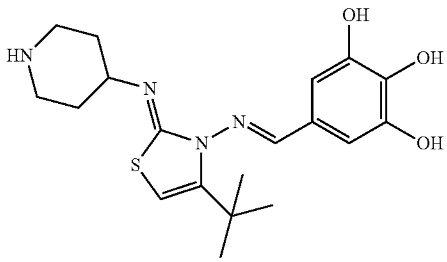 [SMILES: CC(C)(C)c1cs/c(=N\C2CCNCC2)n1/N=C/c1cc(O)c(O)c(O)c1] | — | 718 nM |
| 187-81 | 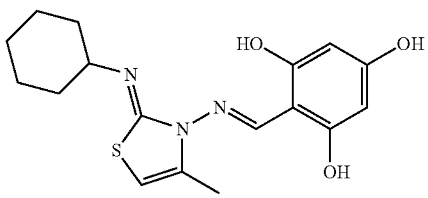 [SMILES: Cc1cs/c(=N\C2CCCCC2)n1/N=C/c1c(O)cc(O)cc1O] | — | 31 uM |
| 187-82 | 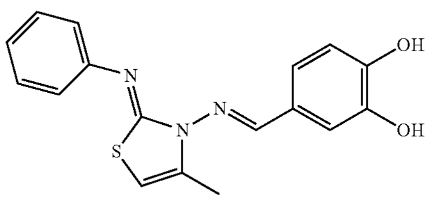 [SMILES: Cc1cs/c(=N\c2ccccc2)n1/N=C/c1ccc(O)c(O)c1] | — | 8.1 uM |
| 187-95 | 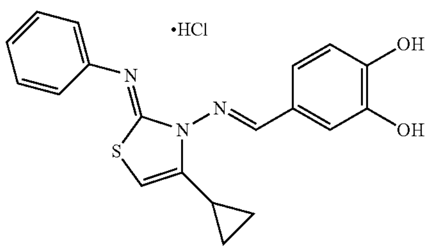 [SMILES: Oc1ccc(/C=N/n2c(C3CC3)cs/c2=N\c2ccccc2)cc1O ; Cl] | — | 3.0 uM |
| 187-112 | 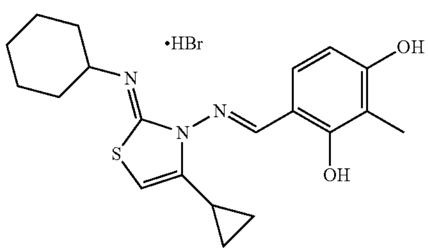 [SMILES: Cc1c(O)ccc(/C=N/n2c(C3CC3)cs/c2=N\C2CCCCC2)c1O ; Br] | — | — |
| 187-113 | 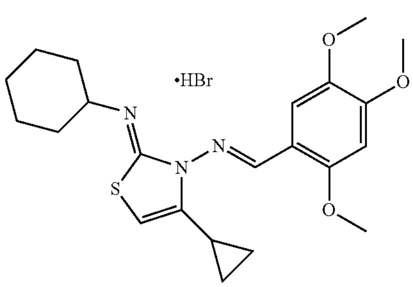 [SMILES: COc1cc(OC)c(OC)cc1/C=N/n1c(C2CC2)cs/c1=N\C1CCCCC1 ; Br] | — | — |

TABLE A-continued

| ID | Structure | MCL-1 (IC$_{50}$) | BFL-1/A1 (IC$_{50}$) |
|---|---|---|---|
| 187-114 | 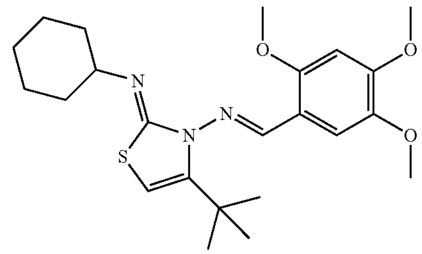 [SMILES: COc1cc(OC)c(OC)cc1/C=N/n1c(C(C)(C)C)cs/c1=N\C1CCCCC1] | — | — |
| 190-4 | 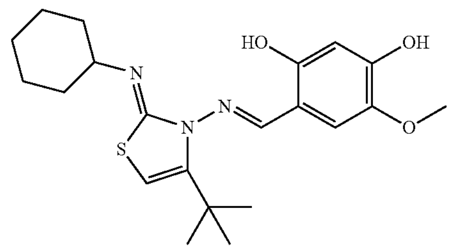 [SMILES: COc1cc(/C=N/n2c(C(C)(C)C)cs/c2=N\C2CCCCC2)c(O)cc1O] | — | 15 uM |
| 190-18 | ·HBr | | 1.7 uM |
| 190-20 | ·HBr | | 365 nM |
| 183-36 | ·HCl | — | — |
| 178-31 | 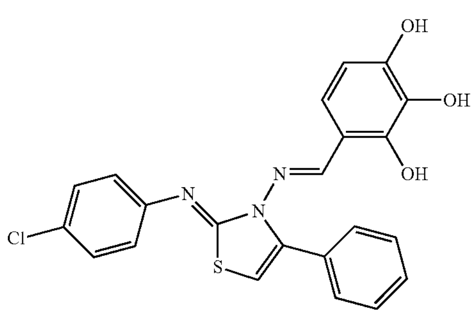 [SMILES: Oc1ccc(/C=N/n2c(-c3ccccc3)cs/c2=N\c2ccc(Cl)cc2)c(O)c1O] | — | — |

TABLE A-continued

| ID | Structure | MCL-1 (IC$_{50}$) | BFL-1/A1 (IC$_{50}$) |
|---|---|---|---|
| 183-20 | 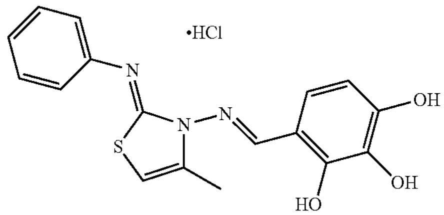 [SMILES: Cc1cs/c(=N\c2ccccc2)n1/N=C/c1ccc(O)c(O)c1O ; Cl] | — | 264 nM |
| 183-70 | 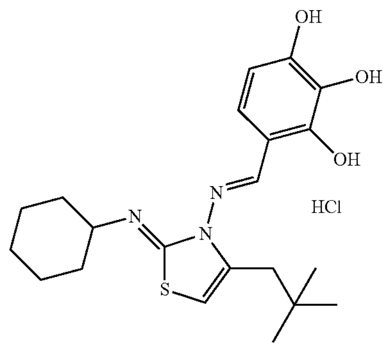 [SMILES: CC(C)(C)Cc1cs/c(=N\C2CCCCC2)n1/N=C/c1ccc(O)c(O)c1O ; Cl] | — | 1.5 uM |
| 183-75 | 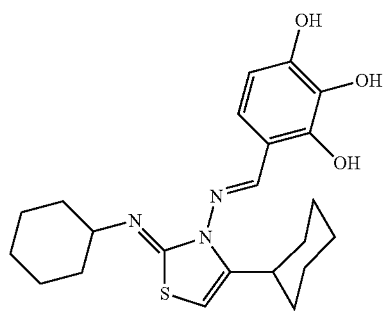 [SMILES: Oc1ccc(/C=N/n2c(C3CCCCC3)cs/c2=N\C2CCCCC2)c(O)c1O] | — | — |
| 183-83 | 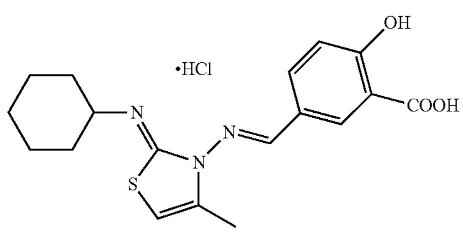 [SMILES: Cc1cs/c(=N\C2CCCCC2)n1/N=C/c1ccc(O)c(C(=O)O)c1 ; Cl] | — | — |
| 183-95 | 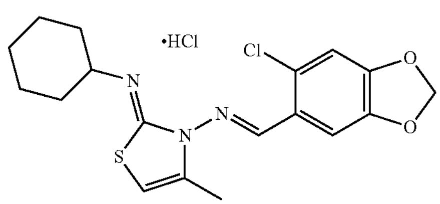 [SMILES: Cc1cs/c(=N\C2CCCCC2)n1/N=C/c1cc2c(cc1Cl)OCO2 ; Cl] | — | — |
| 187-8 | 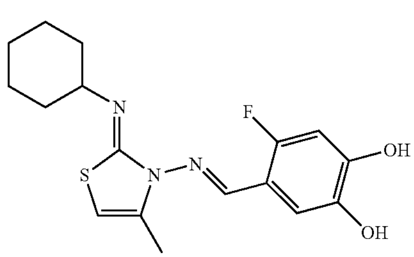 [SMILES: Cc1cs/c(=N\C2CCCCC2)n1/N=C/c1cc(O)c(O)cc1F] | — | 8.4 uM |

TABLE A-continued

| ID | Structure | MCL-1 (IC$_{50}$) | BFL-1/A1 (IC$_{50}$) |
|---|---|---|---|
| 178-72 | 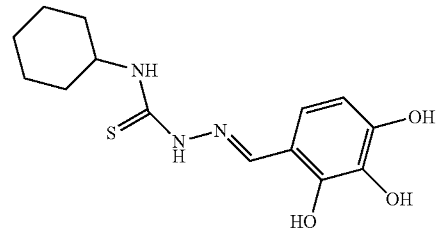 [SMILES: Oc1ccc(/C=N/NC(=S)NC2CCCCC2)c(O)c1O] | 16 uM | 5.1 uM |
| 183-24 | ·HCl | 16 uM | 2.5 uM |
| 183-65 | 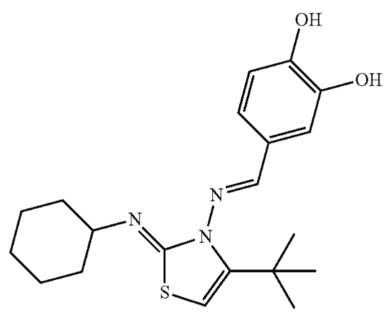 [SMILES: CC(C)(C)c1cs/c(=N\C2CCCCC2)n1/N=C/c1ccc(O)c(O)c1] | 17.7 uM | 2.1 uM |

Compound Forms and Salts

In some embodiments, the formula (I) and/or (II) compounds described herein may contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms may be present in a substituent, such as an alkyl group. All such isomeric forms, as well as mixtures thereof, of these compounds are expressly included in the present invention. The compounds described herein may also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present invention. The compounds of this invention may also be represented in multiple tautomeric forms; in such instances, the invention expressly includes all tautomeric forms of the compounds described herein, even though only a single tautomeric form may be represented. All such isomeric forms of such compounds are expressly included in the present invention. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The combinations described herein can include formula (I) and/or (II) compounds that are in the form of a salt. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

Pharmaceutically acceptable salts of the formula (I) and/or (II) compounds include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8]; and Berge et al. (1977) "Pharmaceutical Salts", J. Pharm. Sci. 66:1-19; each of which is incorporated herein by reference in its entirety.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention includes formula (I) and/or (II) compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug.

The invention also includes various hydrate and solvate forms of the formula (I) compounds (and salts thereof) described herein.

The formula (I) and/or (II) compounds may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

Synthesis of Compounds

Methods of obtaining a formula (I) and/or (II) compound or other therapeutic agents described herein include purchasing, synthesizing or otherwise acquiring the compound.

In some embodiments, the formula (I) and/or (II) compounds can be prepared using the methods outlined in the schemes below (see also the Examples section).

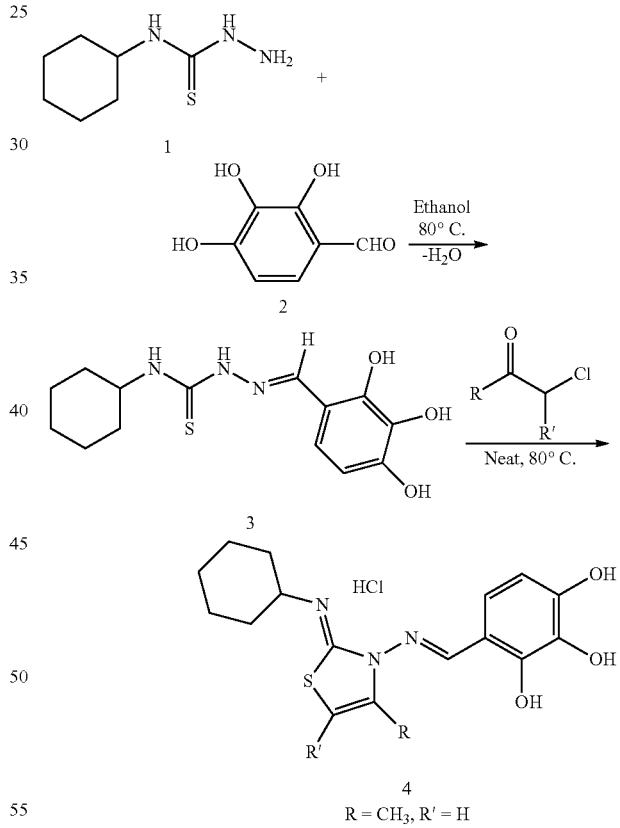

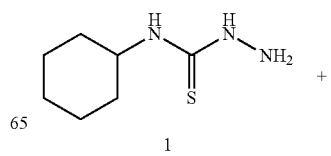

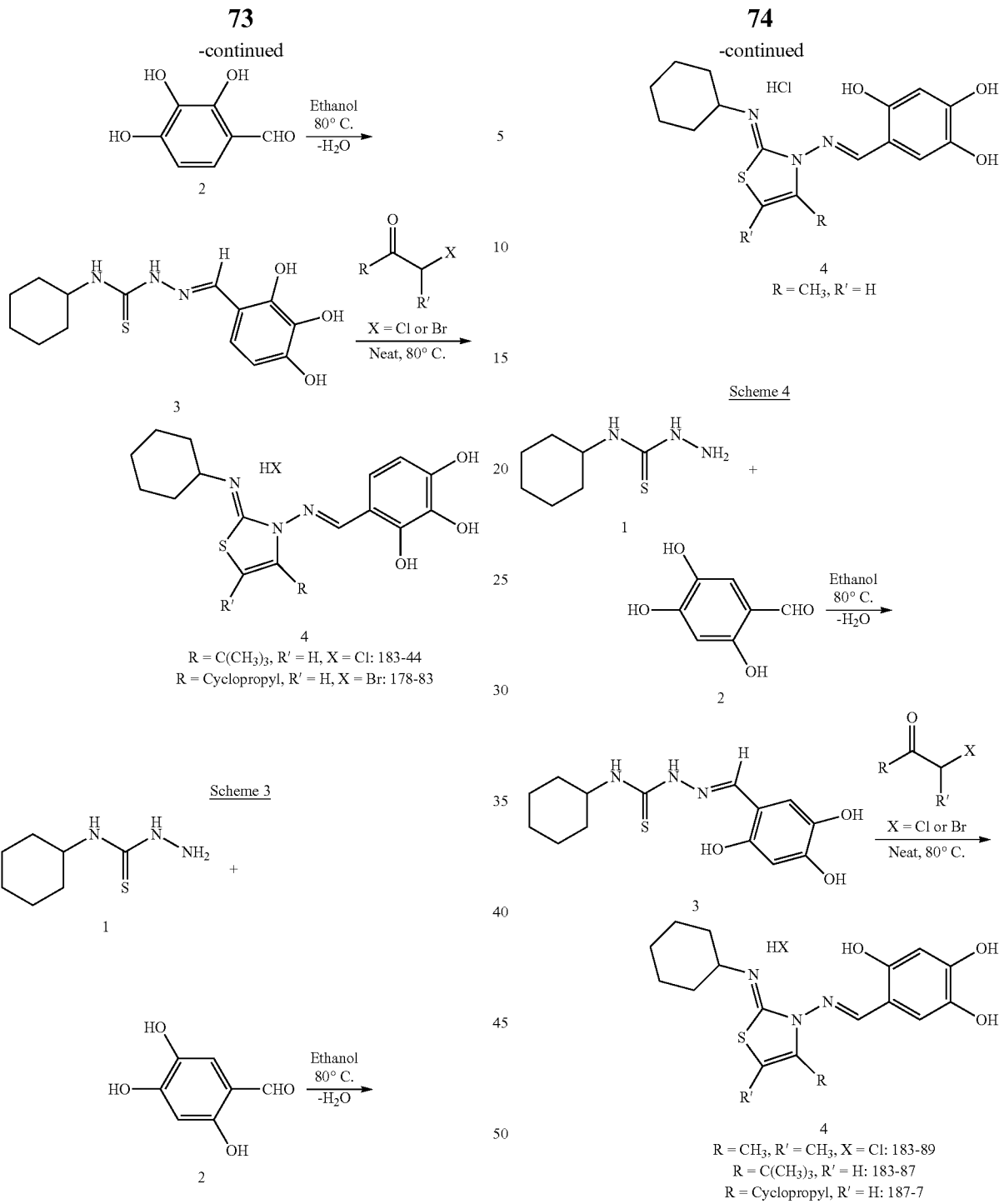

Synthesizing the compounds described herein is within the skill of the organic chemistry art. The compounds described herein can be conveniently prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations,* 2d.ed., Wiley-VCH Publishers (1999); P. G. M. Wuts and T. W. Greene, *Protective Groups in Organic Synthesis,* 4th Ed., John Wiley and Sons (2007); L. Fieser and M. Fieser, *Fieser and Fieser's Reagents for Organic Synthesis,* John Wiley and Sons (1994); and L. Paquette, ed., *Encyclopedia ofReagents for Organic Synthesis,* John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FT-IR), spectrophotometry (e.g., UV-visible), or mass spectrometry (MS), or by chromatography such as high performance liquid chromatograpy (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of solvents. Depending on the particular reaction step, suitable solvents for a particular reaction step can be selected.

Pharmaceutical Compositions

The term "pharmaceutically acceptable carrier" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the combinations described herein.

Pharmaceutically acceptable carriers, adjuvants and vehicles that may be used in the combinations of the invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of the formula (I) compounds and therapeutic agent(s) that are present in the combinations described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The amount administered depends on the formulation, route of administration, etc. and is generally empirically determined in routine trials, and variations will necessarily occur depending on the target, the host, and the route of administration, etc. Generally, the quantity of the formula (I) and/or (II) compounds and therapeutic agent(s) that are present in the combinations described herein may be varied or adjusted from about 1, 3, 10 or 30 to about 30, 100, 300 or 1000 mg per in a unit dose of preparation, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the formula (I) compounds and therapeutic agent(s) that are present in the combinations. Thereafter, the dosage is increased by small amounts until the optimum effect under the circumstances is reached. For convenience, the total daily dosage may be divided and administered in portions during the day if desired.

Use and Administration

The combinations described herein are therapeutically useful for treating (e.g., controlling, relieving, ameliorating, alleviating, or slowing the progression of) or preventing (e.g., delaying the onset of or reducing the risk of developing) diseases, disorders, and conditions associated with deregulated apoptosis of cells (e.g., diseased or damaged cells; e.g., insufficient apoptosis of diseased or damaged cells; or lack of apoptosis of diseased or damaged cells). Examples of such diseases, disorders, and conditions include (but are not limited to) those associated with blockade(s) of cell death pathways (e.g., over-expression of anti-apoptotic BCL-2 proteins; e.g., over-expression of anti-apoptotic BCL-2 proteins that fall outside of the inhibitory spectrum of a particular anti-apoptotic BCL-2 protein inhibitor, such as ABT-263 or ABT-737). Examples of such diseases, disorders, and conditions include hyperproliferative diseases, such as cancer.

As used herein the term "hyperproliferative disorder" refers to a disorder associated with an irregular or an abnormally high rate of cell division (which results in a rapid proliferation of the cells) or a blockade in the natural cell death pathway resulting in the accumulation of cells, or a combination thereof. Hyperproliferative disorders include but are not limited, e.g., solid and liquid tumors, such as cancers of the breast, respiratory tract, brain, reproductive organs, digestive tract, urinary tract, eye, liver, skin, head and neck, thyroid, parathyroid and their distant metastases, lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The one or more additional therapeutic agents that bind to and inhibit anti-apoptotic proteins and any additional therapeutic agents may be administered separately, as part of a multiple dose regimen, from the compound of formula (I) (e.g., sequentially, e.g., on different overlapping schedules with the administration of one or more compounds of formula (I) (including any subgenera or specific compounds thereof)). In other embodiments, the one or more additional therapeutic agents that bind to and inhibit anti-apoptotic proteins and any additional therapeutic agents may be part of a single dosage form, mixed together with the compound of formula (I) in a single composition. In still another embodiment, the one or more additional therapeutic agents that bind to and inhibit anti-apoptotic proteins and any additional therapeutic agents can be given as a separate dose that is administered at about the same time that one or more compounds of formula (I) are administered (e.g., simultaneously with the administration of one or more compounds of formula (I) (including any subgenera or specific compounds thereof)). Both the compound of formula (I) and the one or more additional therapeutic agents that bind to and inhibit anti-apoptotic proteins and any additional therapeutic agents can be present at dosage levels of between about 1 to 100%, and more preferably between about 5 to 95% of the dosage normally administered in a monotherapy regimen.

The combinations described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation (or any combination thereof if, for example, the one or more additional therapeutic agents that bind to and inhibit anti-apoptotic proteins and any additional therapeutic agents may be administered separately, as part of a multiple dose regimen, from the compound of formula (I)), with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the combinations are administered by oral administration or administration by injection. The methods herein contemplate administration of an effective amount of the compound of formula (I) and the one or more additional therapeutic agents that bind to and inhibit anti-apoptotic proteins and any additional therapeutic agents to achieve the desired or stated effect. In certain embodiments, the combinations of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The combinations of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The combinations may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The combinations of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The combinations of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the combinations of this invention is useful when the desired treatment involves areas or organs readily accessible by topical application. For application topically to the skin, the composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation.

In some embodiments, topical administration of the combinations described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in this invention. Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The combinations of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A combination can be administered using any of the routes of administration described herein. In some embodiments, a combination can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6): 563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

EXAMPLES

The invention will be further described in the following examples. It should be understood that these examples are for illustrative purposes only and are not to be construed as limiting this invention in any manner.

Example 1

From Selective Stapled Peptide to Selective Small Molecule

MCL-1 SAHBs are hydrocarbon-stapled MCL-1 BH3 helices that were previously shown using chemical, structural, and biological methods to selectively target MCL-1 and sensitize cancer cells to caspase-dependent apoptosis[34]. Here, we deployed MCL-1 SAHB$_A$ as a high fidelity screening tool to determine if its potency and specificity-of-action could be harnessed for small molecule discovery. A high-throughput competitive fluorescence polarization (FP) screening assay (Z-factor, 0.62) was developed based on the direct binding interaction between FITC-MCL-1 SAHB$_A$ and MCL-1ΔNΔC (EC$_{50}$, 14 nM) (FIGS. 1A, 2A, and 3A). A compilation of 71,296 small molecules was screened for the capacity to displace FITC-MCL-1 SAHB$_A$ from recombinant MCL-1ΔNΔC (aa 172-327) (FIG. 4). To enrich for MCL-1-selective molecules by detecting binding activity for the BCL-X$_L$ subclass of anti-apoptotic proteins, the library was also counterscreened using a competitive FP assay (Z-factor, 0.71) developed based on the direct and selective interaction between FITC-BAD BH3 and BCL-X$_L$ΔC (EC$_{50}$, 26 nM) (FIGS. 1B, 2B, and 3B). Small molecules with an apparent preference for MCL-1ΔNΔC (208 compounds, 0.3% hit rate), as defined both by >50% displacement of the FITC-MCL-1 SAHB$_A$/MCL-1ΔNΔC interaction and a >45% difference in peptide displacement from MCL-1ΔNΔC vs. BCL-X$_L$ΔC, were advanced to increasingly stringent confirmatory in vitro binding assays including: (1) repeat single-dose testing of 208 molecules in the differential competitive FP screen; (2) alternative single-dose selectivity screen for 130 confirmed MCL-1-directed antagonists comparing relative displacement of FITC-BID BH3, a dual binder,[35] from MCL-1 ΔNΔC vs. BCL-X$_L$ΔC; and then (3) dose-responsive competitive binding of the 64 most selective molecules against the FITC-MCL-1 SAHB$_A$/MCL-1ΔNΔC complex (FIG. 4). Of the 64 compounds that competed with FITC-MCL-1 SAHB$_A$ for MCL-1ΔNΔC binding at IC$_{50}$ potencies of <30 μM, we subjected 28 small molecules to dose-responsive target selectivity analysis in the comparative FITC-BID BH3/MCL-1ΔNΔC vs. FITC-BID BH3/BCL-X$_L$ΔC competition FP assay, and then to screening liposomal release and Bax$^{-/-}$Bak$^{-/-}$ mouse embryonic fibroblasts (MEFs) cytotoxicity assays. Ultimately, we selected 4-((E)-(((Z)-2-(cyclohexylimino)-4-methylthiazol-3(2H)-yl)imino)methyl)benzene-1,2,3-triol, termed MCL-1 Inhibitor Molecule 1 (MIM1, FIG. 4), as our prototype compound due to a combination of favorable biophysical and biological properties that included MW>200, solubility, MCL-1 binding potency and selectivity, compatibility with and activity in a BAX-mediated liposomal release assay, and relatively little to no toxicity in Bax$^{-/-}$Bak$^{-/-}$ MEFs.

The molecular structure of MIM1 (MW 347) is characterized by a thiazolyl core substituted with methyl, cyclohexylimino, and benzenetriol R groups (FIGS. 4 and 5). We chose to vet the anti-apoptotic binding selectivity of MIM1 in competitive FP assays by comparison with ABT-737, a selective BCL-2/BCL-X$_L$ inhibitor molecule[16]. Whereas MIM1 effectively competed with FITC-MCL-1 SAHB$_A$ and FITC-BID BH3 for MCL-1ΔNΔC binding with respective IC$_{50}$s of 4.7 and 4.8 μM, the compound showed no capacity to displace FITC-BID BH3 from BCL-X$_L$ΔC (IC$_{50}$>50 μM), mirroring the selectivity of Ac-MCL-1 SAHB$_D$ (FIGS. 6A, 6B, and 6C). In striking contrast, ABT-737 competed with FITC-BID BH3 for BCL-X$_L$ΔC binding, but showed no activity toward MCL-1ΔNΔC. Although Ac-MCL-1 SAHB$_D$ was a 30 to 60-fold more potent competitor for MCL-1 ΔNΔC binding than MIM1, the MCL-1-selective small molecule is one-seventh the size of the stapled peptide and exhibits an IC$_{50}$ for its target (4.8 μM) in the same range as that of ABT-737 for BCL-X$_L$ΔC (2.3 μM) upon competition with FITC-BID BH3. Thus, MIM1 emerged from the competitive screen with a marked MCL-1 ΔNΔC preference that reflects the binding specificity of the stapled peptide ligand and the opposite interaction profile of ABT-737.

Example 2

Structural Analysis of the MIM1/MCL-1ΔNΔC Interaction

To localize the protein interaction site that accounts for competitive small molecule binding activity, we performed NMR analysis of $^{15}$N-MCL-1ΔNΔC upon MIM1 titration. The addition of MIM1 up to a 2:1 molecule:protein ratio induced significant backbone amide chemical shift changes in those MCL-1 ΔNΔC residues concentrated in a subregion of the canonical BH3-binding pocket, which is comprised of residues from α2 (BH3) and portions of α3, α4, α5 (BH1) and α8 (BH2) (FIG. 7). These data are consistent with a direct interaction between MIM1 and MCL-1ΔNΔC at the very surface employed by BH3 helices to engage MCL-1.

We next performed molecular docking analysis to examine the predicted interactions between MIM1 and MCL-1 ΔNΔC at the BH3-binding pocket. Interestingly, MIM1 is predicted to occupy that portion of the BH3-binding site engaged by residues 211-216 ETLRRV (aa 211-216) of MCL-1 SAHB$_D$ (FIG. 8, PDB 3MK8[34]). Whereas the cyclohexyl group makes complementary hydrophobic contacts with the region of the protein interface flanked by MCL-1 SAHB$_D$ residues L213 and V216, the thiazolyl core and its methyl substituent points directly into a deep crevice occupied in the MCL-1 SAHB$_D$/MCL-1ΔNΔC complex by the highly conserved leucine (MCL-1 SAHB$_D$ L213) of BH3 domains. Interestingly, the benzene-1,2,3-triol (or pyrogallol) moiety engages in hydrophilic contacts with D256 and R263, two charged MCL-1 residues implicated in complementary electrostatic interactions with a variety of BH3 domain R/D pairs (e.g. aa R214, D218 of MCL-1

SAHB$_D$). Thus, MIM1 appears to simulate the key molecular features of approximately 1.5 turns of the MCL-1 BH3 helix at a potential selectivity hotspot on the MCL-1 binding surface.

Example 3

MIM1 Blocks MCL-1-mediated Suppression of Pro-Apoptotic BAX

We next examined whether MIM1 could selectively block MCL-1ΔNΔC -based suppression of BAX activation, as monitored by a BAX-mediated liposomal release assay tailored to distinguish between pharmacologic regulation by MCL-1 ΔNΔC vs. BCL-X$_L$ΔC. Whereas the BH3-only protein tBID directly triggers the transformation of monomeric BAX to a membrane-embedded oligomer that porates liposomal vesicles and releases encapsulated fluorophore, the addition of anti-apoptotic proteins, such as MCL-1ΔNΔC or BCL-X$_L$ΔC, blocks tBID-induced BAX activation and liposomal release (FIG. 9A). Whereas the BAX-suppressive effects of MCL-1 ΔNΔC are completely eliminated by pre-incubation with MCL-1 SAHB$_D$, BCL-X$_L$ΔC-based inhibition of BAX activation is unimpeded by the MCL-1 selective stapled peptide (FIG. 9B). Conversely, ABT-737, which selectively blocks BCL-X$_L$ΔC, negates BCL-X$_L$ΔC-mediated suppression of BAX activation but has no effect on MCL-1ΔNΔC activity (FIG. 9C). Having documented the high fidelity of this tailored liposomal assay for distinguishing between anti-apoptotic selectivities, we next evaluated the functional activity of MIM1. Indeed, we find that MIM1 simulates the pharmacologic activity of MCL-1 SAHB$_D$, preventing BAX suppression by MCL-1ΔNΔC but not by BCL-X$_L$ΔC (FIG. 9D). Consistent with the reduced molecular weight and competitive binding activity of MIM1 compared to MCL-1 SAHB$_D$, the kinetics of MIM1 inhibition of MCL-1 ΔNΔC-mediated BAX suppression are correspondingly slower (FIG. 6A, FIG. 6B, FIG. 9B, FIG. 9D). Thus, these data explicitly link the selective MCL-1 ΔNΔC binding activity of MIM1 with functional blockade of MCL-1 ΔNΔC-mediated inhibition of BAX activation.

Example 4

Selective Activation of MCL-1-dependent Leukemia Cell Death by MIM1

A challenges in developing and applying molecular antagonists for BCL-2 family anti-apoptotic proteins is the variable expression of multiple homologues. That is, a cancer cell will only be susceptible to a selective anti-apoptotic inhibitor if the cell is especially dependent on that particular survival protein. Thus, the mere expression of MCL-1 does not necessarily predict cancer cell sensitivity to an MCL-1 selective inhibitor, as other anti-apoptotics lying outside its binding spectrum may continue to effectively suppress BAX/BAK. To test MIM1's activity and specificity in cancer cells, we employed murine p185$^+$Arf$^{-/-}$Mcl-1$^{-/-}$ chronic myelogenous leukemia (CML) cells that are unable to survive unless reconstituted with MCL-1, reflecting a stringent system for assessing MCL-1 dependence. To validate the cellular assay, we first compared the effect of ABT-737 on p185$^+$Arf$^{-/-}$Mcl-1$^{-/-}$ cells rescued by overexpression of MCL-1 or BCL-X$_L$, and observed dose-responsive impairment of cancer cell viability (IC$_{50}$, 1.6 μM) that coincided with dose-responsive caspase 3/7 activation in the BCL-X$_L$-dependent cells, but no effect on the MCL-1-dependent cells (see FIGS. 11-12). Strikingly, MIM1 had the exact opposite effect, negatively impacting the viability of the MCL-1-dependent cells (IC$_{50}$, 4.2 μM), including dose-dependent induction of caspase 3/7 activity, but having little to no effect on the BCL-X$_L$-dependent cells (FIG. 4A-B). Importantly, ABT-737 and MIM1 had no significant effect on the viability of wild-type or Bax$^{-/-}$Bak$^{-/-}$ MEFs over the same dose range, with no observed caspase 3/7 activation (FIGS. 15A-15D).

We next examined the functional impact of combining ABT-737 and MIM1 in isogenic p185$^+$Arf$^{-/-}$ cells differing only in their expression of MCL-1 and BCL-X$_L$ (FIG. 10). In parental p185$^+$Arf$^{-/-}$ cells that express both MCL-1 and BCL-X$_L$, the combination of ABT-737 (IC$_{50}$, 5.1 μM) and MIM1 (IC$_{50}$, 10.6 μM) resulted in synergistic cytotoxicity, as determined by CalcuSyn analysis[36] (IC$_{50}$, 1.4 μM; CI at ED$_{50}$, 0.47) (FIG. 13). Strikingly, when the combination was applied to MCL-1-reconstituted p185$^+$Arf$^{-/-}$Mcl-1$^{-/-}$ cells, the addition of ABT-737 had little effect (FIG. 14A). Similarly, the cytotoxic effects of single agent ABT-737 and the combination on BCL-X$_L$-reconstituted p185$^+$Arf$^{-/-}$Mcl-1$^{-/-}$ cells were identical, reflecting no added benefit of MIM1 in the absence of MCL-1 (FIG. 14B). These data underscore the selectivity of MIM1 and ABT-737 for their respective targets in the context of high stringency cancer cell dependence on MCL-1 or BCL-X$_L$. Importantly, the relative resistance of non-malignant fibroblasts to MIM1 treatment, as previously observed for ABT-737[28], suggests that a therapeutic window may exist, with preferential toxicity to cells driven by discrete anti-apoptotic blockades.

Example 5

MCL-1 Binding Potency Correlates with the Degree of Cytotoxicity in MCL-1 Dependent Leukemia Cells Medicinal chemistry-based optimization of MIM1 led to MIM1 analogs with increased MCL-1 binding potency (FIG. 16). A series of analogs with increased potency compared to MIM1 manifested increased cytotoxicity in MCL-1 dependent leukemia cells (FIG. 17). A series of compounds with variable potency in competitive binding to MCL-1ΔNΔC correspondingly manifested a degree of cytotoxicity that correlated with MCL-1 binding affinity (FIG. 18).

Example 6

MIM1 Analogs with Dual Binding Activity Toward MCL-1 and BFL-1/A1

Some of the MCL-1 inhibitor compounds described herein, including MIM1, also bind tightly to BFL1/A1ΔC (FIGS. 16, 19, 20A, 21), which has been shown to be an important anti-apoptotic protein of the BCL-2 family and implicated in oncogenesis and chemoresistance. Thus, we provide examples of small molecules with dual specificity in targeting both the MCL-1 and BFL-1/A1 anti-apoptotic proteins.

Example 7

Selective Targeting of BFL-1/A1 by Distinct MIM1 Analogs

Some of the MIM1 analogs described herein (FIG. 20B) bind tightly to BFL1/A1ΔC (FIG. 22A) but show little to no interaction with MCL-1ΔNΔC (FIG. 22B), exemplifying compounds of the formula (I)/(II) that selectively target BFL-1/A1.

Example 8

Methods

SAHB Synthesis

Hydrocarbon-stapled peptides corresponding to BCL-2 family BH3 domains and their FITC-βAla derivatives were synthesized, purified, and characterized according to previously described methods[19, 32, 37]. The sequence compositions of all SAHBs used in this study are indicated in Table S1.

TABLE S1

(SEQ ID NOs: 1-6)

| Peptide | Sequence | N-terminus | MW | M/3 |
|---|---|---|---|---|
| MCL-1 SA\|HB$_A$ | KALETLRXVGDXVQRNHETAF | FITC-βAla- | 2893 | 965.5 |
| MCL-1 SAHB$_D$ | KALETLRRVGDGVXRNHXTAF | Acetyl-βAla- | 2502 | 835.0 |
| MCL-1 SAHB$_D$ | KALETLRRVGDGVXRHNHXTAF | FITC-βAla- | 2850 | 950.8 |
| BAD SAHB$_A$ | NLWAAQRYGRELRXBSDXFVDSFKK | Acetyl- | 3090 | 1030.9 |
| BID SAHB$_A$ | DIIRNIARHLAXVGDXBDRSI | Acetyl- | 2438 | 813.7 |
| BCL-2 SAHB$_A$ | VVHLTRXAGDXFSRRY | Acetyl- | 2082 | 694.4 |

BCL-2 Family Protein Production

Recombinant MCL-1ΔNΔC, BCL-X$_L$ΔC, BFL-1/A1, and full-length BAX were expressed and purified as previously reported[30,38]. Transformed *Escherichia coli* BL21 (DE3) were cultured in ampicillin-containing Luria Broth, and protein expression was induced with 0.5 mM isopropyl β-D-1-thiogalactopyranoside (IPTG). The bacterial pellets were resuspended in buffer (1% Triton X-100 in PBS, complete protease inhibitor tablet for MCL-1ΔNΔC, BCL-X$_L$ΔC, and BFL-1/A1, and 250 mM NaCl, 20 mM Tris, complete protease inhibitor tablet, pH 7.2 for BAX), sonicated, and after centifugation at 45,000×g for 45 min, the supernatants were applied to glutathione-sepharose columns (GE Healthcare) for GST-MCL-1ΔNΔC, BCL-X$_L$ΔC, and BFL-1/A1, or a chitin column (BioLabs) for Intein-BAX. On-bead digestion of GST-tagged protein was accomplished by overnight incubation at room temperature in the presence of thrombin (75 units) in PBS (3 mL), whereas the intein tag was cleaved from BAX by overnight incubation of the chitin beads at 4° C. with 50 mM DTT. MCL-1ΔNΔC, BCL-X$_L$ΔC, and BFL-1/A1 were purified by size exclusion chromatography (SEC) using 150 mM NaCl, 50 mM Tris, pH 7.4 buffer conditions, and full-length monomeric BAX protein was isolated by SEC using a Superdex-75 column (GE Healthcare) using 20 mM HEPES pH 7.2, 150 mM KCl buffer conditions.

Fluorescence Polarization Binding Assays

Fluorescence polarization assays (FPA) were performed as previously described[38,39]. Briefly, direct binding curves were first generated by incubating FITC-MCL-1 SAHB$_A$, FITC-BID BH3, or FITC-BAD BH3 (15 nM) with serial dilutions of anti-apoptotic protein, and fluorescence polarization measured at 5 minutes on a SpectraMax M5 microplate reader (Molecular Devices). For competition assays, a serial dilution of small molecule or acetylated peptide was added to recombinant protein at ~EC$_{75}$ concentration, as determined by the direct binding assay (e.g. MCL-1 ΔNΔC, 45 nM; BCL-X$_L$ΔC, 300 nM). Fluorescence polarization was measured at equilibrium and IC$_{50}$ values calculated by nonlinear regression analysis of competitive binding curves using Prism software (Graphpad).

High-Throughput Screening

Small molecule screening was performed at the Institute for Chemistry and Cellular Biology (ICCB) at Harvard Medical School, utilizing the commercial libraries Asinex1 (12,378 molecules), Chembridge3 (10,560 molecules), ChemDiv4 (14,677 molecules), Enamine2 (26,576), Life Chemicals1 (3,893 molecules), and Maybridge5 (3,212 molecules). High-throughput competitive FP binding assays were employed to screen for small molecules that disrupted the FITC-MCL-1 SAHB$_A$/MCL-1ΔNΔC, but not the FITC-BAD BH3/BCL-X$_L$ΔC, interaction. SEC-purified MCL-1ΔNΔC or BCL-X$_L$ΔC (see above) was delivered by automated liquid handler (WellMate, Matrix) to 384 well plates, followed by addition of small molecule libraries (~5 mg/mL, 100 nL). After a 15 min incubation at room temperature, the corresponding FITC-SAHB (15 nM) was added to each well by liquid handler and FP read at 1 h using a PerkinElmer Envision plate reader ($\lambda_{ex}$ 480 nm, $\lambda_{em}$ 535 nm).

MIM1 Characterization by Mass Spectrometry and $^1$H-NMR Spectroscopy 4-((E)-(((Z)-2-(cyclohexylimino)-4-methylthiazol-3(2H)-yl)imino)methyl)benzene-1,2,3-triol. LC-MS: 348 (M+1, ES+); 346 (M−1, ES−). $^1$H NMR (300 MHz, DMSO-d6): d 11.35 (s, 1H, —OH); 9.3 (s, 1H, —OH); 8.42 (s, 1H, —OH); 8.31 (s, 1H); 6.73 (d, 1H, J=8.4 Hz); 6.34 (d, 1H, J=8.4 Hz); 6.01 (s, 1H); 3.09-3.05 (m, 1H); 2.15 (s, 3H); 1.81-1.60 (m, 5H); 1.40-1.2 (m, 3H); 1.15 (t, 2H).

NMR Samples and Spectroscopy

Uniformly $^{15}$N-labeled MCL-1 ΔNΔC was generated by modifying its expression and purification scheme in accordance with the method for producing $^{15}$N-BAX[30,40]. Protein samples were prepared in 20 mM HEPES solution at pH 6.5 in 5% D$_2$O. MIM1 (20 mM stock) was titrated into a solution of 100 μM MCL-1ΔNΔC to achieve the indicated molar ratio concentration. Correlation $^1$H-$^{15}$N HSQC spectra[41] were acquired at 25° C. on a Bruker 800 MHz NMR spectrometer equipped with a cryogenic probe, processed using NMRPipe[42], and analyzed with NMRView[43]. The weighted average chemical shift difference Δ at the indicated molar ratio was calculated as $\sqrt{\{(\Delta H)^2+(\Delta N/5)^2\}/2}$ in p.p.m. The absence of a bar indicates no chemical shift difference, or the presence of a proline or residue that is overlapped or not assigned. MCL-1ΔNΔC cross-peak assignments were applied as previously reported[40]. The significance threshold for backbone amide chemical shift changes was calculated based on the average chemical shift across all residues plus the standard deviation, in accordance with standard methods[44].

Structure Modeling

Docked structures of MCL-1ΔNΔC and MIM1 were generated using Glide and analyzed using PYMOL[45].

Liposomal Release Assay

Liposomes were prepared and release assays performed as previously described[46,47]. Liposomal composition reflects a mixture of the following molar percentages of lipids (Avanti Polar Lipids): phosphatidylcholine, 48%; phosphatidylethanolamine, 28%; phosphatidylinositol, 10%; dioleoyl phosphatidylserine, 10%; and tetraoleoyl cardiolipin, 4%. Aliquots of mixed lipids (1 mg total) are stored in glass at −20° C. under nitrogen, and before use, resuspended in liposome assay buffer (10 mM HEPES, 200 mM KCl, 1 mM $MgCl_2$, pH 7) containing 12.5 mM of the fluorescent dye ANTS (8-aminonaphthalene-1,3,6-trisulfonic acid, disodium salt) and 45 mM of the quencher DPX (p-xylene-bis-pyridinium bromide. The resulting slurry is vortexed for 10 min and freeze-thawed five times in liquid nitrogen and a 40° C. water bath, respectively. The solution is then passed through an Avanti Mini-Extruder Set (#610000) equipped with a 100 nm filter, followed by passage through a Sepharose column (GE Healthcare) to remove residual ANTS/DPX. The liposomes are brought up to a volume of 3 mL to produce a final liposome stock. For the liposomal release assay, a total volume of 30 μL is used in 384 well black flat-bottom plates (Costar), and baseline fluorescent measurements of 8 μL liposomes are made for 10 min using a Tecan Infinite M1000 ($\lambda_{ex}$ 355 nm, $\lambda_{em}$ 520 nm). Following the baseline read, recombinant anti-apoptotic protein, with or without pre-incubated small molecule or peptide, is added to the liposomes. Subsequently, 20 nM caspase-cleaved mouse BID (R&D systems) and 250 nM purified recombinant monomeric BAX is added, and fluorescence measurements are recorded each minute until the release measurements plateau, at which point the liposomes are quenched with 0.2% Triton X-100 (100% release). The percentage release of ANTS/DPX is calculated as percentage release=((F−F0)/(F100−F0))×100, where F0 and F100 are baseline and maximal fluorescence, respectively.

Cell Viability and Caspase 3/7 Activation Assays $p185^+Arf^{-/-}$ and MCL-1 or $BCL-X_L$-rescued $p185^+Arf^{-/-}$ $Mcl^{-/-}$ cells were maintained in RPMI 1640 (ATCC) supplemented with 10% (v/v) FBS, 100 U/mL penicillin, 100 μg/mL streptomycin, 0.1 mM MEM non-essential amino acids and 50 μM β-mercaptoethanol. Mouse embryonic fibroblasts (MEFs) cells were maintained in DMEM high glucose (Invitrogen) supplemented with 10% (v/v) FBS, 100 U/mL penicillin, 100 μg/mL streptomycin, 2 mM L-glutamine, 50 mM HEPES, 0.1 mM MEM non-essential amino acids and 50 μM β-mercaptoethanol. Leukemia cells ($4\times10^4$/well) were seeded in 96-well opaque plates and incubated with the indicated serial dilutions of vehicle (0.4% DMSO), MIM1, ABT-737, or the combination in DMEM at 37° C. in a final volume of 100 μl. For MEF experiments, cells ($5\times10^3$/well) were seeded in 96-well opaque plates for 24 h and then incubated with the indicated serial dilutions of vehicle (0.4% DMSO), MIM1, or ABT-737. Cell viability was assayed at 24 h by addition of CellTiter-Glo reagent according to the manufacturer's protocol (Promega), and luminescence was measured using a SpectraMax M5 microplate reader (Molecular Devices). Caspase 3/7 activation was assayed at 8 h by addition of Caspase-Glo 3/7 reagent according to manufacturer's protocol (Promega), and luminescence measured using a SpectraMax M5 microplate reader. Viability and caspase assays were performed in duplicate, repeated at least twice with independent cell cultures, and the data normalized to vehicle-treated control wells. Synergy of the MIM1/ABT-737 combination in leukemia cells was calculated using the CalcuSyn software package[36].

Example 9

Synthesis Examples

Example A

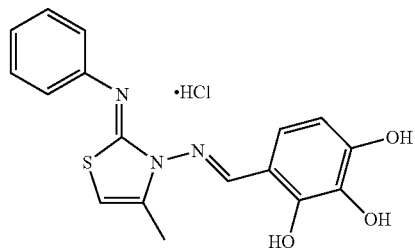

CGDF-183-20

The molecule 183-20 was synthesized according to the scheme (Scheme 1) shown below.

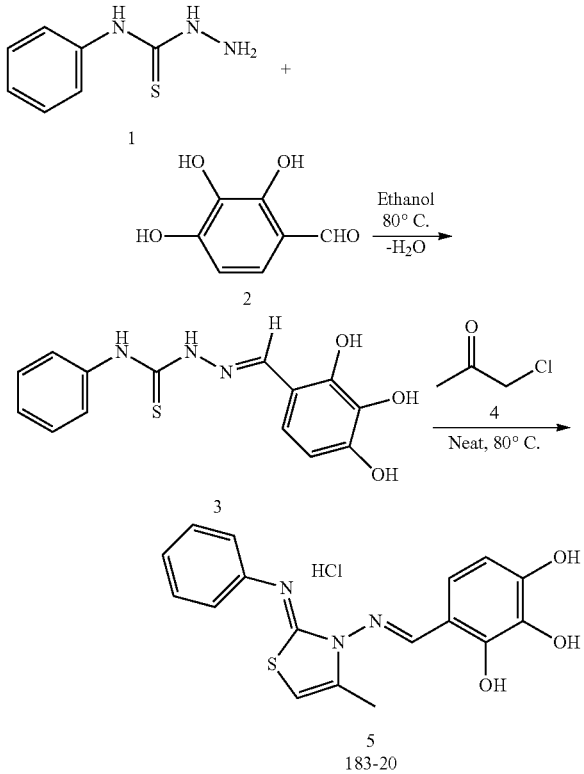

Scheme 1

Procedure: A mixture of 4-phenylthiosemicarbazide 1 (100 mg, 0.6 mmol) and trihydroxy benzaldehyde 2 (93 mg, 0.6 mmol) in 4 mL absolute ethanol was refluxed in a sealed tube for 6 hours. The solvent was evaporated off and the residue was triturated with ether-hexane (1:1) mixture to afford the product 3 [143 mg, 79%; LC-MS: m/z 304 (M+1)]. This product was used for the next step without purification. A mixture of 3 (50 mg, 0.165 mmol) and chloroacetone 4 (153 mg, 1.65 mmol) was heated at 80° C. for 10 minutes. LC-MS analysis indicated completion of the reaction. The reaction mixture was cooled to room temperature and washed with dry ether (×3), dry THF (×1), hexane (×1) and dried under vacuum to afford the product 5 [42 mg, 68%; LC-MS: m/z 342 (M+1)] as HCl salt.

Example B

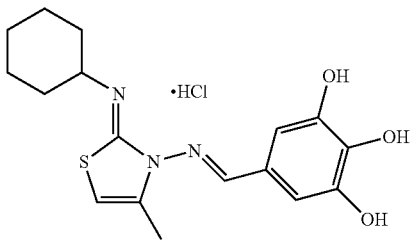

CGDF-183-84

The molecule 183-84 was synthesized according to the scheme (Scheme 2) shown below.

Scheme 2

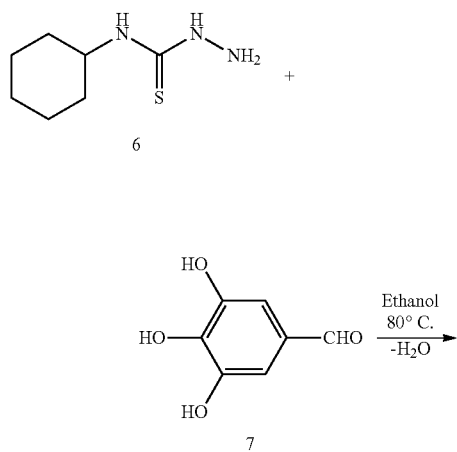

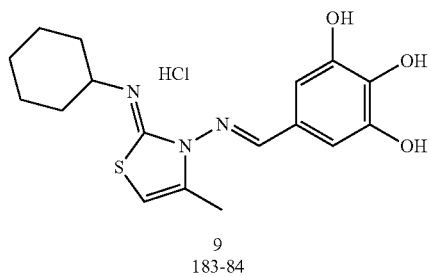

9
183-84

Procedure: A mixture of 4-cyclohexylthiosemicarbazide 6 (150 mg, 0.87 mmol) and trihydroxy benzaldehyde 7 (134 mg, 0.87 mmol) in 5 mL absolute ethanol was refluxed in a sealed tube for 8 hours. The solvent was evaporated off and the residue was triturated with ether-hexane (1:1) mixture to afford the product 8 [210 mg, 78%; LC-MS: m/z 310 (M+1)]. This product was used for the next step without purification. A mixture of 8 (50 mg, 0.16 mmol) and chloroacetone 4 (150 mg, 1.62 mmol) was heated at 80° C. for 10 minutes. LC-MS analysis indicated completion of the reaction. The reaction mixture was cooled to room temperature and washed with dry ether (×3), dry THF (×1), hexane (×1) and dried under vacuum to afford the product 9 [35 mg, 56%; LC-MS: m/z 348 (M+1)] as HCl salt.

Example C

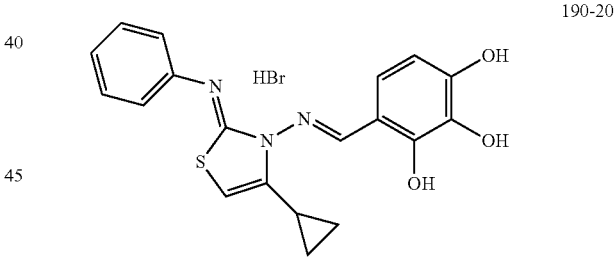

190-20

The molecule 190-20 was synthesized according to the scheme (Scheme 3) shown below.

Scheme 3

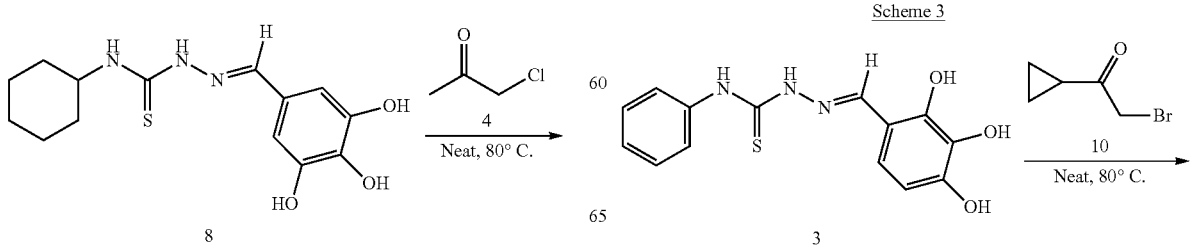

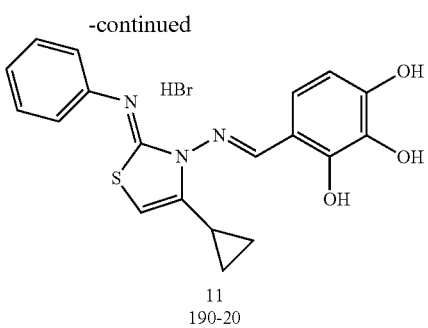

11
190-20

Procedure: A mixture of 3 (75 mg, 0.25 mmol) and 2-bromo 1-cyclproyl ethanone 10 (202 mg, 1.25 mmol) was heated at 80° C. for 10 minutes. LC-MS analysis indicated completion of the reaction. The reaction mixture was cooled to room temperature and washed with dry ether (×3), dry THF (×2), hexane (×1) and dried under vacuum to afford the product 11 [77 mg, 69%; LC-MS: m/z 368 (M+1)] as HBr salt.

Example D

CGDF-183-91

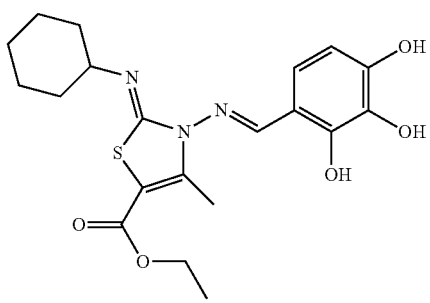

The molecule 183-91 was synthesized according to the scheme (Scheme 4) shown below.

Scheme 4

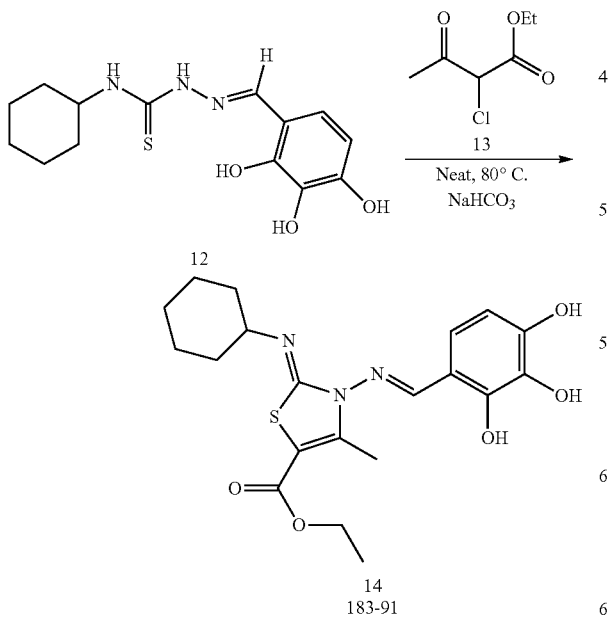

Procedure: A mixture of 12 (100 mg, 0.323 mmol) and ethyl 2-chloro acetoacetate 13 (530 mg, 0.323 mmol) was heated at 80° C. for 30 minutes. LC-MS analysis indicated completion of the reaction. The reaction mixture was cooled to room temperature and dissolved in dry THF (4 mL). The reaction mixture was neutralized with saturated sodium bicarbonate to adjust the pH to 7. The crude product was adsorbed onto silica gel and subjected to column chromatography using 0-30% ethyl acetate in hexane to afford the product 14 [62 mg, 46%; LC-MS: m/z 420 (M+1)]

Example E

CGDF-183-76

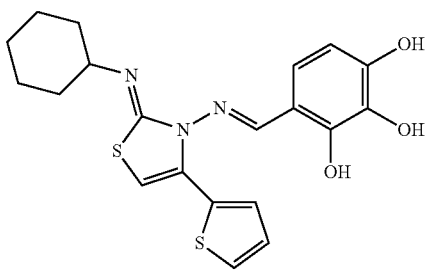

The molecule 183-76 was synthesized according to the scheme (Scheme 5) shown below.

Scheme 5

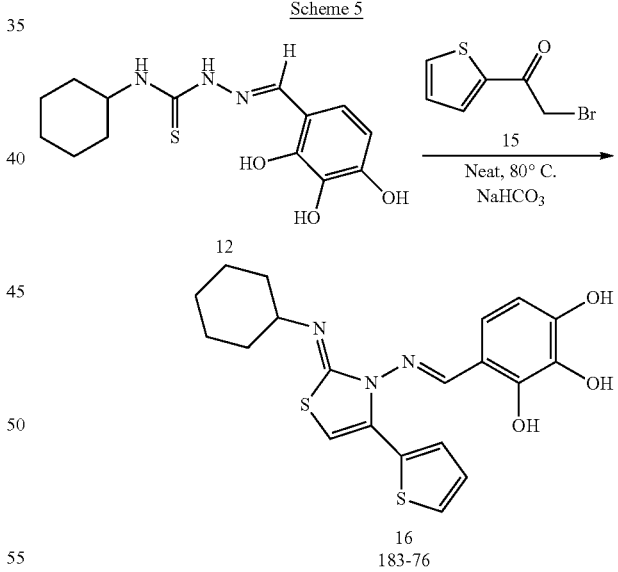

Procedure: A mixture of 12 (50 mg, 0.161 mmol) and 2-bromo acetylthiophene 15 (165 mg, 0.807 mmol) was heated at 80° C. for 10 minutes. LC-MS analysis indicated completion of the reaction. The reaction mixture was cooled to room temperature and dissolved in dry THF (3 mL). The reaction mixture was neutralized with saturated sodium bicarbonate to adjust the pH to 7. The crude product was adsorbed onto silica gel and subjected to column chromatography using 0-30% ethyl acetate in hexane to afford the product 16 [34 mg, 51%; LC-MS: m/z 416 (M+1)].

Example F

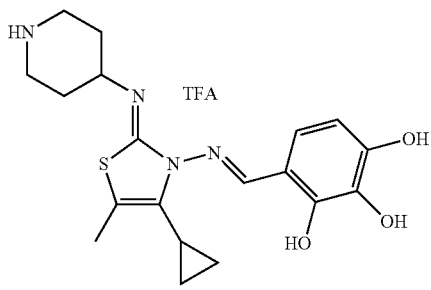

CGDF-187-58

The molecule 187-58 was synthesized according to the scheme (Scheme 6) shown below

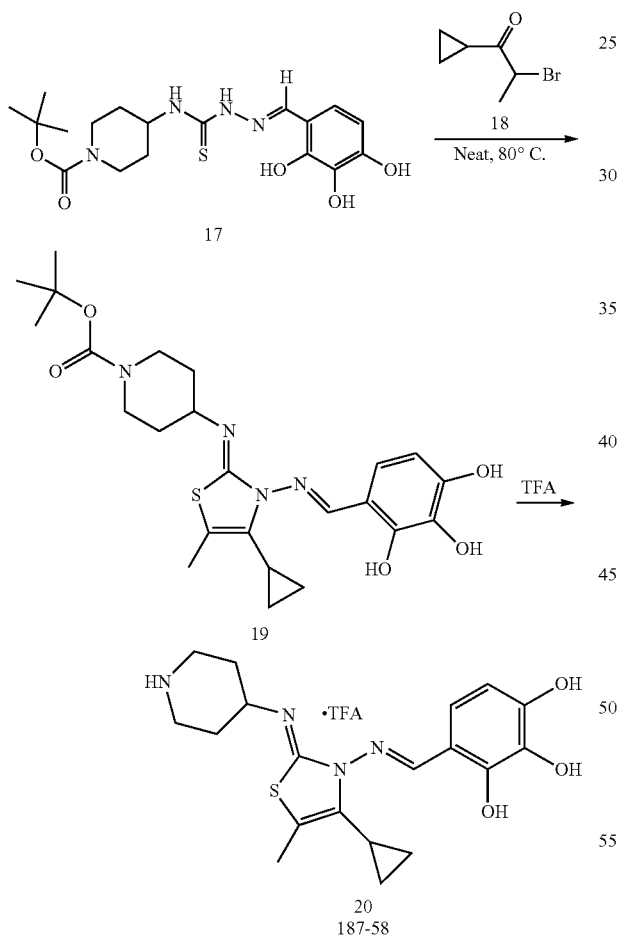

Scheme 6

Procedure: A mixture of 17 (50 mg, 0.122 mmol) and bromo compound 18 (165 mg, 0.49 mmol) was heated at 80° C. for 10 minutes. LC-MS analysis indicated completion of the reaction. The reaction mixture was cooled to room temperature and dissolved in dry THF (3 mL). The reaction mixture was neutralized with saturated sodium bicarbonate to adjust the pH to 7. The crude product was adsorbed onto silica gel and subjected to column chromatography using 0-60% ethyl acetate in hexane to afford the product 19 [21 mg, 35%; LC-MS: m/z 489 (M+1)]. This product was treated with trifluoroacetic acid to obtain the product 20 [7 mg, 42%; LC-MS: m/z 389 (M+1)].

Example G

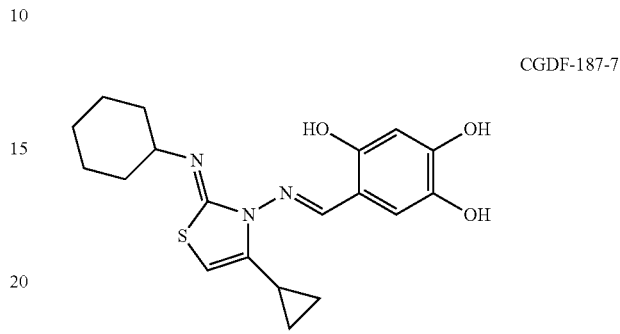

CGDF-187-7

The molecule 187-7 was synthesized according to the scheme (Scheme 7) shown below

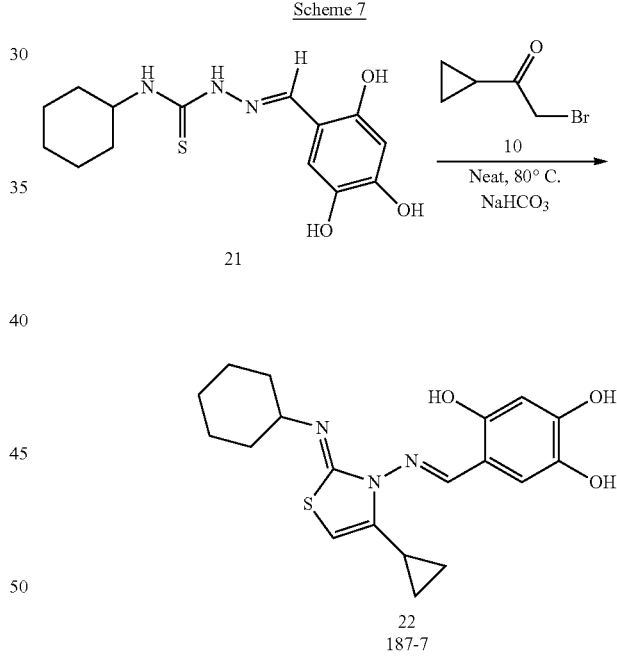

Scheme 7

Procedure: A mixture of 21 (50 mg, 0.162 mmol) and bromo compound 10 (131 mg, 0.81 mmol) was heated at 80° C. for 10 minutes. LC-MS analysis indicated completion of the reaction. The reaction mixture was cooled to room temperature and dissolved in dry THF (2 mL). The reaction mixture was neutralized with saturated sodium bicarbonate to adjust the pH to 7. The crude product was adsorbed onto silica gel and subjected to column chromatography using 0-30% ethyl acetate in hexane to afford the product 22 [27 mg, 48%; LC-MS: m/z 374 (M+1)].

Example H

CGDF-183-87

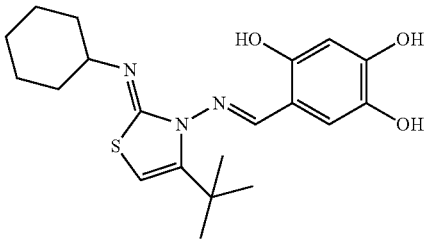

The molecule 183-87 was synthesized according to the scheme (Scheme 8) shown below

Scheme 8

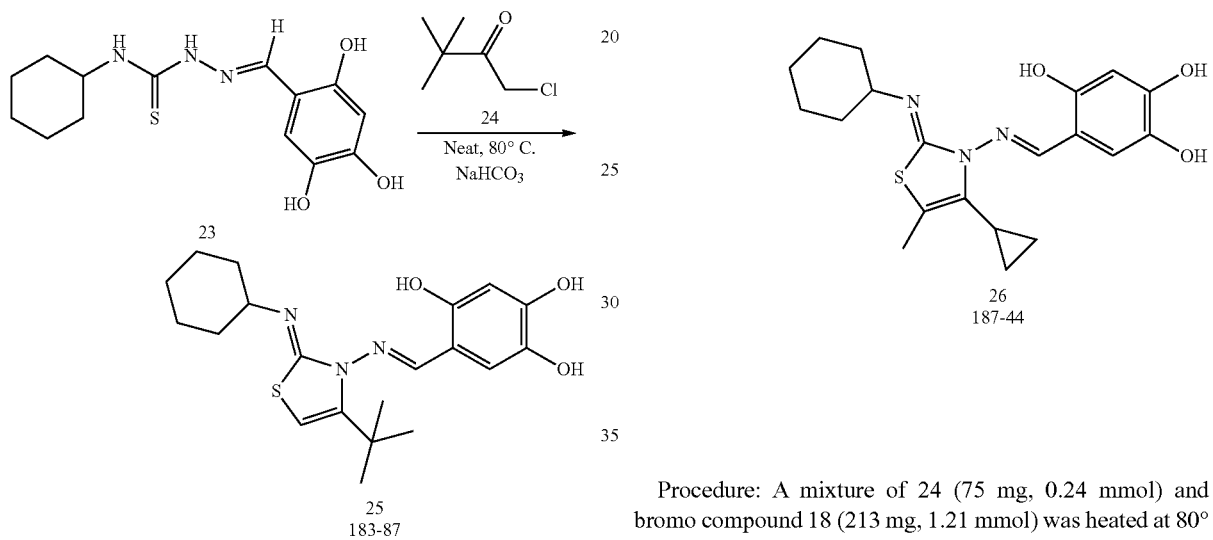

Procedure: A mixture of 23 (60 mg, 0.19 mmol) and chloropinacolone 24 (156 mg, 1.16 mmol) was heated at 80° C. for 45 minutes. LC-MS analysis indicated completion of the reaction. The reaction mixture was cooled to room temperature and dissolved in dry THF (3 mL). The reaction mixture was neutralized with saturated sodium bicarbonate to adjust the pH to 7. The crude product was adsorbed onto silica gel and subjected to column chromatography using 0-30% ethyl acetate in hexane to afford the product 25 [36 mg, 48%; LC-MS: m/z 390 (M+1)].

Example I

CGDF-187-44

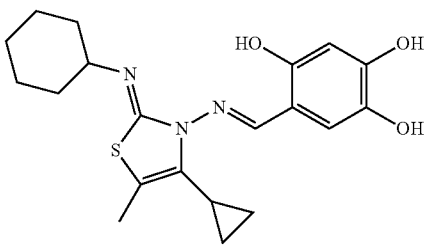

The molecule 187-44 was synthesized according to the scheme (Scheme 9) shown below

Scheme 9

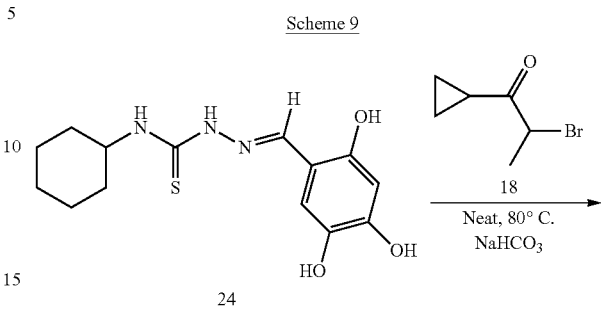

Procedure: A mixture of 24 (75 mg, 0.24 mmol) and bromo compound 18 (213 mg, 1.21 mmol) was heated at 80° C. for 60 minutes. LC-MS analysis indicated completion of the reaction. The reaction mixture was cooled to room temperature and dissolved in dry THF (3 mL). The reaction mixture was neutralized with saturated sodium bicarbonate to adjust the pH to 7. The crude product was adsorbed onto silica gel and subjected to column chromatography using 0-30% ethyl acetate in hexane to afford the product 26 [41 mg, 44%; LC-MS: m/z 387 (M+1)].

Example J

CGDF-183-89

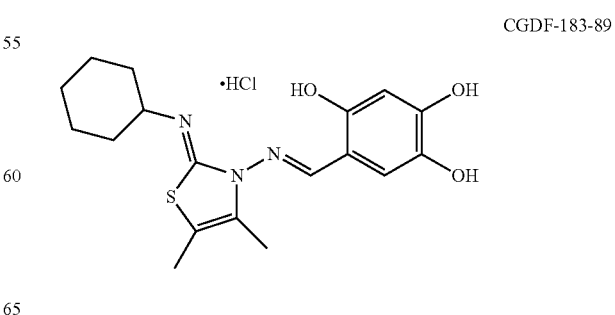

The molecule 183-89 was synthesized according to the scheme (Scheme 10) shown below Scheme 10

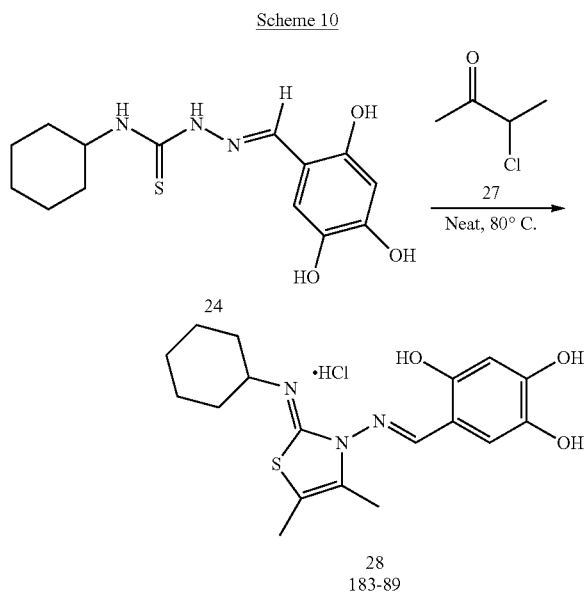

Procedure: A mixture of 24 (50 mg, 0.162 mmol) and chloro butanone 27 (103 mg, 0.97 mmol) was heated at 80° C. for 60 minutes. LC-MS analysis indicated completion of the reaction. The reaction mixture was cooled to room temperature and washed with dry ether (×3), dry THF (×1), hexane (×1) and dried under vacuum to afford the product 28 [38 mg, 65%; LC-MS: m/z 362 (M+1)] as HCl salt.

REFERENCES

1. Llambi, F. & Green, D. R. Apoptosis and oncogenesis: give and take in the BCL-2 family. *Curr Opin Genet Dev* 21, 12-20 (2011).
2. Youle, R. J. & Strasser, A. The BCL-2 protein family: opposing activities that mediate cell death. *Nat Rev Mol Cell Biol* 9, 47-59 (2008).
3. Tsujimoto, Y., Finger, L. R., Yunis, J., Nowell, P. C. & Croce, C. M. Cloning of the chromosome breakpoint of neoplastic B cells with the t(14;18) chromosome translocation. *Science* 226, 1097-1099 (1984).
4. Tsujimoto, Y., Cossman, J., Jaffe, E. & Croce, C. M. Involvement of the bcl-2 Gene in Human Follicular Lymphoma. *Science* 228, 1440-1443 (1985).
5. Vaux, D. L., Cory, S. & Adams, J. M. Bcl-2 gene promotes haemopoietic cell survival and cooperates with c-myc to immortalize pre-B cells. *Nature* 335, 440-442 (1988).
6. Frenzel, A., Grespi, F., Chmelewskij, W. & Villunger, A. Bcl2 family proteins in carcinogenesis and the treatment of cancer. *Apoptosis* 14, 584-96 (2009).
7. Kang, M. H. & Reynolds, C. P. Bcl-2 inhibitors: targeting mitochondrial apoptotic pathways in cancer therapy. *Clin Cancer Res* 15, 1126-32 (2009).
8. Chen, L. et al. Differential targeting of prosurvival Bcl-2 proteins by their BH3-only ligands allows complementary apoptotic function. *Mol Cell* 17, 393-403 (2005).
9. Sattler, M. et al. Structure of Bcl-xL-Bak peptide complex: recognition between regulators of apoptosis. *Science* 275, 983-6 (1997).
10. Shamas-Din, A., Brahmbhatt, H., Leber, B. & Andrews, D. W. BH3-only proteins: Orchestrators of apoptosis. *Biochim Biophys Acta* 1813, 508-20 (2011).
11. Walensky, L. D. & Gavathiotis, E. BAX unleashed: the biochemical transformation of an inactive cytosolic monomer into a toxic mitochondrial pore. *Trends Biochem Sci* 36, 642-52 (2011).
12. Degterev, A. et al. Identification of small-molecule inhibitors of interaction between the BH3 domain and Bcl-xL. *Nat Cell Biol* 3, 173-82 (2001).
13. Enyedy, I. J. et al. Discovery of small-molecule inhibitors of Bcl-2 through structure-based computer screening. *J Med Chem* 44, 4313-24 (2001).
14. Kitada, S. et al. Discovery, characterization, and structure-activity relationships studies of proapoptotic polyphenols targeting B-cell lymphocyte/leukemia-2 proteins. *J Med Chem* 46, 4259-64 (2003).
15. Nguyen, M. et al. Small molecule obatoclax (GX15-070) antagonizes MCL-1 and overcomes MCL-1-mediated resistance to apoptosis. *Proc Natl Acad Sci USA* 104, 19512-7 (2007).
16. Oltersdorf, T. et al. An inhbitor of Bcl-2 family proteins induces regression of solid tumours. *Nature* 435, 677-681 (2005).
17. Petros, A. M. et al. Discovery of a potent and selective Bcl-2 inhibitor using SAR by NMR. *Bioorg Med Chem Lett* 20, 6587-91 (2010).
18. Tzung, S. P. et al. Antimycin A mimics a cell-death-inducing Bcl-2 homology domain 3. *Nat Cell Biol* 3, 183-91 (2001).
19. Walensky, L. D. et al. Activation of apoptosis in vivo by a hydrocarbon-stapled BH3 helix. *Science* 305, 1466-70 (2004).
20. Wang, G. et al. Structure-based design of potent small-molecule inhibitors of anti-apoptotic Bcl-2 proteins. *J Med Chem* 49, 6139-42 (2006).
21. Wang, J. L. et al. Structure-based discovery of an organic compound that binds Bcl-2 protein and induces apoptosis of tumor cells. *Proc Natl Acad Sci USA* 97, 7124-9 (2000).
22. Tse, C. et al. ABT-263: a potent and orally bioavailable Bcl-2 family inhibitor. *Cancer Res* 68, 3421-8 (2008).
23. Wilson, W. H. et al. Navitoclax, a targeted high-affinity inhibitor of BCL-2, in lymphoid malignancies: a phase 1 dose-escalation study of safety, pharmacokinetics, pharmacodynamics, and antitumour activity. *Lancet Oncol* 11, 1149-59 (2010).
24. Gandhi, L. et al. Phase I study of Navitoclax (ABT-263), a novel Bcl-2 family inhibitor, in patients with small-cell lung cancer and other solid tumors. *J Clin Oncol* 29, 909-16 (2011).
25. Roberts, A. W. et al. Substantial susceptibility of chronic lymphocytic leukemia to BCL2 inhibitio: Results of Phase 1 study of navitoclax (ABT-263) in patients with relapsed or refractory disease. *J Clin Onc* (2011).
26. Konopleva, M. et al. Mechanisms of apoptosis sensitivity and resistance to the BH3 mimetic ABT-737 in acute myeloid leukemia. *Cancer Cell* 10, 375-388 (2006).
27. Lin, X. et al. "Seed" analysis of off-target siRNAs reveals an essential role of MCL-1 in resistance to the small-molecule Bcl-2/Bcl-xL inhibitor ABT-737. *Oncogene* 26, 3972-3979 (2007).
28. van Delft, M. F. et al. The BH3 mimetic ABT-737 targets selective Bcl-2 proteins and efficiently induces apoptosis via Bak/Bax if Mcl-1 is neutralized. *Cancer Cell* 10, 389-399 (2006).
29. Yecies, D., Carlson, N. E., Deng, J. & Letai, A. Acquired resistance to ABT-737 in lymphoma cells that up-regulate MCL-1 and BFL-1. *Blood* 115, 3304-13 (2010).
30. Gavathiotis, E. et al. BAX activation is initiated at a novel interaction site. *Nature* 455, 1076-81 (2008).

31. Walensky, L. D. et al. Activation of apoptosis in vivo by a hydrocarbon stapled BH3 helix. *Science* 305, 1466-1470 (2004).
32. Walensky, L. D. et al. A stapled BID BH3 helix directly binds and activates BAX. *Mol Cell* 24, 199-210 (2006).
33. Beroukhim, R. et al. The landscape of somatic copy-number alteration across human cancers. *Nature* 463, 899-905 (2010).
34. Stewart, M. L., Fire, E., Keating, A. E. & Walensky, L. D. The MCL-1 BH3 helix is an exclusive MCL-1 inhibitor and apoptosis sensitizer. *Nature Chem Biol* 6, 595-601 (2010).
35. Zhai, D., Jin, C., Satterthwait, A. C. & Reed, J. C. Comparison of chemical inhibitors of antiapoptotic BCL-2 family proteins. *Cell Death Diff* 13, 1419-1421 (2006).
36. Chou, T. C. Theoretical basis, experimental design, and computerized simulation of synergism and antagonism in drug combination studies. *Pharmacol. Rev.* 58, 621-681 (2006).
37. Bird, G. H., Bernal, F., Pitter, K. & Walensky, L. D. Chapter 22 Synthesis and Biophysical Characterization of Stabilized alpha-Helices of BCL-2 Domains. *Methods Enzymol* 446, 369-86 (2008).
38. Pitter, K., Bernal, F., Labelle, J. & Walensky, L. D. Dissection of the BCL-2 family signaling network with stabilized alpha-helices of BCL-2 domains. *Methods Enzymol* 446, 387-408 (2008).
39. Bernal, F. et al. A stapled p53 helix overcomes HDMX-mediated suppression of p53. *Cancer Cell* 18, 411-22 (2010).
40. Suzuki, M., Youle, R. J. & Tjandra, N. Structure of Bax: coregulation of dimer formation and intracellular localization. *Cell* 103, 645-54 (2000).
41. Grzesiek, S. & Bax, A. The importance of not saturating water in protein NMR: application to sensitivity enhancement and NOE measurements. *J Am Chem Soc* 115, 12593-12594 (1993).
42. Delaglio, F. et al. NMRPipe: a multidimensional spectral processing system based on UNIX pipes. *J Biomol NMR* 6, 277-93 (1995).
43. Johnson, B. A. Using NMRView to visualize and analyze the NMR spectra of macromolecules. *Methods Mol Biol* 278, 313-52 (2004).
44. Marintchev, A., Frueh, D. & Wagner, G. NMR methods for studying protein-protein interactions involved in translation initiation. *Methods Enzymol* 430, 283-331 (2007).
45. DeLano, W. L. *The PyMOL Molecular Graphics System*, (DeLano Scientific, San Carlos, 2002).
46. Yethon, J. A., Epand, R. F., Leber, B., Epand, R. M. & Andrews, D. W. Interaction with a membrane surface triggers a reversible conformational change in Bax normally associated with induction of apoptosis. *J Biol Chem* 278, 48935-41 (2003).
47. Lovell, J. F. et al. Membrane binding by tBid initiates an ordered series of events culminating in membrane permeabilization by Bax. *Cell* 135, 1074-84 (2008).

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical combination comprising a compound of formula (II), or a pharmaceutically acceptable salt thereof; and one or more additional therapeutic agents selected from the group consisting of chemotherapeutic agents and therapeutic agents that modulate apoptosis, or a pharmaceutically acceptable salt of the agent:

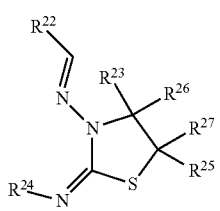

(II)

wherein:

$R^{22}$ is:
- (i) $C_6$-$C_{10}$ aryl, which is optionally substituted with from 1-5 independently selected $R^a$;
- (ii) heteroaryl, which contains from 5-10 ring atoms, wherein from 1-4 of the ring atoms is independently selected from the group consisting of N, NH, N($C_1$-$C_3$ alkyl), O, and S; and wherein said heteroaryl ring is optionally substituted with from 1-4 independently selected $R^a$; or
- (iii) phenyl fused to $C_1$-$C_3$ alkylenedioxy, wherein the phenyl portion is optionally substituted with from 1-2 independently selected $R^a$;

$R^{23}$ is:
- (i) $C_3$-$C_8$ branched alkyl or $C_1$-$C_8$ haloalkyl, each of which is optionally substituted with from 1-2 independently selected $R^b$; or
- (ii) $C_3$-$C_6$ cycloalkyl or $C_3$-$C_6$ cycloalkenyl, each of which is optionally substituted with from 1-4 independently selected $R^d$;

$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl);
or $R^{23}$ and $R^{25}$, together with the carbon atoms to which each is attached, form:
(i) a 5-6 membered saturated or unsaturated carbocyclic ring, which is optionally substituted with from 1-4 independently selected $R^d$; or
(ii) a 5-6 membered saturated or unsaturated hetrocyclic ring, which is optionally substituted with from 1-4 independently selected $R^d$, and wherein from 1-2 of the ring atoms (other than the two ring atoms attached to $R^{23}$ and $R^{24}$) is independently selected from the group consisting of N, NH, N($C_1$-$C_3$ alkyl), NC(O)($C_1$-$C_6$ alkyl), O, and S;

$R^{26}$ and $R^{27}$ together are a bond (form a second or double bond between the carbon atoms to which each is attached); or
each of $R^{26}$ and $R^{27}$ is independently selected from the group consisting of hydrogen, halo, and hydroxyl;

$R^{24}$ is:
(i) $C_3$-$C_{10}$ cycloalkyl or $C_3$-$C_{10}$ cycloalkenyl, each of which is optionally substituted with from 1-4 independently selected $R^d$;
(ii) $C_6$-$C_{10}$ aryl, which is optionally substituted with from 1-5 independently selected $R^c$;
(iii) heteroaryl, which contains from 5-10 ring atoms, wherein from 1-4 of the ring atoms is independently selected from the group consisting of N, NH, N($C_1$-$C_3$ alkyl), O, and S; and wherein said heteroaryl ring is optionally substituted with from 1-4 independently selected $R^c$;
(iv) unsubstituted $C_1$-$C_8$ alkyl or unsubstituted $C_1$-$C_8$ haloalkyl;
(v) heterocyclyl containing from 3-6 ring atoms, wherein from 1-2 of the ring atoms is independently selected from the group consisting of N, NH, N($C_1$-$C_3$ alkyl), NC(O)($C_1$-$C_6$ alkyl), O, and S; and wherein said heterocyclyl is optionally substituted with from 1-3 independently selected $R^d$;
(vi) ($C_1$-$C_6$ alkyl)-($C_3$-$C_8$ cycloalkyl), wherein the cycloalkyl portion is optionally substituted with from 1-4 independently selected $R^d$; or
(vii) dihydronaphthyl, tetrahydronaphthyl, indanyl, or indenyl;

$R^a$ at each occurrence is, independently, selected from the group consisting of halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;

$R^b$ at each occurrence is, independently, selected from the group consisting of hydroxyl, $C_1$-$C_6$ alkoxy; $C_1$-$C_6$ thioalkoxy; $C_1$-$C_6$ haloalkoxy; $C_1$-$C_6$ thiohaloalkoxy; —NH$_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;

$R^c$ at each occurrence is, independently, any one of the substituents delineated collectively in (a), (b), (c), and (d) below:
(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O) ($C_1$-$C_6$ alkyl), each of which is optionally substituted with —OH, $C_1$-$C_6$ alkoxy, —NH$_2$, or —SH;
(b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH ($C_1$-$C_6$ alkyl); —SO$_2$N($C_1$-$C_6$ alkyl)$_2$; —NHCO($C_1$-$C_6$ alkyl), —NHSO$_2$($C_1$-$C_6$ alkyl); or —C(O)O— (CH$_2$)$_{1-3}$—C(O)-(phenyl optionally substituted as defined in (d) below;
(c) L-$C_3$-$C_8$ cycloalkyl, $C_3$-$C_6$ cycloalkoxy, or L-heterocyclyl containing from 5-7 ring atoms, wherein from 1-2 of the ring atoms of the heterocyclyl is independently selected from the group consisting of N, NH, N($C_1$-$C_6$ alkyl), NC(O)($C_1$-$C_6$ alkyl), NC(O)O($C_1$-$C_6$ alkyl), O, and S; and each of said ring systems is optionally substituted with from 1-3 independently selected $C_1$-$C_4$ alkyl groups; and wherein L is a bond or $C_1$-$C_6$ alkylene; and
(d) phenyl, —O-(phenyl), or heteroaryl containing from 5-6 ring atoms, wherein from 1-2 of the ring atoms of the heteroaryl is independently selected from the group consisting of N, NH, N($C_1$-$C_3$ alkyl), O, and S; wherein each of said phenyl and heteroaryl is optionally substituted with from 1-3 substituents independently selected from the group consisting of halo; hydroxyl; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —NH$_2$, or —SH;

$R^d$ at each occurrence is, independently, any one of the substituents delineated collectively in (a) and (b) below:
(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O) ($C_1$-$C_6$ alkyl), each of which is optionally substituted with —OH, $C_1$-$C_6$ alkoxy, —NH$_2$, or —SH; or
(b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH ($C_1$-$C_6$ alkyl); —SO$_2$N($C_1$-$C_6$ alkyl)$_2$; —NHCO($C_1$-$C_6$ alkyl), or —NHSO$_2$($C_1$-$C_6$ alkyl).

2. The composition of claim 1, wherein $R^{26}$ and $R^{27}$ together are a bond.

3. The composition of claim 1, wherein $R^{22}$ is $C_6$-$C_{10}$ aryl, which is optionally substituted with from 1-5 independently selected $R^a$.

4. The composition of claim 1, wherein each $R^a$ is independently selected from the group consisting of halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)($C_1$-$C_6$ alkyl); —C(O)($C_1$-$C_6$ haloalkyl); and C(O)OH.

5. The composition of claim 1, wherein one, two, or three of the independently selected $R^a$ are hydroxyl.

6. The composition of claim 1, wherein $R^{23}$ is:
(i) $C_3$-$C_6$ cycloalkyl, each of which is optionally substituted with from 1-4 independently selected $R^d$; or
(ii) $C_3$-$C_8$ branched alkyl or $C_1$-$C_8$ haloalkyl, each of which is optionally substituted with from 1-2 independently selected $R^b$.

7. The composition of claim 1, wherein $R^{25}$ is hydrogen.

8. The composition of claim 1, wherein $R^{25}$ is $C_1$-$C_8$ alkyl, which is optionally substituted with from 1-2 independently selected $R^b$.

9. The composition of claim 1, wherein $R^{24}$ is:
(i) $C_3$-$C_{10}$ cycloalkyl or $C_3$-$C_{10}$ cycloalkenyl, each of which is optionally substituted with from 1-4 independently selected $R^d$;
(ii) $C_6$-$C_{10}$ aryl, which is optionally substituted with from 1-5 independently selected $R^c$;
(iii) heteroaryl, which contains from 5-10 ring atoms, wherein from 1-4 of the ring atoms is independently selected from the group consisting of N, NH, N($C_1$-$C_3$ alkyl), O, and S; and wherein said heteroaryl ring is optionally substituted with from 1-4 independently selected $R^c$; or
(iv) heterocyclyl containing from 3-6 ring atoms, wherein from 1-2 of the ring atoms is independently selected from the group consisting of N, NH, N($C_1$-$C_3$ alkyl), NC(O)($C_1$-$C_6$ alkyl), O, and S; and wherein said heterocyclyl is optionally substituted with from 1-3 independently selected $R^d$.

10. A compound of formula (II), or a pharmaceutically acceptable salt thereof:

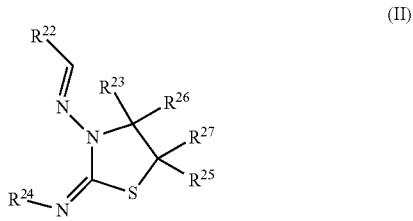

(II)

wherein:
$R^{22}$ is:
(i) $C_6$-$C_{10}$ aryl, which is optionally substituted with from 1-5 independently selected $R^a$;
(ii) heteroaryl, which contains from 5-10 ring atoms, wherein from 1-4 of the ring atoms is independently selected from the group consisting of N, NH, N($C_1$-$C_3$ alkyl), O, and S; and wherein said heteroaryl ring is optionally substituted with from 1-4 independently selected $R^a$; or
(iii) phenyl fused to $C_1$-$C_3$ alkylenedioxy, wherein the phenyl portion is optionally substituted with from 1-2 independently selected $R^a$;
$R^{23}$ is:
(i) $C_3$-$C_8$ branched alkyl or $C_1$-$C_8$ haloalkyl, each of which is optionally substituted with from 1-2 independently selected $R^b$; or
(ii) $C_3$-$C_6$ cycloalkyl or $C_3$-$C_6$ cycloalkenyl, each of which is optionally substituted with from 1-4 independently selected $R^d$;

$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl);
$R^{26}$ and $R^{27}$ together are a bond (form a second or double bond between the carbon atoms to which each is attached);
$R^{24}$ is:
(i) $C_3$-$C_{10}$ cycloalkyl or $C_3$-$C_{10}$ cycloalkenyl, each of which is optionally substituted with from 1-4 independently selected $R^d$; or
(ii) heterocyclyl containing from 3-6 ring atoms, wherein from 1-2 of the ring atoms is independently selected from the group consisting of N, NH, N($C_1$-$C_3$ alkyl), NC(O)($C_1$-$C_6$ alkyl), O, and S; and wherein said heterocyclyl is optionally substituted with from 1-3 independently selected $R^d$;
$R^a$ at each occurrence is, independently, selected from the group consisting of halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;
$R^b$ at each occurrence is, independently, selected from the group consisting of hydroxyl, $C_1$-$C_6$ alkoxy; $C_1$-$C_6$ thioalkoxy; $C_1$-$C_6$ haloalkoxy; $C_1$-$C_6$ thiohaloalkoxy; —NH$_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;
$R^c$ at each occurrence is, independently, any one of the substituents delineated collectively in (a), (b), (c), and (d) below:
(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —NH$_2$, or —SH;
(b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), —NHSO$_2$($C_1$-$C_6$ alkyl); or —C(O)O—(CH$_2$)$_{1-3}$—C(O)-(phenyl optionally substituted as defined in (d) below;
(c) L-$C_3$-$C_8$ cycloalkyl, $C_3$-$C_6$ cycloalkoxy, or L-heterocyclyl containing from 5-7 ring atoms, wherein from 1-2 of the ring atoms of the heterocyclyl is independently selected from the group consisting of N, NH, N($C_1$-$C_6$ alkyl), NC(O)($C_1$-$C_6$ alkyl), NC(O)O($C_1$-$C_6$ alkyl), O, and S; and each of said ring systems is optionally substituted with from 1-3 independently selected $C_1$-$C_4$ alkyl groups; and wherein L is a bond or $C_1$-$C_6$ alkylene; and (d) phenyl, —O—(phenyl), or heteroaryl containing from 5-6 ring atoms, wherein from 1-2 of the ring atoms of the heteroaryl is independently selected from the group consisting of N, NH, N($C_1$-$C_3$ alkyl), O, and S; wherein each of said phenyl and heteroaryl is optionally substituted with from 1-3 substituents independently selected from the group consisting of halo; hydroxyl; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —$NH_2$, or —SH;

$R^d$ at each occurrence is, independently, any one of the substituents delineated collectively in (a) and (b) below:

(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —$NH_2$, or —SH; or (b) halo; —OH; —CN; nitro; —$NH_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —$SO_2$($C_1$-$C_6$ alkyl); —$SO_2$($C_1$-$C_6$ haloalkyl); —C(O)$NH_2$; —C(O)NH($C_1$-$C_6$ alkyl); C(O)N($C_1$-$C_6$ alkyl)$_2$; —$SO_2$($C_1$-$C_6$ alkyl); —$SO_2NH_2$; —$SO_2$NH ($C_1$-$C_6$ alkyl); —$SO_2$N($C_1$-$C_6$ alkyl)$_2$; —NHCO($C_1$-$C_6$ alkyl), —$NHSO_2$($C_1$-$C_6$ alkyl).

11. The compound of claim 10, wherein $R^{22}$ has formula (A)

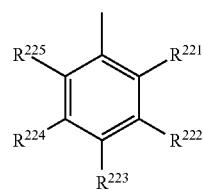

(A)

wherein:
three of $R^{221}$, $R^{222}$, $R^{223}$, $R^{224}$, and $R^{225}$ are hydroxyl, and the others are hydrogen.

12. The compound of claim 10, wherein $R^{25}$ is hydrogen or unsubstituted $C_1$-$C_3$ alkyl.

13. The compound of claim 10, wherein $R^{23}$ is $C_3$-$C_6$ cycloalkyl or $C_3$-$C_6$ cycloalkenyl, each of which is optionally substituted with from 1-4 independently selected $R^d$.

14. The compound of claim 10, wherein $R^{23}$ is branched $C_3$-$C_8$ alkyl or $C_1$-$C_8$ haloalkyl, each of which is optionally substituted with from 1-2 independently selected $R^b$.

15. The compound claim 10, wherein $R^{24}$ is $C_3$-$C_{10}$ cycloalkyl, which is optionally substituted with from 1-4 independently selected $R^d$.

16. A compound or a pharmaceutically acceptable salt thereof, wherein the compound is selected from the group consisting of the compounds shown in the following table:

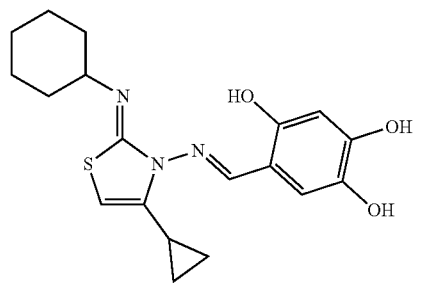

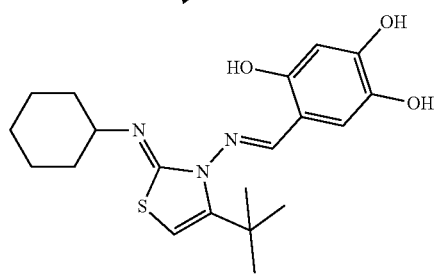

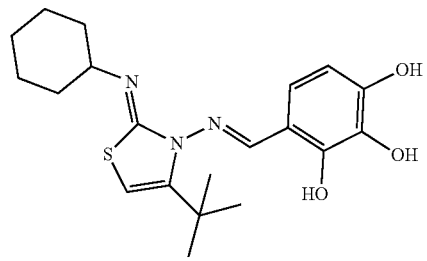

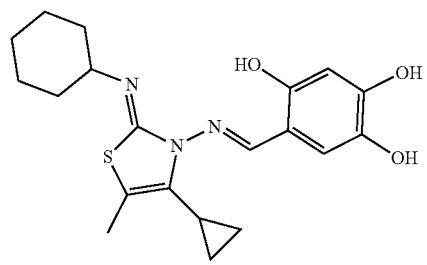

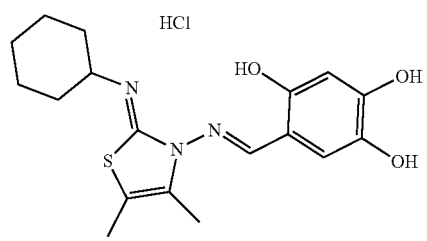

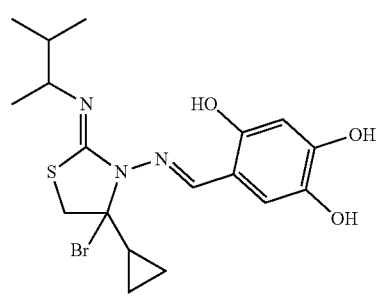

109
-continued
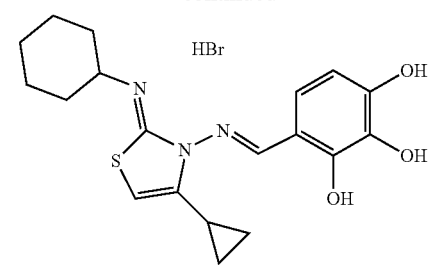
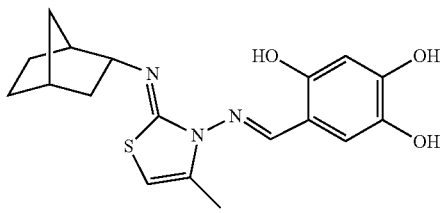
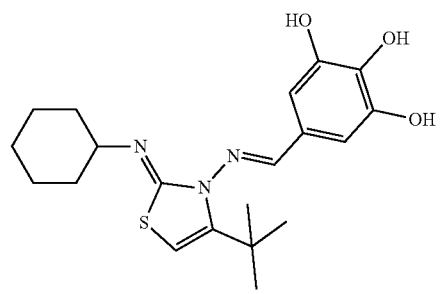
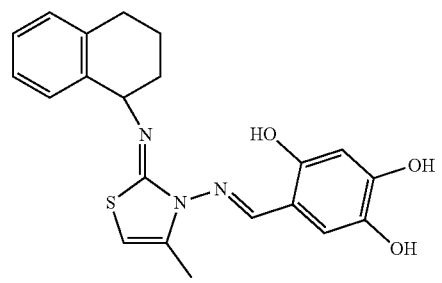
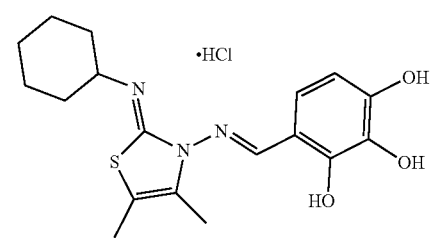
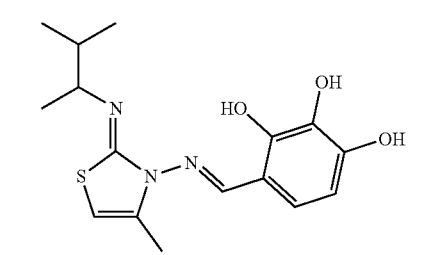
110
-continued
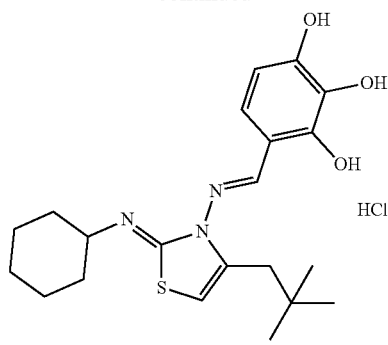
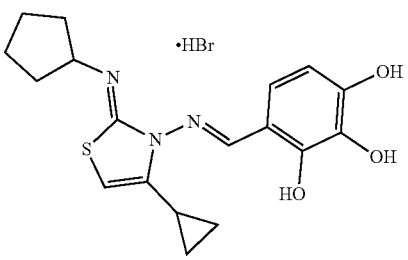
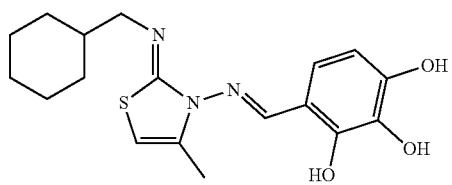
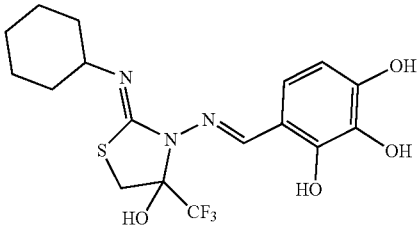
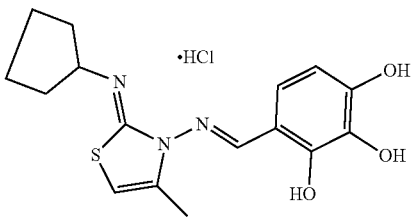
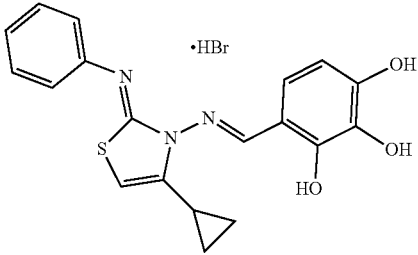

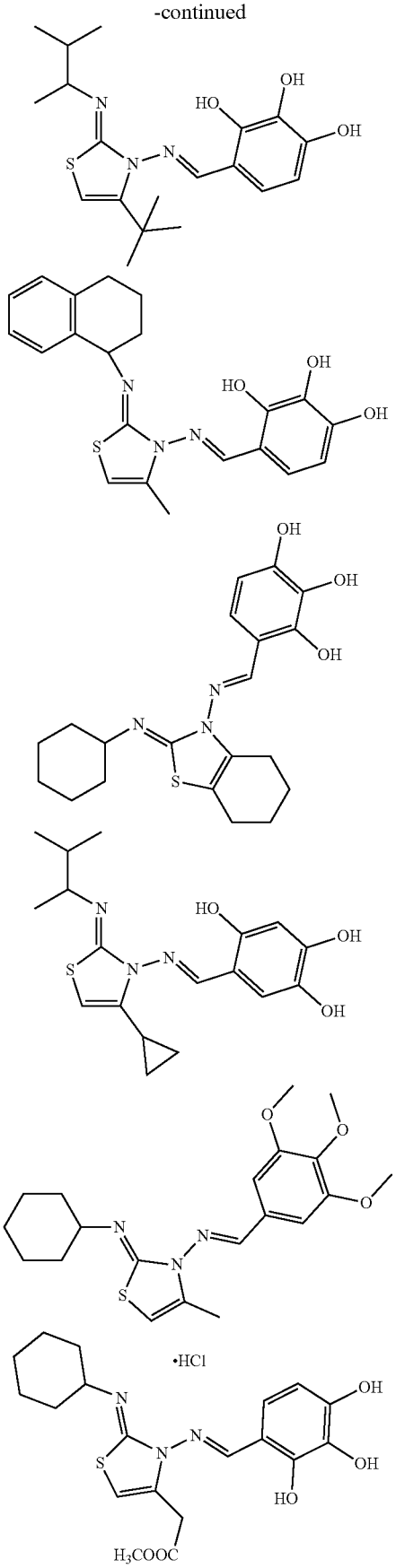
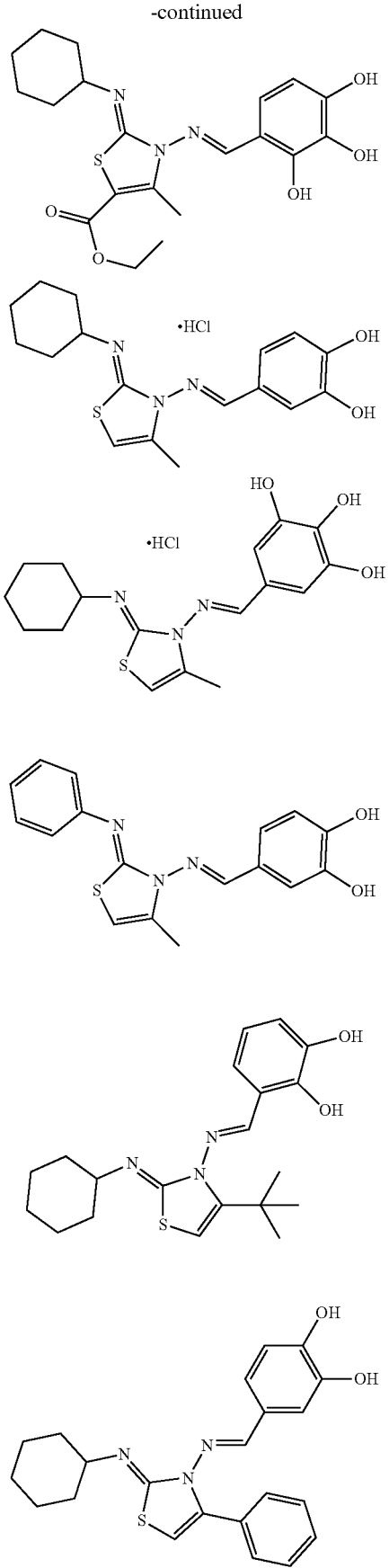

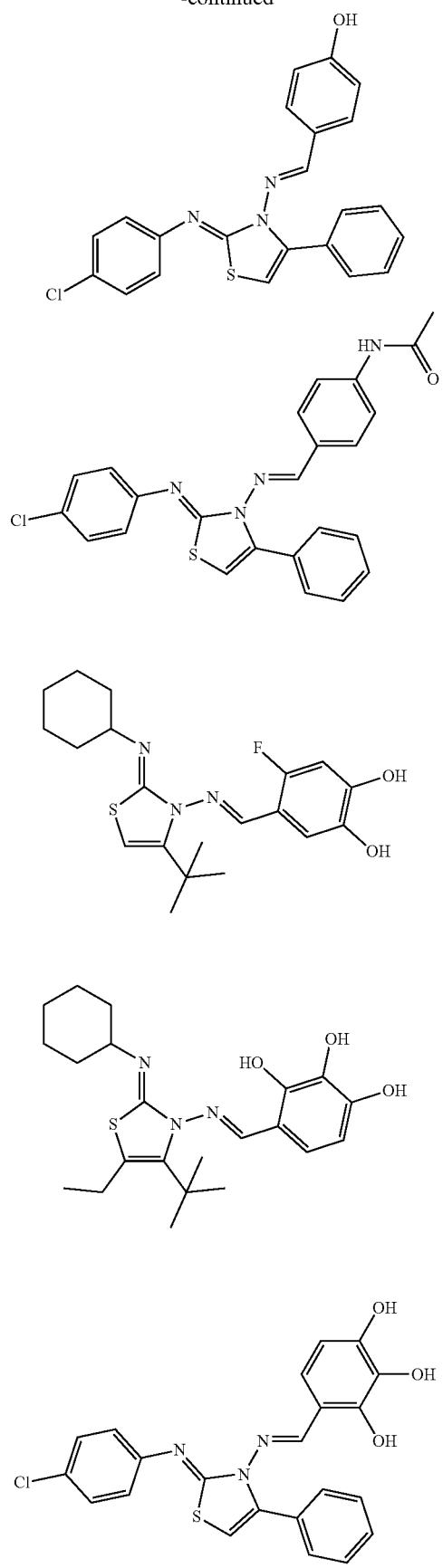

115
-continued
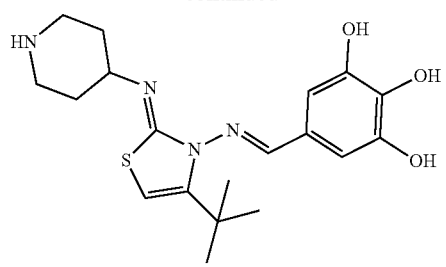
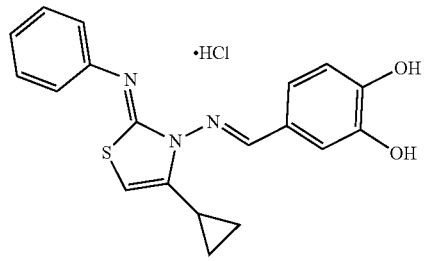
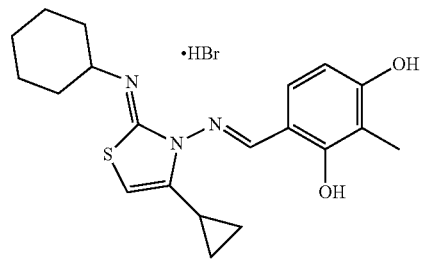
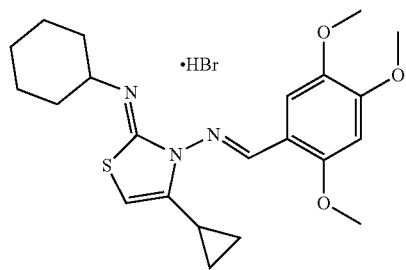
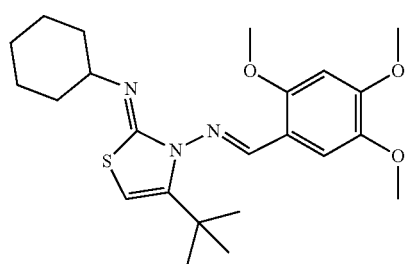
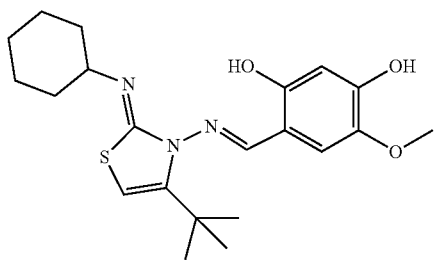
116
-continued
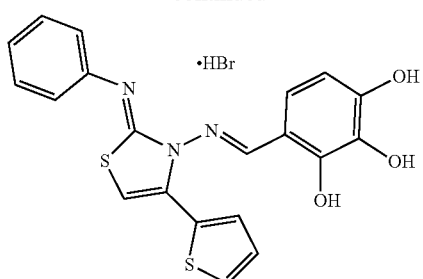
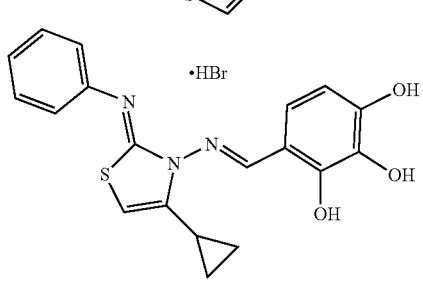
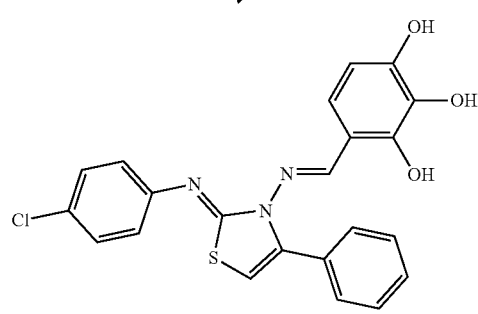
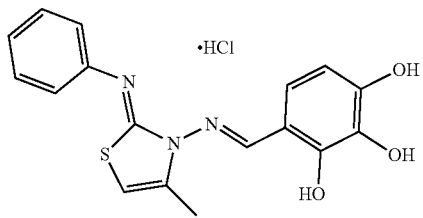
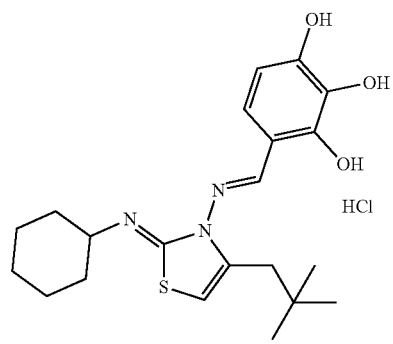
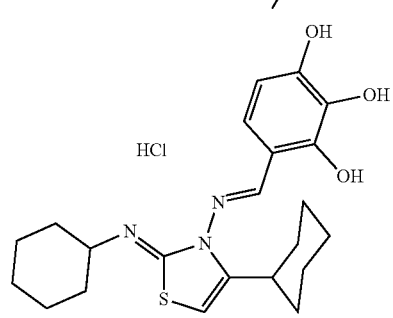

-continued

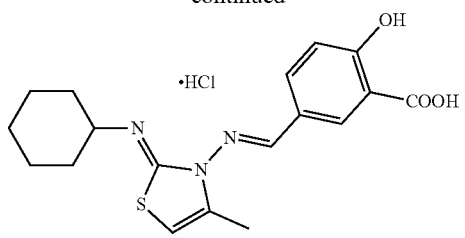

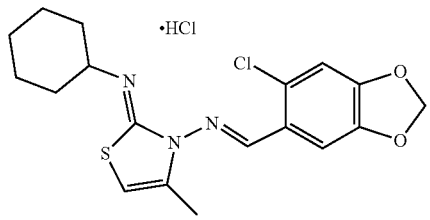

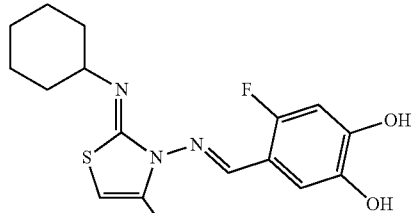

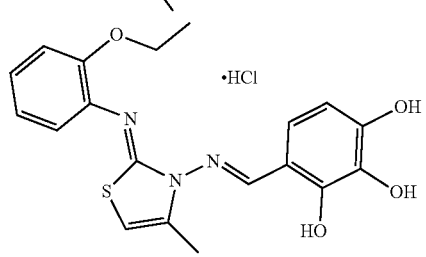

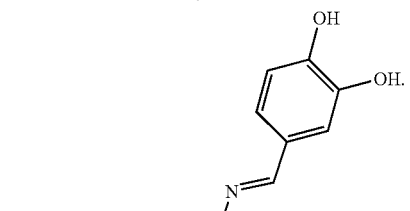

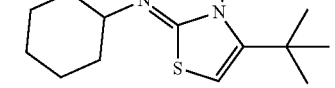

17. A pharmaceutical composition comprising a compound or salt according to claim 10 and a pharmaceutically acceptable carrier.

18. A method for inhibiting MCL-1 and/or BFL-1/A1 comprising contacting MCL-1 and/or BFL-1/A1 with a compound or salt according to claim 10.

19. A method for treating cancer comprising administering a compound or salt according to claim 10 to a subject in need thereof.

20. A pharmaceutical composition comprising:
   a compound or a pharmaceutically acceptable salt thereof; and
   one or more additional therapeutic agents;
   wherein the compound is selected from the group consisting of the compounds shown in the following table:

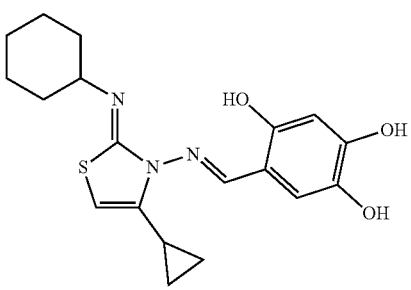

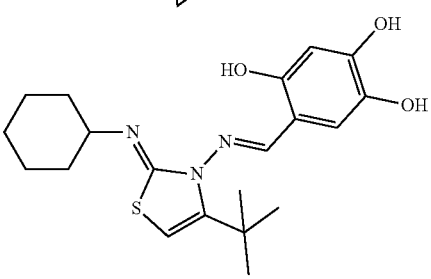

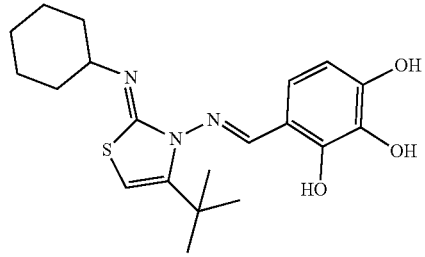

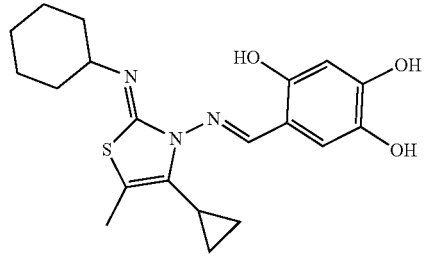

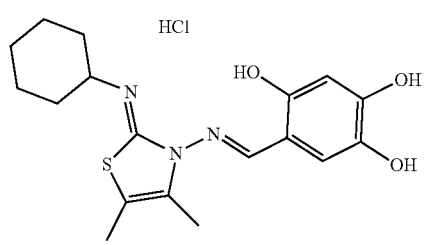

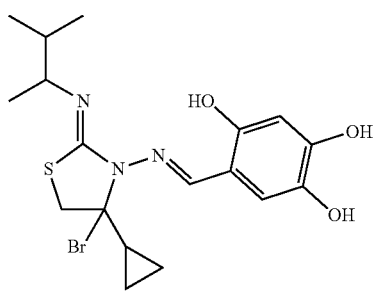

119
-continued
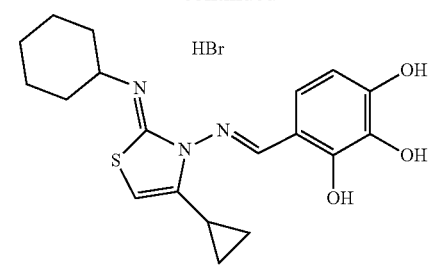
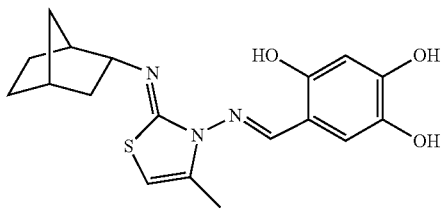
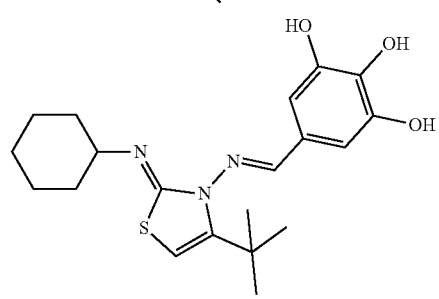
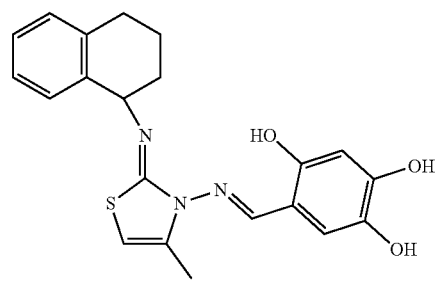
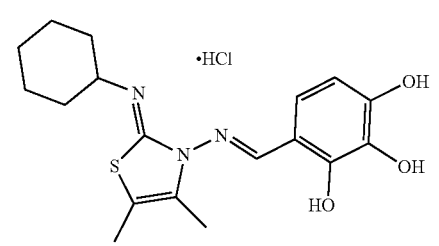
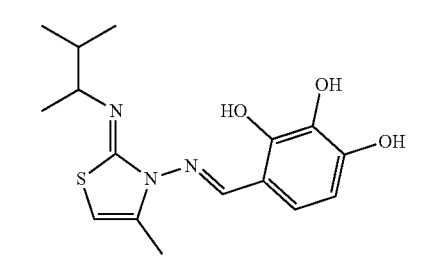
120
-continued
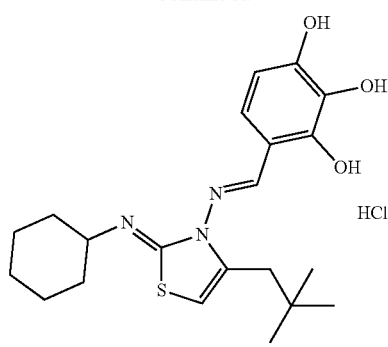
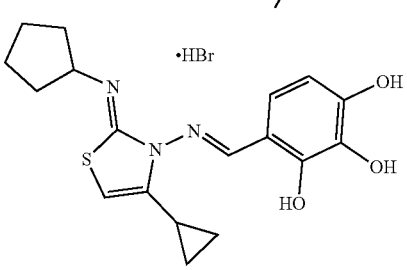
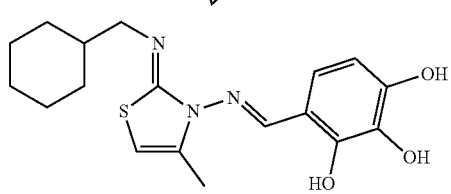
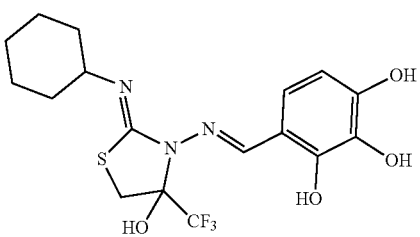
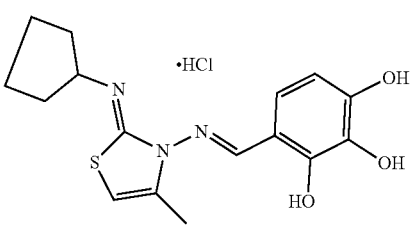
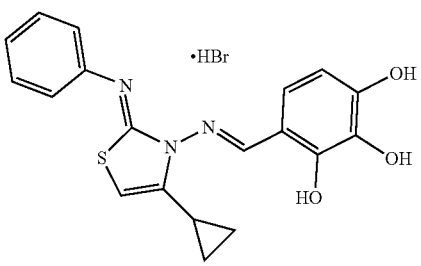

121
-continued
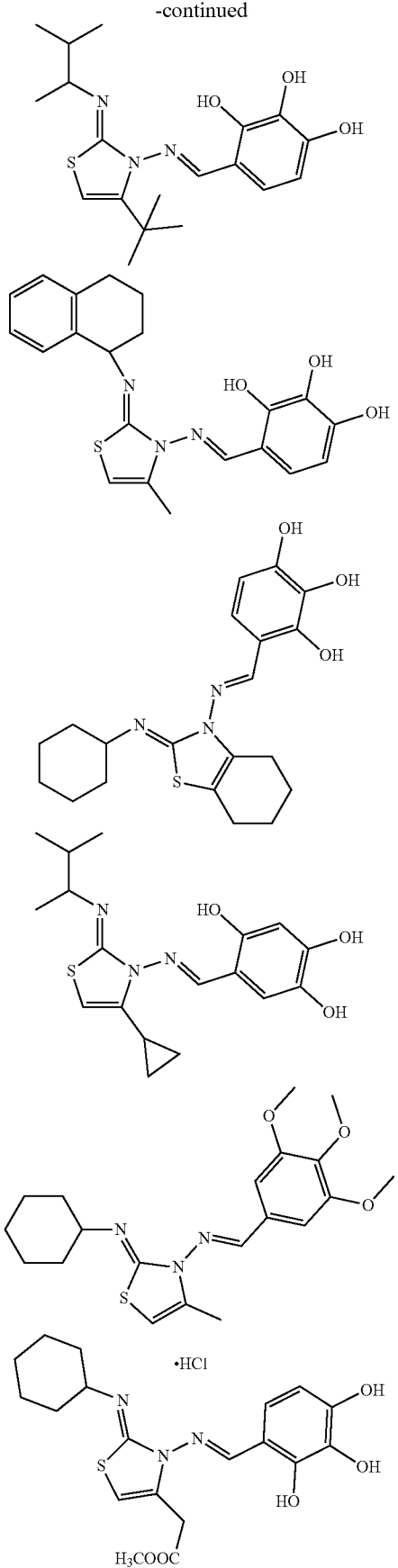
122
-continued
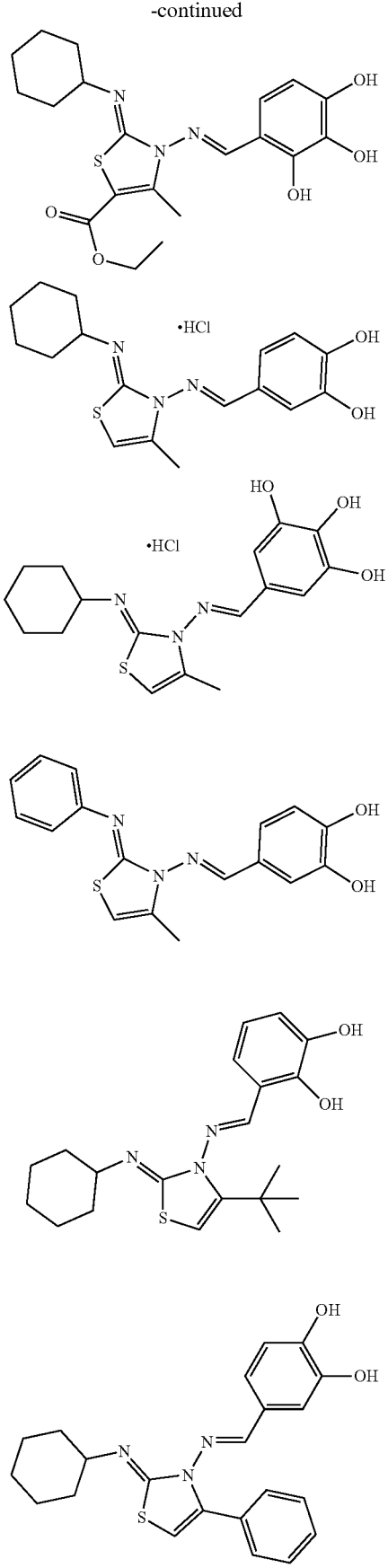

123
-continued
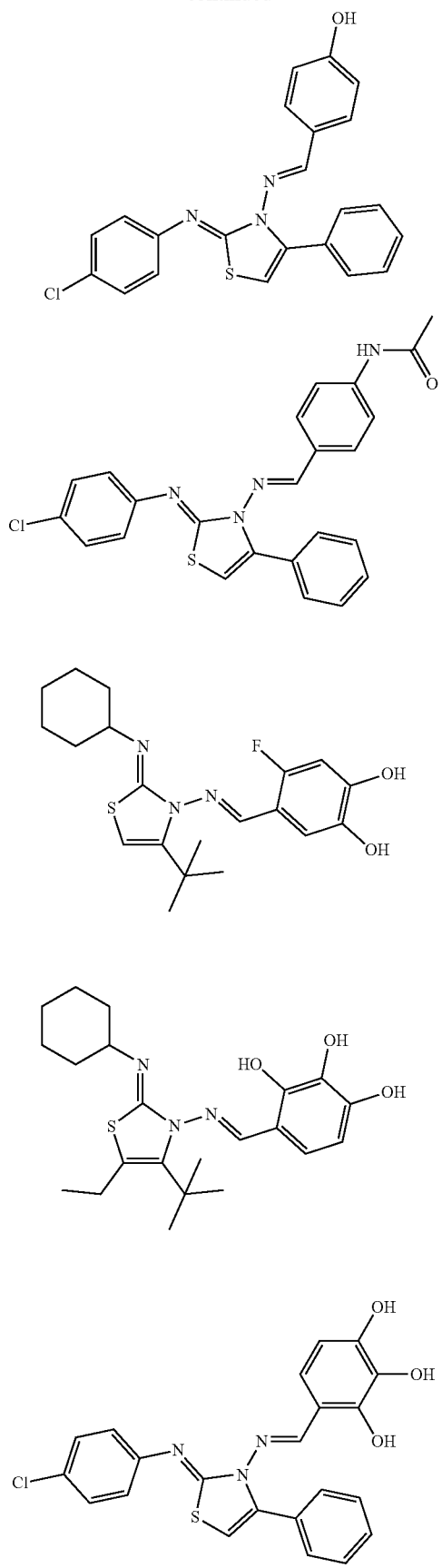
124
-continued
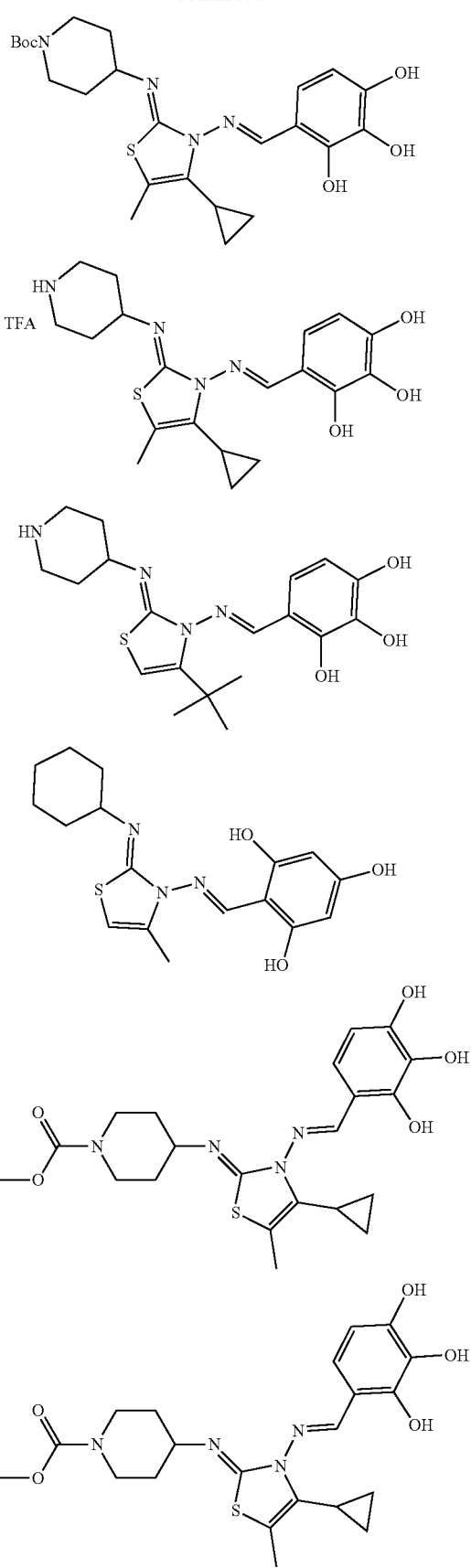

-continued
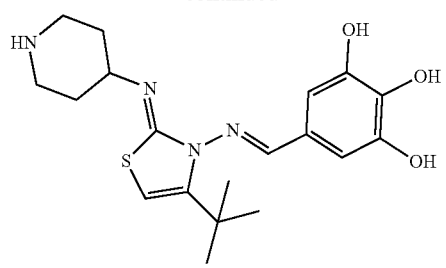
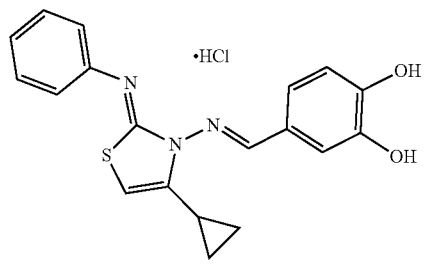
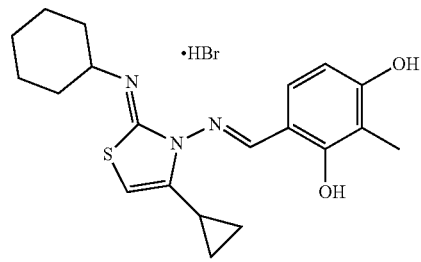
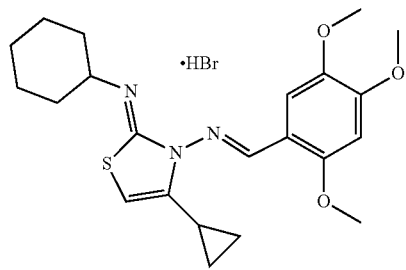
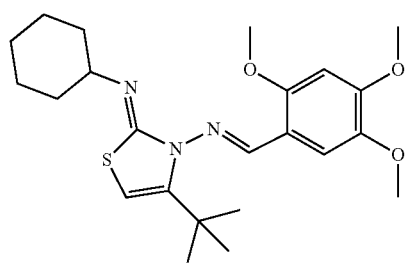
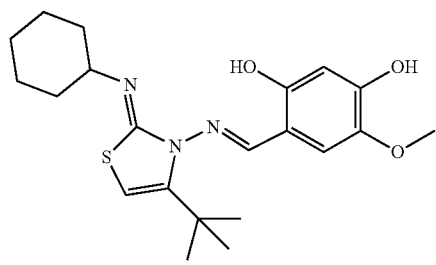
-continued
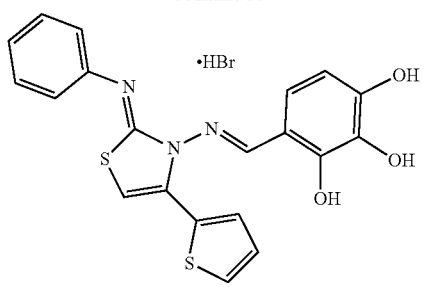
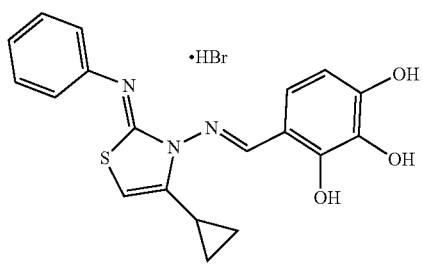
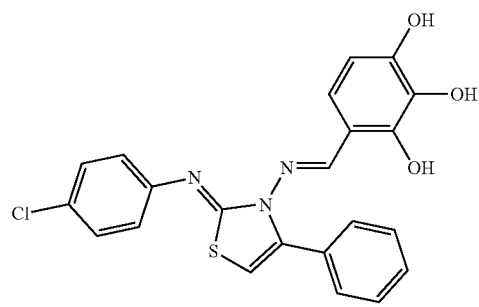
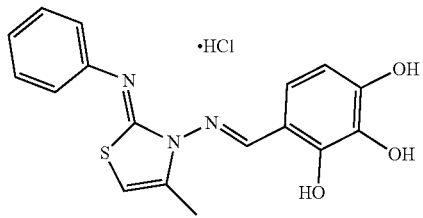
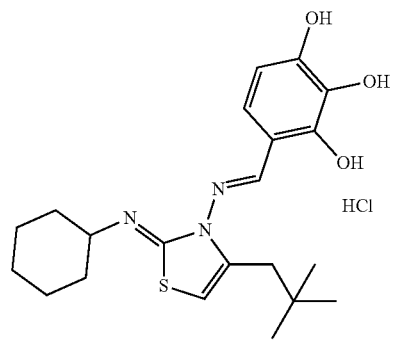
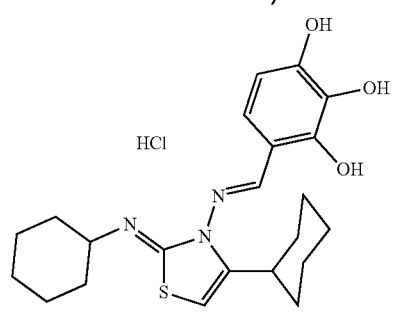

-continued
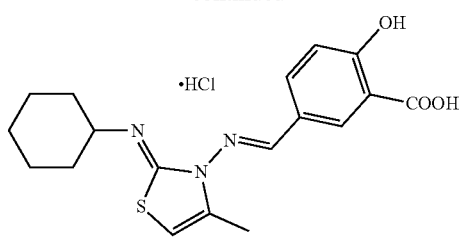
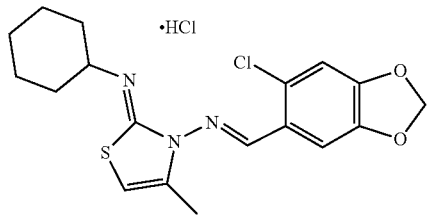
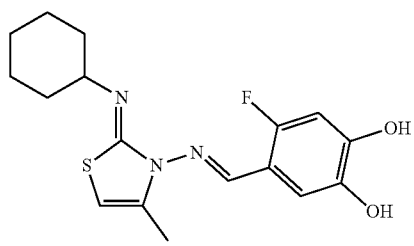
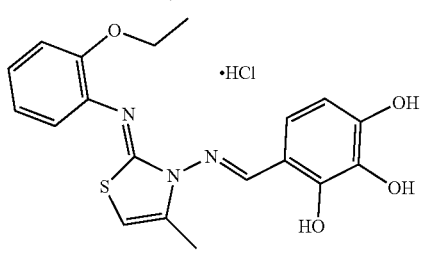
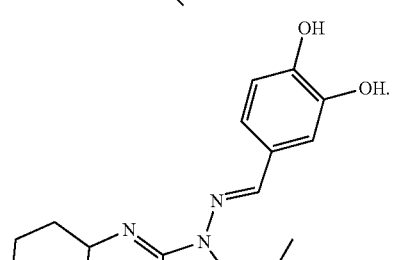
21. The compound of claim 16, wherein the compound is
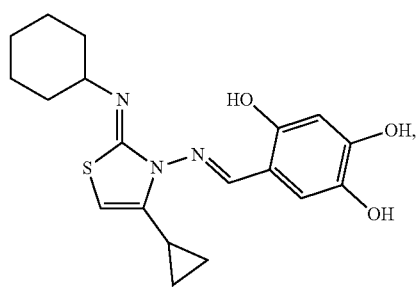
-continued
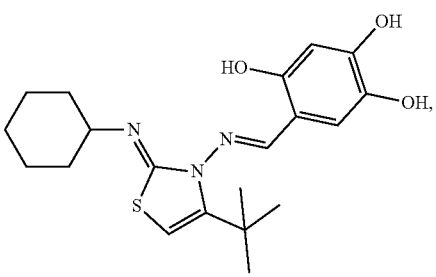
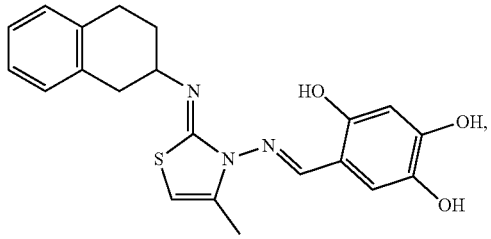
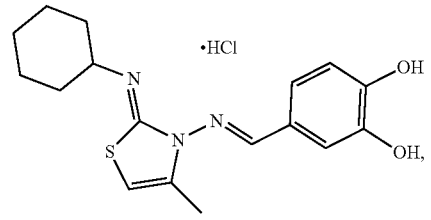
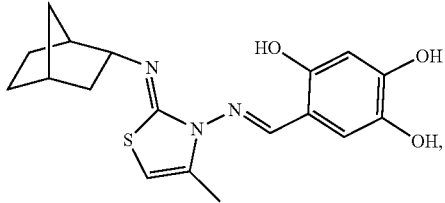
or a pharmaceutically acceptable salt thereof.
22. The composition of claim 20, wherein the compound is
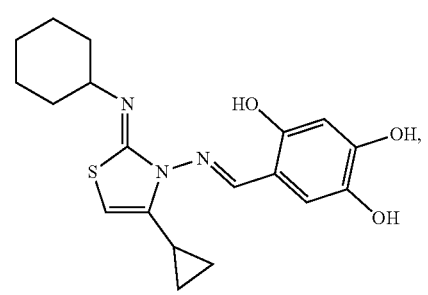
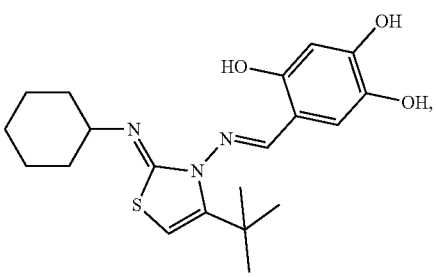

-continued

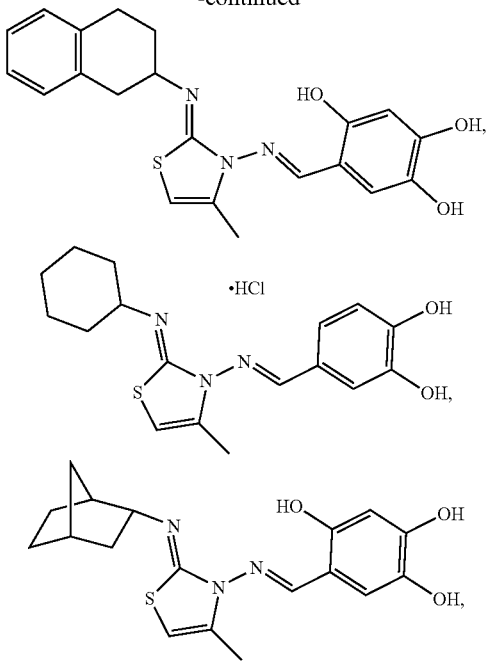

or a pharmaceutically acceptable salt thereof.

23. A pharmaceutical composition, comprising:
a compound of formula (II) or a pharmaceutically acceptable salt thereof; and
one or more additional therapeutic agents or a pharmaceutically acceptable salt of the agent:

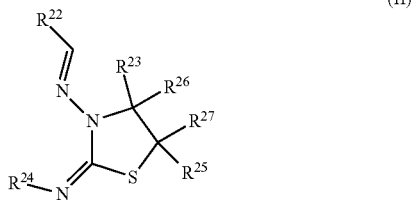

(II)

wherein:
$R^{22}$ is:
(i) $C_6$-$C_{10}$ aryl, which is optionally substituted with from 1-5 independently selected $R^a$;
(ii) heteroaryl, which contains from 5-10 ring atoms, wherein from 1-4 of the ring atoms is independently selected from the group consisting of N, NH, N($C_1$-$C_3$ alkyl), O, and S; and wherein said heteroaryl ring is optionally substituted with from 1-4 independently selected $R^a$; or
(iii) phenyl fused to $C_1$-$C_3$ alkylenedioxy, wherein the phenyl portion is optionally substituted with from 1-2 independently selected $R^a$;
$R^{23}$ is:
(i) $C_3$-$C_8$ branched alkyl or $C_1$-$C_8$ haloalkyl, each of which is optionally substituted with from 1-2 independently selected $R^b$;
(ii) heteroaryl is optionally substituted with from 1-3 independently selected $R^c$;
(iii) $C_3$-$C_6$ cycloalkyl or $C_3$-$C_6$ cycloalkenyl, each of which is optionally substituted with from 1-4 independently selected $R^d$;

$R^{25}$ is:
(i) hydrogen;
(ii) $C_1$-$C_8$ alkyl or $C_1$-$C_8$ haloalkyl, each of which is optionally substituted with from 1-2 independently selected $R^b$;
(iii) $C_3$-$C_6$ cycloalkyl or $C_3$-$C_6$ cycloalkenyl, each of which is optionally substituted with from 1-4 independently selected $R^d$; or
(iv) —C(O)O($C_1$-$C_6$ alkyl);
or
$R^{23}$ and $R^{25}$, together with the carbon atoms to which each is attached, form:
(i) a 5-6 membered saturated or unsaturated carbocyclic ring, which is optionally substituted with from 1-4 independently selected $R^d$; or
(ii) a 5-6 membered saturated or unsaturated hetrocyclic ring, which is optionally substituted with from 1-4 independently selected $R^d$, and wherein from 1-2 of the ring atoms (other than the two ring atoms attached to $R^{23}$ and $R^{24}$) is independently selected from the group consisting of N, NH, N($C_1$-$C_3$ alkyl), NC(O)($C_1$-$C_6$ alkyl), O, and S;
$R^{26}$ and $R^{27}$ together are a bond (form a second or double bond between the carbon atoms to which each is attached); or
each of $R^{26}$ and $R^{27}$ is independently selected from the group consisting of hydrogen, halo, and hydroxyl;
$R^{24}$ is:
(i) $C_3$-$C_{10}$ cycloalkyl or $C_3$-$C_{10}$ cycloalkenyl, each of which is optionally substituted with from 1-4 independently selected $R^d$;
(ii) $C_6$-$C_{10}$ aryl, which is optionally substituted with from 1-5 independently selected $R^c$;
(iii) heteroaryl, which contains from 5-10 ring atoms, wherein from 1-4 of the ring atoms is independently selected from the group consisting of N, NH, N($C_1$-$C_3$ alkyl), O, and S; and wherein said heteroaryl ring is optionally substituted with from 1-4 independently selected $R^c$;
(iv) unsubstituted $C_1$-$C_8$ alkyl or unsubstituted $C_1$-$C_8$ haloalkyl;
(v) heterocyclyl containing from 3-6 ring atoms, wherein from 1-2 of the ring atoms is independently selected from the group consisting of N, NH, N($C_1$-$C_3$ alkyl), NC(O)($C_1$-$C_6$ alkyl), O, and S; and wherein said heterocyclyl is optionally substituted with from 1-3 independently selected $R^d$;
(vi) ($C_1$-$C_6$ alkyl)-($C_3$-$C_8$ cycloalkyl), wherein the cycloalkyl portion is optionally substituted with from 1-4 independently selected $R^d$; or
(vii) dihydronaphthyl, tetrahydronaphthyl, indanyl, or indenyl;
$R^a$ at each occurrence is, independently, selected from the group consisting of halo, hydroxyl, $C_1$-$C_6$ alkoxy; $C_1$-$C_6$ haloalkoxy; $C_1$-$C_6$ thiohaloalkoxy; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;
$R^b$ at each occurrence is, independently, selected from the group consisting of hydroxyl, $C_1$-$C_6$ alkoxy; $C_1$-$C_6$ thioalkoxy; $C_1$-$C_6$ haloalkoxy; $C_1$-$C_6$ thiohaloalkoxy; —NH$_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH($C_1$-$C_6$ alkyl);

C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$;

$R^c$ at each occurrence is, independently, any one of the substituents delineated collectively in (a), (b), (c), and (d) below:

(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —NH$_2$, or —SH;

(b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), —NHSO$_2$($C_1$-$C_6$ alkyl); or —C(O)O—(CH$_2$)$_{1-3}$—C(O)-(phenyl optionally substituted as defined in (d) below;

(c) L-$C_3$-$C_8$ cycloalkyl, $C_3$-$C_6$ cycloalkoxy, or L-heterocyclyl containing from 5-7 ring atoms, wherein from 1-2 of the ring atoms of the heterocyclyl is independently selected from the group consisting of N, NH, N($C_1$-$C_6$ alkyl), NC(O)($C_1$-$C_6$ alkyl), NC(O)O($C_1$-$C_6$ alkyl), O, and S; and each of said ring systems is optionally substituted with from 1-3 independently selected $C_1$-$C_4$ alkyl groups; and wherein L is a bond or $C_1$-$C_6$ alkylene; and (d) phenyl, —O-(phenyl), or heteroaryl containing from 5-6 ring atoms, wherein from 1-2 of the ring atoms of the heteroaryl is independently selected from the group consisting of N, NH, N($C_1$-$C_3$ alkyl), O, and S; wherein each of said phenyl and heteroaryl is optionally substituted with from 1-3 substituents independently selected from the group consisting of halo; hydroxyl; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —NH$_2$, or —SH;

$R^d$ at each occurrence is, independently, any one of the substituents delineated collectively in (a) and (b) below:

(a) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, $C_1$-$C_6$ alkoxy, —NH$_2$, or —SH; or (b) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), or —NHSO$_2$($C_1$-$C_6$ alkyl).

* * * * *

UNITED STATES PATENT AND TRADEMARK OFFICE
CERTIFICATE OF CORRECTION

| | | |
|---|---|---|
| PATENT NO. | : 9,926,306 B2 | Page 1 of 1 |
| APPLICATION NO. | : 14/386747 | |
| DATED | : March 27, 2018 | |
| INVENTOR(S) | : Loren D. Walensky | |

It is certified that error appears in the above-identified patent and that said Letters Patent is hereby corrected as shown below:

In the Claims

Column 101, Line 49, in Claim 1:
Delete "combination" and insert -- composition --, therefor.

Column 103, Line 16, in Claim 1:
Delete "hetrocyclic" and insert -- heterocyclic --, therefor.

Column 104, Line 20, in Claim 1:
After "(phenyl", insert -- ) --, therefor.

Column 106, Line 57, in Claim 10:
After "(phenyl", insert -- ) --, therefor.

Column 130, Line 16, in Claim 23:
Delete "hetrocyclic" and insert -- heterocyclic --, therefor.

Column 131, Line 21, in Claim 23:
After "(phenyl", insert -- ) --, therefor.

Signed and Sealed this
Twelfth Day of June, 2018

Andrei Iancu
*Director of the United States Patent and Trademark Office*